United States Patent
Joung et al.

(10) Patent No.: US 9,850,484 B2
(45) Date of Patent: Dec. 26, 2017

(54) COMPREHENSIVE IN VITRO REPORTING OF CLEAVAGE EVENTS BY SEQUENCING (CIRCLE-SEQ)

(71) Applicant: The General Hospital Corporation, Boston, MA (US)

(72) Inventors: J. Keith Joung, Winchester, MA (US); Shengdar Tsai, Memphis, TN (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/282,800

(22) Filed: Sep. 30, 2016

(65) Prior Publication Data

US 2017/0088833 A1    Mar. 30, 2017

Related U.S. Application Data

(60) Provisional application No. 62/235,154, filed on Sep. 30, 2015.

(51) Int. Cl.
  *C12N 15/10* (2006.01)
  *C12Q 1/68* (2006.01)

(52) U.S. Cl.
  CPC ..... *C12N 15/1093* (2013.01); *C12N 15/1031* (2013.01); *C12Q 1/6855* (2013.01); *C12Q 1/6869* (2013.01)

(58) Field of Classification Search
  None
  See application file for complete search history.

(56) References Cited

U.S. PATENT DOCUMENTS

| | | |
|---|---|---|
| 7,803,550 B2 | 9/2010 | Makarov et al. |
| 8,071,312 B2 | 12/2011 | Makarov et al. |
| 8,399,199 B2 | 3/2013 | Makarov et al. |
| 8,420,319 B2 | 4/2013 | Mikawa |
| 8,728,737 B2 | 5/2014 | Makarov et al. |
| 2006/0292611 A1 | 12/2006 | Berka et al. |
| 2009/0082295 A1 | 3/2009 | Jungnelius et al. |
| 2010/0317722 A1 | 12/2010 | Lavon |
| 2011/0060493 A1 | 3/2011 | Miura et al. |
| 2011/0287545 A1 | 11/2011 | Cost |
| 2013/0137605 A1 | 5/2013 | Shendure et al. |
| 2013/0143204 A1 | 6/2013 | Von Kalle |
| 2013/0303461 A1 | 11/2013 | Iafrate et al. |
| 2013/0309668 A1 | 11/2013 | Makarov et al. |

(Continued)

FOREIGN PATENT DOCUMENTS

| | | |
|---|---|---|
| WO | WO 2012/065143 | 5/2012 |
| WO | WO 2013078470 | 5/2013 |

(Continued)

OTHER PUBLICATIONS

Zhou et al., "HTS-PEG: A Method for High Throughput Sequencing of the Paired-Ends of Genomic Libraries," PLoS ONE 2012, 7(12):e52257.*

(Continued)

*Primary Examiner* — Kaijiang Zhang
(74) *Attorney, Agent, or Firm* — Fish & Richardson P.C.

(57) ABSTRACT

Sensitive, unbiased methods for genome-wide detection of potential CRISPR-Cas9 off-target cleavage sites from cell type-specific genomic DNA samples.

19 Claims, 21 Drawing Sheets

(56) References Cited

U.S. PATENT DOCUMENTS

2014/0024542 A1 1/2014 Richards
2014/0295557 A1 10/2014 Joung et al.

FOREIGN PATENT DOCUMENTS

WO WO 2014/093701 6/2014
WO WO 2015/200378 12/2015

OTHER PUBLICATIONS

"thermofisher.com" {online}. ""PCR Methods-Top Ten Strategies,"" 2017, [retrieved on Feb. 1, 2017] Retrieved from the Internet: URL<https://www.thermofisher.com/us/en/home/life-science/cloning/cloning-learningcenter/invitrogen-school-of-molecular-biology/per-education/per-reagents-enzymes/per-methods.html>. 10 pages.".
'ncbi.nlm.nih.gov' [online]. "Homologs Are Descended from a Common Ancestor," 2002, [retrieved on Jan. 30, 2017]. Retrieved from the Internet: URL <https://www.ncbi.nlm.nih.gov/books/NBK22355/>. 1 page.
International Search Report and Written Opinion in International Application No. PCT/US16/51097, dated Jan. 24, 2017, 12 pages.
International Search Report and Written Opinion in International Application No. PCT/US16/54912, dated Jan. 24, 2017, 12 pages.
Mullis and Faloona, "Specific synthesis of DNA in vitro via a polymerase-catalyzed chain reaction," Methods in Enzymology, 1987, 155: 335-350.
Office Action in U.S. Appl. No. 15/192,753, dated Feb. 9, 2017, 43 pages.
Bolukbasi et al., "Creating and evaluating accurate CRISPR-Cas9 scalpels for genomic surgery," Nat Meth, Jan. 2016, 13: 41-50.
Cencic et al., "Protospacer Adjacent Motif (PAM)-Distal Sequences Engage CRISPR Cas9 DNA Target Cleavage," Oct. 2014, PLOS One, 9(10): e109213.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choi & Meyerson, "Targeted genomic rearrangements using CRISPR/Cas technology," Nat Commun., Apr. 24, 2014, 5:3728, doi: 10.1038/ncomms4728.
Cong et al., "Multiplex genome engineering using CRISPR/Cas systems," Science, 2013, 339:819-823 (Author Manuscript).
Cox et al., "Therapeutic genome editing: prospects and challenges," Nat Med, 2015, 21:121-131.
Cradick et al., "CRISPR/Cas9 systems targeting beta-globin and CCR5 genes have substantial off-target activity," Nucleic Acids Res., 2013, 41(20):9584-92.
Crosetto et al, "Nucleotide-resolution DNA double-strand break mapping by next-generation sequencing," Apr. 2013, Nat Methods 10(4): 361-365.
DiCarlo et al., "Genome engineering in *Saccharomyces cerevisiae* using CRISPR-Cas systems," Nucleic Acids Res, 2013, 41(7):4336.
Duan et al., "Genome-wide identification of CRISPR/Cas9 off-targets in human genome," Cell Res, 2014, 24(8):1009-1012.
Fonfara et al., "Phylogeny of Cas9 determines functional exchangeability of dual-RNA and Cas9 among orthologous type II CRISPR-Cas systems," 2014, Nucleic Acids Res 42(4): 2577-2590.
Frock et al., "Genome-wide detection of DNA double-stranded breaks induced by engineered nucleases," Nat Biotechnol, Feb. 2015, 33: 179-486.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat Biotechnol, Mar. 2014, 32(3): 279-284.

Gabriel et al., "An unbiased genome-wide analysis of zinc-finger nuclease specificity," Nat Biotechnol, Sep. 2011, 29(9): 816-823.
Gaj et al., "ZFN, TALEN and CRISPR/Cas-based methods for genome engineering," Trends Biotechnol,, Jul. 2013, 31(7):397-405.
Ghezraoui et al., "Chromosomal translocations in human cells are generated by canonical nonhomologous end-joining," Mol Cell Sep. 18, 2014, 55: 829-842.
Gnirke et al., "Solution hybrid selection with ultra-long oligonucleotides for massively parallel targeted sequencing," Nature Biotechnology, 2009, 27: 182-189.
Gori et al., "Delivery and Specificity of CRISPR-Cas9 Genome Editing Technologies for Human Gene Therapy," Hum Gene Ther, 2015, 26: 443-451.
Gostissa et al., "IgH class switching exploits a general property of two DNA breaks to be joined in cis over long chromosomal distances," Proc Natl Acad Sci, Feb. 18, 2014, 111(7): 2644-2649.
Guilinger et al., "Fusion of catalytically inactive Cas9 to FokI nuclease improves the specificity of genome modification," Nat Biotechnol, Jun. 2014, 32(6): 577-582.
Heigwer et al., "E-CRISP: fast CRISPR target site identification," Nat Methods, Feb. 2014, 11: 122-123.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Hwang et al., "Efficient In Vivo Genome Editing Using RNA-Guided Nucleases," Nat Biotechnol., 2013, 31:227-229 (Author Manuscript).
International Search Report and Written Opinion in International Application No. PCT/US15/37269, dated Oct. 15, 2015, 26 pages.
Jiang et al., "Characterization of *Escherichia coli* Endonuclease VIII," J. Biol. Chem, 1997, 272:32230-32239.
Jiang et al., "CRISPR-assisted editing of bacterial genomes," Nat Biotechnol, Mar. 2013, 31(3): 233-239.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Kim et al., "Digenome-seq: genome-wide profiling of CRISPR-Cas9 off-target effects in human cells," Nat Meth, Mar. 2015, 12: 237-243.
Kim et al., "Genome-wide target specificities of CRISPR-Cas9 nucleases revealed by multiplex Digenome-seq.," Genome Res, 2016, 26: 406-415.
Kuscu et al., "Genome-wide analysis reveals characteristics of off-target sites bound by the Cas9 endonuclease," Nat Biotechnol, Jul. 2014, 32 (7): 677-683.
Lin et al., "CRISPR/Cas9 systems have off-target activity with insertions or deletions between target DNA and guide RNA sequences," Nucleic Acids Res, 2014, 42(11): 7473-7485.
Lindahl, "DNA repair enzymes," Annu. Rev. Biochem, 1982, 51:61-64.
Lindhal et al., "DNA N-glycosidases: properties of uracil-DNA glycosidase from *Escherichia coli*," J. Biol. Chem., May 1977, 252:3286-3294.
Mali et al, "CAS9 transcriptional activators for target specificity screening and paired nickases for cooperative genome engineering," Nat Biotechnol, Sep. 2013, 31(9): 833-838.
Mali et al., "RNA-guided human genome engineering via Cas9," Science, Feb. 2013, 339:823-826 (Author Manuscript).
Marx et al., "Gene editing: how to stay on-target with CRISPR," Nat Methods, 2014, 11:1021-1026.
Melamede et al., "Isolation and characterization of endonuclease VIII from *Escherichia coli*," Biochemistry, Feb. 1994, 33:1255-1264.
Ochman et al., Genetic Applications of an Inverse Polymerase Chain Reaction, Genetics, Nov. 1998, 120: 621-623.
Orlando et al., "Zinc-finger nuclease-driven targeted integration into mammalian genomes using donors with limited chromosomal homology," Nucleic Acids Res, 2010, 38(15): e152.

(56) References Cited

OTHER PUBLICATIONS

Osborn et al., "TALEN-based gene correction for epidermolysis bullosa," 2013, Mol Ther, 21: 1151-1159.
Pattanayak et al., "High-throughput profiling of off-target DNA cleavage reveals RNA-programmed Cas9 nuclease specificity," Nat Biotechnol., 2013, 31:839-843 (Author Manuscript).
Ran et al., "Double nicking by RNA-guided CRISPR Cas9 for enhanced genome editing specificity," Cell, Sep. 2013, 154: 1380-1389.
Ran et al., "Genome engineering using the CRISPR-Cas9 system," Nat Protoc, Nov. 2013, 8(11): 2281-2308.
Ran et al., "In vivo genome editing using *Staphylococcus aureus* Cas9," Nature, Apr. 2015, 520, 186-191.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res, Oct. 2013, 41(19): e181.
Schmidt et al., "High-resolution insertion-site analysis by linear amplification-mediated PCR (LAM-PCR)," Nat Methods, Dec. 2007, 4(12): 1051-1057.
Shen et al., "Generation of gene-modified mice via Cas9/RNA-mediated gene targeting," Cell Res, 2013, 23:720-723.
Smith et al, "Whole-genome sequencing analysis reveals high specificity of CRISPR/Cas9 and TALEN-based genome editing in human iPSCs," Cell Stem Cell, Jul. 3, 2014, 15(1):12-13.
Tsai and Joung, "Defining and improving the genome- wide specificities of CRISPR-Cas9 nucleases," Nature, Apr. 2016, 17: 300-312.
Tsai et al., "Dimeric CRISPR RNA-guided FokI nucleases for highly specific genome editing," Nat Biotechnol, Jun. 2014, 32(6): 569-576.
Tsai et al., "GUIDE-seq Enables Genome-Wide Profiling of Off-Target Cleavage by CRISPR-Cas Nucleases," Nature Biotechnology, Dec. 2014, 187-197.
Tsai et al., "What's changed with genome editing?," Jul. 2014, Cell Stem Cell, 15(1): 3-4.
Veres et al., "Low incidence of off-target mutations in individual CRISPR-Cas9 and TALEN targeted human stem cell clones detected by whole-genome sequencing," Cell Stem Cell, Jul. 3, 2014, 15: 27-30.
Wu et al., "Genome-wide binding of the CRISPR endonuclease Cas9 in mammalian cells," Nat Biotechnol. Jul. 2014; 32(7):670-6.
Yang et al., "Targeted and genome-wide sequencing reveal single nucleotide variations impacting specificity of Cas9 in human stem cells," Nature Communications, Nov. 2014, 5: 5507.
Zheng et al., "Anchored multiplex PCR for targeted next-generation sequencing," Nat Med, Nov. 10, 2014, 20(12): 1479-1484.
Cameron et al., "Mapping the genomic landscape of CRISPR—Cas9 cleavage," Nature Methods, 2017, 10 pages.
Canela et al., "DNA Breaks and End Resection Measured Genomewide by End Sequencing," Molecular Cell, 2016, 63: 1-14.

* cited by examiner

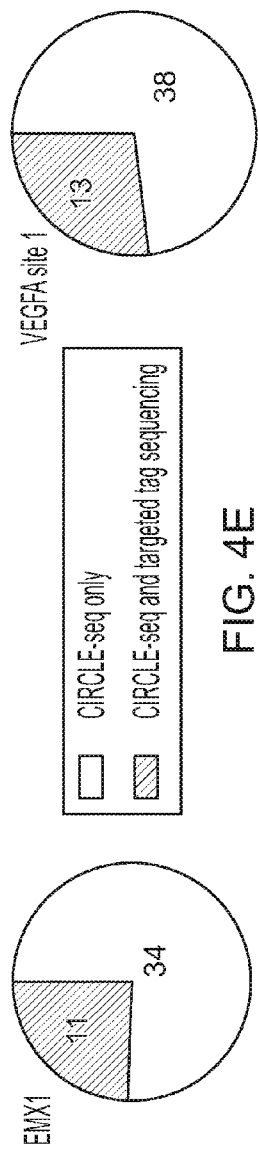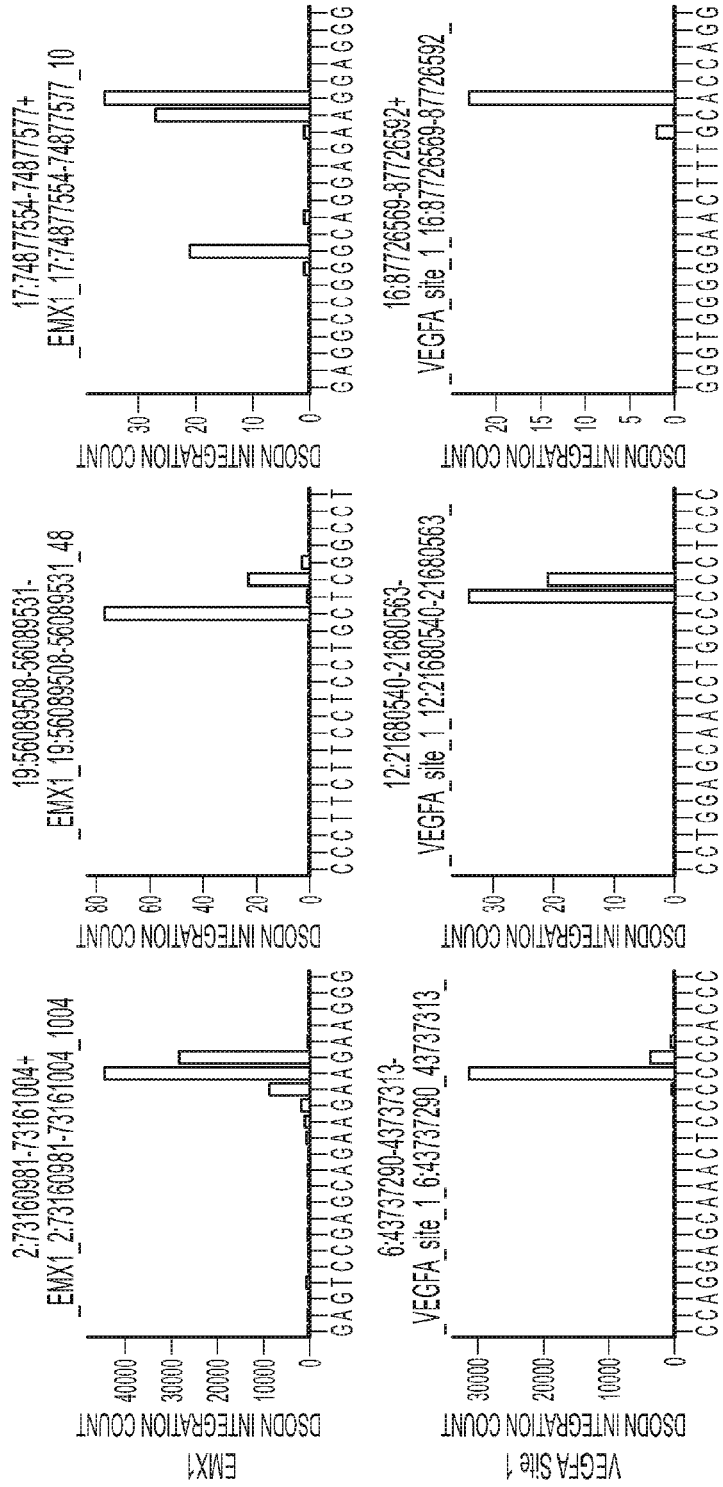
FIG. 4E
FIG. 4F

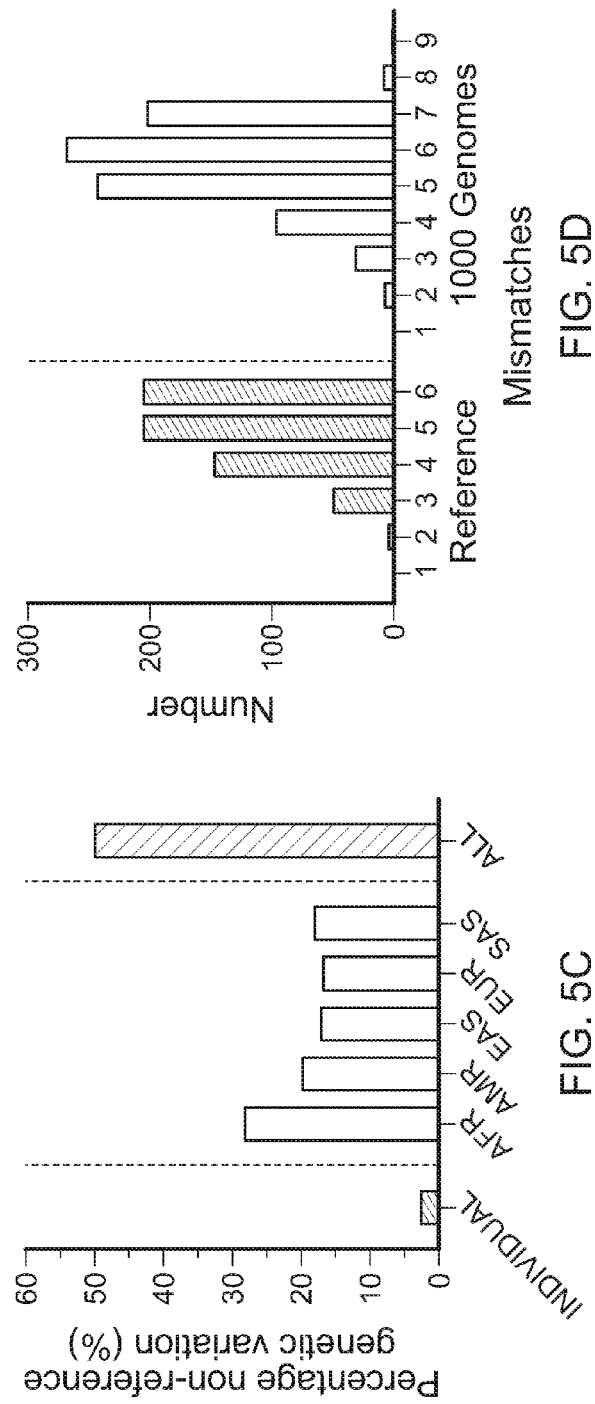

SEQUENCE LISTING

```
<160> NUMBER OF SEQ ID NOS: 136

<210> SEQ ID NO 1
<211> LENGTH: 30
<212> TYPE: DNA/RNA
<213> ORGANISM: Artificial Sequence
<220> FEATURE:
<223> OTHER INFORMATION: stem loop adapter sequence
<220> FEATURE:
<221> NAME/KEY: misc_feature
<222> LOCATION: (17)..(17)
<223> OTHER INFORMATION: can be U or ideoxyU
<220> FEATURE:
<221> NAME/KEY: misc_feature
<222> LOCATION: (29)..(30)
<223> OTHER INFORMATION: g and t are linked with a phosphorothioate
      linkage

<400> SEQUENCE: 1
cggtggaccg atgatcuatc ggtccaccgt                                       30

<210> SEQ ID NO 2
<211> LENGTH: 23
<212> TYPE: DNA
<213> ORGANISM: Artificial Sequence
<220> FEATURE:
<223> OTHER INFORMATION: EMX1 target site
<220> FEATURE:
<221> NAME/KEY: misc_feature
<222> LOCATION: (21)..(21)
<223> OTHER INFORMATION: n is a, c, g, or t

<400> SEQUENCE: 2
gagtccgagc agaagaagaa ngg                                              23

<210> SEQ ID NO 3
<211> LENGTH: 23
<212> TYPE: DNA
<213> ORGANISM: Artificial Sequence
<220> FEATURE:
<223> OTHER INFORMATION: FANCF Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 3
ggaatccctt ctgcagcacc ngg                                              23

<210> SEQ ID NO 4
```

```
<210> SEQ ID NO 4
<211> LENGTH: 23
<212> TYPE: DNA
<213> ORGANISM: Artificial Sequence
<220> FEATURE:
<223> OTHER INFORMATION: RNF2 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 4
gtcatcttag tcattacctg ngg                                              23

<210> SEQ ID NO 5
<211> LENGTH: 23
<212> TYPE: DNA
<213> ORGANISM: Artificial Sequence
<220> FEATURE:
<223> OTHER INFORMATION: Site_1 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 5
gggaaagacc cagcatccgt ngg                                              23

<210> SEQ ID NO 6
<211> LENGTH: 23
<212> TYPE: DNA
<213> ORGANISM: Artificial Sequence
<220> FEATURE:
<223> OTHER INFORMATION: Site_2 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 6
gaacacaaag catagactgc ngg                                              23

<210> SEQ ID NO 7
<211> LENGTH: 23
<212> TYPE: DNA
<213> ORGANISM: Artificial Sequence
<220> FEATURE:
<223> OTHER INFORMATION: Site_3 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 7
ggcccagact gagcacgtga ngg                                              23

<210> SEQ ID NO 8
<211> LENGTH: 23
<212> TYPE: DNA
<213> ORGANISM: Artificial Sequence
<220> FEATURE:
<223> OTHER INFORMATION: Site_4 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 8
ggcactgcgg ctggaggtgg ngg                                              23
```

-continued

```
<210> SEQ ID NO 9
<211> LENGTH: 23
<212> TYPE: DNA
<213> ORGANISM: Artificial Sequence
<220> FEATURE:
<223> OTHER INFORMATION: VEGFA_site_1 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 9 gggtggggggg agtttgctcc ngg                                             23

<210> SEQ ID NO 10
<211> LENGTH: 23
<212> TYPE: DNA
<213> ORGANISM: Artificial Sequence
<220> FEATURE:
<223> OTHER INFORMATION: VEGFA_site_2 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 10 gacccccctcc accccgcctc ngg                                             23

<210> SEQ ID NO 11
<211> LENGTH: 23
<212> TYPE: DNA
<213> ORGANISM: Artificial Sequence
<220> FEATURE:
<223> OTHER INFORMATION: VEGFA_site_3 Target Site Sequence
<220> FEATURE:
<221> NAME/KEY: misc_feature
<222> LOCATION: (21)..(21)
<223> OTHER INFORMATION: n is a, c, g, or t

<400> SEQUENCE: 11
ggtgagtgag tgtgtgcgtg ngg                                              23

<210> SEQ ID NO 12
<211> LENGTH: 23
<212> TYPE: DNA
<213> ORGANISM: Artificial Sequence
<220> FEATURE:
<223> OTHER INFORMATION: Off-target Sequence

<400> SEQUENCE: 12
gagtccgagc agaagaagaa ggg                                              23

<210> SEQ ID NO 13
<211> LENGTH: 23
<212> TYPE: DNA
<213> ORGANISM: Artificial Sequence
<220> FEATURE:
<223> OTHER INFORMATION: Off-target Sequence

<400> SEQUENCE: 13
aaggccaagc agaagagtaa tgg                                              23

<210> SEQ ID NO 14
<211> LENGTH: 23
<212> TYPE: DNA
<213> ORGANISM: Artificial Sequence
<220> FEATURE:
<223> OTHER INFORMATION: Off-target Sequence
```

```
<400> SEQUENCE: 14
gagtcctagc aggagaagaa gag                                          23

<210> SEQ ID NO 15
<211> LENGTH: 23
<212> TYPE: DNA
<213> ORGANISM: Artificial Sequence
<220> FEATURE:
<223> OTHER INFORMATION: Off-target Sequence

<400> SEQUENCE: 15
gaggccgagc agaagaaaga cgg                                          23

<210> SEQ ID NO 16
<211> LENGTH: 23
<212> TYPE: DNA
<213> ORGANISM: Artificial Sequence
<220> FEATURE:
<223> OTHER INFORMATION: Off-target Sequence

<400> SEQUENCE: 16
gaatccaagc aggagaagaa gga                                          23

<210> SEQ ID NO 17
<211> LENGTH: 23
<212> TYPE: DNA
<213> ORGANISM: Artificial Sequence
<220> FEATURE:
<223> OTHER INFORMATION: Off-target Sequence

<400> SEQUENCE: 17
tcatccaagc agaagaagaa gag                                          23

<210> SEQ ID NO 18
<211> LENGTH: 23
<212> TYPE: DNA
<213> ORGANISM: Artificial Sequence
<220> FEATURE:
<223> OTHER INFORMATION: Off-target Sequence

<400> SEQUENCE: 18
gagtctaagc aggagaataa agg                                          23

<210> SEQ ID NO 19
<211> LENGTH: 23
<212> TYPE: DNA
<213> ORGANISM: Artificial Sequence
<220> FEATURE:
<223> OTHER INFORMATION: Off-target Sequence

<400> SEQUENCE: 19
aagtccgagg agaggaagaa agg                                          23

<210> SEQ ID NO 20
<211> LENGTH: 23
<212> TYPE: DNA
<213> ORGANISM: Artificial Sequence
<220> FEATURE:
<223> OTHER INFORMATION: Off-target Sequence

<400> SEQUENCE: 20
gaagtagagc agaagaagaa gcg                                          23

<210> SEQ ID NO 21
<211> LENGTH: 23
```

```
<212> TYPE: DNA
<213> ORGANISM: Artificial Sequence
<220> FEATURE:
<223> OTHER INFORMATION: Off-target Sequence

<400> SEQUENCE: 21
gagcctgagc agaaggagaa ggg                                              23

<210> SEQ ID NO 22
<211> LENGTH: 23
<212> TYPE: DNA
<213> ORGANISM: Artificial Sequence
<220> FEATURE:
<223> OTHER INFORMATION: Off-target Sequence

<400> SEQUENCE: 22
aagcccgagc aaaggaagaa agg                                              23

<210> SEQ ID NO 23
<211> LENGTH: 23
<212> TYPE: DNA
<213> ORGANISM: Artificial Sequence
<220> FEATURE:
<223> OTHER INFORMATION: Off-target Sequence

<400> SEQUENCE: 23
aagtccatgc agaagaggaa ggg                                              23

<210> SEQ ID NO 24
<211> LENGTH: 23
<212> TYPE: DNA
<213> ORGANISM: Artificial Sequence
<220> FEATURE:
<223> OTHER INFORMATION: Off-target Sequence

<400> SEQUENCE: 24
gagttagagc agaagaagaa agg                                              23

<210> SEQ ID NO 25
<211> LENGTH: 23
<212> TYPE: DNA
<213> ORGANISM: Artificial Sequence
<220> FEATURE:
<223> OTHER INFORMATION: Off-target Sequence

<400> SEQUENCE: 25
tcttccaagc agaggaagaa agg                                              23

<210> SEQ ID NO 26
<211> LENGTH: 23
<212> TYPE: DNA
<213> ORGANISM: Artificial Sequence
<220> FEATURE:
<223> OTHER INFORMATION: Off-target Sequence

<400> SEQUENCE: 26
gagtacaagc agatgaaaaa cgg                                              23

<210> SEQ ID NO 27
<211> LENGTH: 23
<212> TYPE: DNA
<213> ORGANISM: Artificial Sequence
<220> FEATURE:
<223> OTHER INFORMATION: Off-target Sequence

<400> SEQUENCE: 27
```
gaggccaagc agaaaaaaaa tgg    23

<210> SEQ ID NO 28
<211> LENGTH: 23
<212> TYPE: DNA
<213> ORGANISM: Artificial Sequence
<220> FEATURE:
<223> OTHER INFORMATION: Off-target Sequence

<400> SEQUENCE: 28
gaagtagagc agaagaagaa gcg    23

<210> SEQ ID NO 29
<211> LENGTH: 23
<212> TYPE: DNA
<213> ORGANISM: Artificial Sequence
<220> FEATURE:
<223> OTHER INFORMATION: Off-target Sequence

<400> SEQUENCE: 29
aagtccagac agaagaagaa gga    23

<210> SEQ ID NO 30
<211> LENGTH: 23
<212> TYPE: DNA
<213> ORGANISM: Artificial Sequence
<220> FEATURE:
<223> OTHER INFORMATION: Off-target Sequence

<400> SEQUENCE: 30
aaatccaacc agaagaagaa agg    23

<210> SEQ ID NO 31
<211> LENGTH: 23
<212> TYPE: DNA
<213> ORGANISM: Artificial Sequence
<220> FEATURE:
<223> OTHER INFORMATION: Off-target Sequence

<400> SEQUENCE: 31
gagtctaagc agaagaagaa gag    23

<210> SEQ ID NO 32
<211> LENGTH: 23
<212> TYPE: DNA
<213> ORGANISM: Artificial Sequence
<220> FEATURE:
<223> OTHER INFORMATION: Off-target Sequence

<400> SEQUENCE: 32
aagtccgggc aaaagaggaa agg    23

<210> SEQ ID NO 33
<211> LENGTH: 23
<212> TYPE: DNA
<213> ORGANISM: Artificial Sequnece
<220> FEATURE:
<223> OTHER INFORMATION: Off-target Sequence

<400> SEQUENCE: 33
gaggccaagc agaaagaaaa agg    23

<210> SEQ ID NO 34
<211> LENGTH: 23
<212> TYPE: DNA
<213> ORGANISM: Artificial Sequence

```
<220> FEATURE:
<223> OTHER INFORMATION: Off-target Sequence

<400> SEQUENCE: 34
aggtcagagc agaagaaaag agg                                              23

<210> SEQ ID NO 35
<211> LENGTH: 23
<212> TYPE: DNA
<213> ORGANISM: Artificial Sequence
<220> FEATURE:
<223> OTHER INFORMATION: Off-target Sequence

<400> SEQUENCE: 35
gagtcccagc aaaagaagaa aag                                              23

<210> SEQ ID NO 36
<211> LENGTH: 23
<212> TYPE: DNA
<213> ORGANISM: Artificial Sequence
<220> FEATURE:
<223> OTHER INFORMATION: Off-target Sequence

<400> SEQUENCE: 36
cactccaagt agaagaagaa aag                                              23

<210> SEQ ID NO 37
<211> LENGTH: 23
<212> TYPE: DNA
<213> ORGANISM: Artificial Sequence
<220> FEATURE:
<223> OTHER INFORMATION: Off-target Sequence

<400> SEQUENCE: 37
atgtccaagc agaagaagtc tgg                                              23

<210> SEQ ID NO 38
<211> LENGTH: 23
<212> TYPE: DNA
<213> ORGANISM: Artificial Sequence
<220> FEATURE:
<223> OTHER INFORMATION: Off-target Sequence

<400> SEQUENCE: 38
aaggcagagc agaggaagag agg                                              23

<210> SEQ ID NO 39
<211> LENGTH: 23
<212> TYPE: DNA
<213> ORGANISM: Artificial Sequence
<220> FEATURE:
<223> OTHER INFORMATION: Off-target Sequence

<400> SEQUENCE: 39
aagtcccggc agaggaagaa ggg                                              23

<210> SEQ ID NO 40
<211> LENGTH: 23
<212> TYPE: DNA
<213> ORGANISM: Artificial Sequence
<220> FEATURE:
<223> OTHER INFORMATION: Off-target Sequence

<400> SEQUENCE: 40
ttctccaagc agaagaagaa gag                                              23
```

```
<210> SEQ ID NO 41
<211> LENGTH: 23
<212> TYPE: DNA
<213> ORGANISM: Artificial Sequence
<220> FEATURE:
<223> OTHER INFORMATION: Off-target Sequence

<400> SEQUENCE: 41
gaagtagagc agaagaagaa gcg                                              23

<210> SEQ ID NO 42
<211> LENGTH: 23
<212> TYPE: DNA
<213> ORGANISM: Artificial Sequence
<220> FEATURE:
<223> OTHER INFORMATION: Off-target Sequence

<400> SEQUENCE: 42
gagtccaagc agtagaggaa ggg                                              23

<210> SEQ ID NO 43
<211> LENGTH: 23
<212> TYPE: DNA
<213> ORGANISM: Artificial Sequence
<220> FEATURE:
<223> OTHER INFORMATION: Off-target Sequence

<400> SEQUENCE: 43
gagttagagc agaaaaaaaa tgg                                              23

<210> SEQ ID NO 44
<211> LENGTH: 23
<212> TYPE: DNA
<213> ORGANISM: Artificial Sequence
<220> FEATURE:
<223> OTHER INFORMATION: Off-target Sequence

<400> SEQUENCE: 44
gaatccaagc agaagaagag aag                                              23

<210> SEQ ID NO 45
<211> LENGTH: 23
<212> TYPE: DNA
<213> ORGANISM: Artificial Sequence
<220> FEATURE:
<223> OTHER INFORMATION: Off-target Sequence

<400> SEQUENCE: 45
agttccaagc agaggaagaa ggg                                              23

<210> SEQ ID NO 46
<211> LENGTH: 23
<212> TYPE: DNA
<213> ORGANISM: Artificial Sequence
<220> FEATURE:
<223> OTHER INFORMATION: Off-target Sequence

<400> SEQUENCE: 46
gagcacgagc aagagaagaa ggg                                              23

<210> SEQ ID NO 47
<211> LENGTH: 22
<212> TYPE: DNA
<213> ORGANISM: Artificial Sequence
<220> FEATURE:
<223> OTHER INFORMATION: Off-target Sequence
```

```
<400> SEQUENCE: 47
aagtcagaga gaagaagaag ag                                              22

<210> SEQ ID NO 48
<211> LENGTH: 23
<212> TYPE: DNA
<213> ORGANISM: Artificial Sequence
<220> FEATURE:
<223> OTHER INFORMATION: Off-target Sequence

<400> SEQUENCE: 48
cagtctgagt agaagaaaaa ggg                                             23

<210> SEQ ID NO 49
<211> LENGTH: 23
<212> TYPE: DNA
<213> ORGANISM: Artificial Sequence
<220> FEATURE:
<223> OTHER INFORMATION: Off-target Sequence

<400> SEQUENCE: 49
aagtctgagc acaagaagaa tgg                                             23

<210> SEQ ID NO 50
<211> LENGTH: 23
<212> TYPE: DNA
<213> ORGANISM: Artificial Sequence
<220> FEATURE:
<223> OTHER INFORMATION: Off-target Sequence

<400> SEQUENCE: 50
gagccggagc agaagaagga ggg                                             23

<210> SEQ ID NO 51
<211> LENGTH: 23
<212> TYPE: DNA
<213> ORGANISM: Artificial Sequence
<220> FEATURE:
<223> OTHER INFORMATION: Off-target Sequence

<400> SEQUENCE: 51
acgtctgagc agaagaagaa tgg                                             23

<210> SEQ ID NO 52
<211> LENGTH: 23
<212> TYPE: DNA
<213> ORGANISM: Artificial Sequence
<220> FEATURE:
<223> OTHER INFORMATION: Off-target Sequence

<400> SEQUENCE: 52
cgctccgagc agaagaaaag tgg                                             23

<210> SEQ ID NO 53
<211> LENGTH: 23
<212> TYPE: DNA
<213> ORGANISM: Artificial Sequence
<220> FEATURE:
<223> OTHER INFORMATION: Off-target Sequence

<400> SEQUENCE: 53
ccatccgagc aggagattaa tgg                                             23

<210> SEQ ID NO 54
```

```
<211> LENGTH: 23
<212> TYPE: DNA
<213> ORGANISM: Artificial Sequence
<220> FEATURE:
<223> OTHER INFORMATION: Off-target Sequence

<400> SEQUENCE: 54
gagcccaagc acaaaaagaa tgg                                              23

<210> SEQ ID NO 55
<211> LENGTH: 23
<212> TYPE: DNA
<213> ORGANISM: Artificial Sequence
<220> FEATURE:
<223> OTHER INFORMATION: Off-target Sequence

<400> SEQUENCE: 55
gagtaagaga agaagaagaa ggg                                              23

<210> SEQ ID NO 56
<211> LENGTH: 23
<212> TYPE: DNA
<213> ORGANISM: Artificial Sequence
<220> FEATURE:
<223> OTHER INFORMATION: Off-target Sequence

<400> SEQUENCE: 56
aagtcctagc agaaggaaag ggg                                              23

<210> SEQ ID NO 57
<211> LENGTH: 23
<212> TYPE: DNA
<213> ORGANISM: Artificial Sequence
<220> FEATURE:
<223> OTHER INFORMATION: Off-target Sequence

<400> SEQUENCE: 57
aagtccaggc aggagaaaaa tgg                                              23

<210> SEQ ID NO 58
<211> LENGTH: 23
<212> TYPE: DNA
<213> ORGANISM: Artificial Sequence
<220> FEATURE:
<223> OTHER INFORMATION: Off-target Sequence

<400> SEQUENCE: 58
aaggccgagc aggaggaaga agg                                              23

<210> SEQ ID NO 59
<211> LENGTH: 23
<212> TYPE: DNA
<213> ORGANISM: Artificial Sequence
<220> FEATURE:
<223> OTHER INFORMATION: Off-target Sequence

<400> SEQUENCE: 59
aagtctgaga agaagaagaa aga                                              23

<210> SEQ ID NO 60
<211> LENGTH: 23
<212> TYPE: DNA
<213> ORGANISM: Artificial Sequence
<220> FEATURE:
<223> OTHER INFORMATION: Off-target Sequence

<400> SEQUENCE: 60
```
tattccaagc aaaagaaaaa ggg                                          23

<210> SEQ ID NO 61
<211> LENGTH: 23
<212> TYPE: DNA
<213> ORGANISM: Artificial Sequence
<220> FEATURE:
<223> OTHER INFORMATION: Off-target Sequence

<400> SEQUENCE: 61
aagcccaagc agaagaaaaa tga                                          23

<210> SEQ ID NO 62
<211> LENGTH: 23
<212> TYPE: DNA
<213> ORGANISM: Artificial Sequence
<220> FEATURE:
<223> OTHER INFORMATION: Off-target Sequence

<400> SEQUENCE: 62
gagcccgtgc agaggaagaa gga                                          23

<210> SEQ ID NO 63
<211> LENGTH: 23
<212> TYPE: DNA
<213> ORGANISM: Artificial Sequence
<220> FEATURE:
<223> OTHER INFORMATION: Off-target Sequence

<400> SEQUENCE: 63
gagtccacac agaagaagaa aga                                          23

<210> SEQ ID NO 64
<211> LENGTH: 23
<212> TYPE: DNA
<213> ORGANISM: Artificial Sequence
<220> FEATURE:
<223> OTHER INFORMATION: Off-target Sequence

<400> SEQUENCE: 64
ctgtccaagc acaagaacaa tgg                                          23

<210> SEQ ID NO 65
<211> LENGTH: 23
<212> TYPE: DNA
<213> ORGANISM: Artificial Sequence
<220> FEATURE:
<223> OTHER INFORMATION: Off-target Sequence

<400> SEQUENCE: 65
gagtttgagt agaagaagaa gag                                          23

<210> SEQ ID NO 66
<211> LENGTH: 23
<212> TYPE: DNA
<213> ORGANISM: Artificial Sequence
<220> FEATURE:
<223> OTHER INFORMATION: Off-target Sequence

<400> SEQUENCE: 66
aggtctgagc agaagaaaga agg                                          23

<210> SEQ ID NO 67
<211> LENGTH: 23
<212> TYPE: DNA

```
<213> ORGANISM: Artificial Sequence
<220> FEATURE:
<223> OTHER INFORMATION: Off-target Sequence

<400> SEQUENCE: 67
atgtccaagc acaagaggaa tgg                                              23

<210> SEQ ID NO 68
<211> LENGTH: 23
<212> TYPE: DNA
<213> ORGANISM: Artificial Sequence
<220> FEATURE:
<223> OTHER INFORMATION: Off-target Sequence

<400> SEQUENCE: 68
gagcccaaga agaagaagaa gga                                              23

<210> SEQ ID NO 69
<211> LENGTH: 23
<212> TYPE: DNA
<213> ORGANISM: Artificial Sequence
<220> FEATURE:
<223> OTHER INFORMATION: Off-target Sequence

<400> SEQUENCE: 69
aagtctgagt aggagaaaaa ggg                                              23

<210> SEQ ID NO 70
<211> LENGTH: 23
<212> TYPE: DNA
<213> ORGANISM: Artificial Sequence
<220> FEATURE:
<223> OTHER INFORMATION: Off-target Sequence

<400> SEQUENCE: 70
aggtctgagc agaagaggaa gag                                              23

<210> SEQ ID NO 71
<211> LENGTH: 23
<212> TYPE: DNA
<213> ORGANISM: Artificial Sequence
<220> FEATURE:
<223> OTHER INFORMATION: Off-target Sequence

<400> SEQUENCE: 71
tgatccaagc aggagaaaaa tgg                                              23

<210> SEQ ID NO 72
<211> LENGTH: 23
<212> TYPE: DNA
<213> ORGANISM: Artificial Sequence
<220> FEATURE:
<223> OTHER INFORMATION: Off-target Sequence

<400> SEQUENCE: 72
cattcctagc agaggaagaa agg                                              23

<210> SEQ ID NO 73
<211> LENGTH: 23
<212> TYPE: DNA
<213> ORGANISM: Artificial Sequence
<220> FEATURE:
<223> OTHER INFORMATION: Off-target Sequence

<400> SEQUENCE: 73
taatccaatc agaagaagaa ggg                                              23
```

```
<210> SEQ ID NO 74
<211> LENGTH: 23
<212> TYPE: DNA
<213> ORGANISM: Artificial Sequence
<220> FEATURE:
<223> OTHER INFORMATION: Off-target Sequence

<400> SEQUENCE: 74
aaatccaacc agaagaagag ggg                                            23

<210> SEQ ID NO 75
<211> LENGTH: 23
<212> TYPE: DNA
<213> ORGANISM: Artificial Sequence
<220> FEATURE:
<223> OTHER INFORMATION: Off-target Sequence

<400> SEQUENCE: 75
caatcagagc agaggaagaa gag                                            23

<210> SEQ ID NO 76
<211> LENGTH: 23
<212> TYPE: DNA
<213> ORGANISM: Artificial Sequence
<220> FEATURE:
<223> OTHER INFORMATION: Off-target Sequence

<400> SEQUENCE: 76
gaagccaagc agaagaaaaa cag                                            23

<210> SEQ ID NO 77
<211> LENGTH: 23
<212> TYPE: DNA
<213> ORGANISM: Artificial Sequence
<220> FEATURE:
<223> OTHER INFORMATION: Off-target Sequence

<400> SEQUENCE: 77
gaggctgagc agaagaggaa gga                                            23

<210> SEQ ID NO 78
<211> LENGTH: 23
<212> TYPE: DNA
<213> ORGANISM: Artificial Sequence
<220> FEATURE:
<223> OTHER INFORMATION: Off-target Sequence

<400> SEQUENCE: 78
tgttccaagc agaagagtaa tgg                                            23

<210> SEQ ID NO 79
<211> LENGTH: 23
<212> TYPE: DNA
<213> ORGANISM: Artificial Sequence
<220> FEATURE:
<223> OTHER INFORMATION: Off-target Sequence

<400> SEQUENCE: 79
tagtctaagc agcagaagaa tgg                                            23

<210> SEQ ID NO 80
<211> LENGTH: 23
<212> TYPE: DNA
<213> ORGANISM: Artificial Sequence
<220> FEATURE:
```

```
<223> OTHER INFORMATION: Off-target Sequence

<400> SEQUENCE: 80
ccctccaagc agaagaagat gag                                              23

<210> SEQ ID NO 81
<211> LENGTH: 23
<212> TYPE: DNA
<213> ORGANISM: Artificial Sequence
<220> FEATURE:
<223> OTHER INFORMATION: Off-target Sequence

<400> SEQUENCE: 81
aggcccgagc aggagaaaat agg                                              23

<210> SEQ ID NO 82
<211> LENGTH: 23
<212> TYPE: DNA
<213> ORGANISM: Artificial Sequence
<220> FEATURE:
<223> OTHER INFORMATION: Off-target Sequence

<400> SEQUENCE: 82
agctccgagc agaggaagga ggg                                              23

<210> SEQ ID NO 83
<211> LENGTH: 23
<212> TYPE: DNA
<213> ORGANISM: Artificial Sequence
<220> FEATURE:
<223> OTHER INFORMATION: Off-target Sequence

<400> SEQUENCE: 83
gagtcagagc aaaagaagta gtg                                              23

<210> SEQ ID NO 84
<211> LENGTH: 23
<212> TYPE: DNA
<213> ORGANISM: Artificial Sequence
<220> FEATURE:
<223> OTHER INFORMATION: Off-target Sequence

<400> SEQUENCE: 84
gagtttaagc agaagaagag agg                                              23

<210> SEQ ID NO 85
<211> LENGTH: 23
<212> TYPE: DNA
<213> ORGANISM: Artificial Sequence
<220> FEATURE:
<223> OTHER INFORMATION: Off-target Sequence

<400> SEQUENCE: 85
tcttccaagc aaaagaagaa aga                                              23

<210> SEQ ID NO 86
<211> LENGTH: 23
<212> TYPE: DNA
<213> ORGANISM: Artificial Sequence
<220> FEATURE:
<223> OTHER INFORMATION: Off-target Sequence

<400> SEQUENCE: 86
gaggcccagc agaggaagaa gag                                              23
```

```
<210> SEQ ID NO 87
<211> LENGTH: 23
<212> TYPE: DNA
<213> ORGANISM: Artificial Sequence
<220> FEATURE:
<223> OTHER INFORMATION: Off-target Sequence

<400> SEQUENCE: 87
aagcccaagc aaatgaagaa tgg                                              23

<210> SEQ ID NO 88
<211> LENGTH: 23
<212> TYPE: DNA
<213> ORGANISM: Artificial Sequence
<220> FEATURE:
<223> OTHER INFORMATION: Off-target Sequence

<400> SEQUENCE: 88
tcttccgagc tgaagaagaa aag                                              23

<210> SEQ ID NO 89
<211> LENGTH: 23
<212> TYPE: DNA
<213> ORGANISM: Artificial Sequence
<220> FEATURE:
<223> OTHER INFORMATION: Off-target Sequence

<400> SEQUENCE: 89
gactccgagc agcagaagga tgg                                              23

<210> SEQ ID NO 90
<211> LENGTH: 23
<212> TYPE: DNA
<213> ORGANISM: Artificial Sequence
<220> FEATURE:
<223> OTHER INFORMATION: Off-target Sequence

<400> SEQUENCE: 90
gagaccaaac agaggaagaa ggg                                              23

<210> SEQ ID NO 91
<211> LENGTH: 23
<212> TYPE: DNA
<213> ORGANISM: Artificial Sequence
<220> FEATURE:
<223> OTHER INFORMATION: Off-target Sequence

<400> SEQUENCE: 91
gagtcctaga aaagaagag agg                                               23

<210> SEQ ID NO 92
<211> LENGTH: 23
<212> TYPE: DNA
<213> ORGANISM: Artificial Sequence
<220> FEATURE:
<223> OTHER INFORMATION: Off-target Sequence

<400> SEQUENCE: 92
gaatcagagc aaaaggagaa agg                                              23

<210> SEQ ID NO 93
<211> LENGTH: 23
<212> TYPE: DNA
<213> ORGANISM: Artificial Sequence
<220> FEATURE:
<223> OTHER INFORMATION: Off-target Sequence
```

```
<400> SEQUENCE: 93
ttatccgaga agaagaagta agg                                              23

<210> SEQ ID NO 94
<211> LENGTH: 23
<212> TYPE: DNA
<213> ORGANISM: Artificial Sequence
<220> FEATURE:
<223> OTHER INFORMATION: Off-target Sequence

<400> SEQUENCE: 94
aattccaagc agaagaaaaa gga                                              23

<210> SEQ ID NO 95
<211> LENGTH: 23
<212> TYPE: DNA
<213> ORGANISM: Artificial Sequence
<220> FEATURE:
<223> OTHER INFORMATION: Off-target Sequence

<400> SEQUENCE: 95
agttccaagc agaagaagca tgg                                              23

<210> SEQ ID NO 96
<211> LENGTH: 23
<212> TYPE: DNA
<213> ORGANISM: Artificial Sequence
<220> FEATURE:
<223> OTHER INFORMATION: Off-target Sequence

<400> SEQUENCE: 96
aagtccaagc acaagaaaca tgg                                              23

<210> SEQ ID NO 97
<211> LENGTH: 23
<212> TYPE: DNA
<213> ORGANISM: Artificial Sequence
<220> FEATURE:
<223> OTHER INFORMATION: Off-target Sequence

<400> SEQUENCE: 97
gagtcccagg agaagaagag agg                                              23

<210> SEQ ID NO 98
<211> LENGTH: 23
<212> TYPE: DNA
<213> ORGANISM: Artificial Sequence
<220> FEATURE:
<223> OTHER INFORMATION: Off-target Sequence

<400> SEQUENCE: 98
agttcagagc aggagaagaa tgg                                              23

<210> SEQ ID NO 99
<211> LENGTH: 23
<212> TYPE: DNA
<213> ORGANISM: Artificial Sequence
<220> FEATURE:
<223> OTHER INFORMATION: Off-target Sequence

<400> SEQUENCE: 99
aagcccgagc agaagaagtt gag                                              23

<210> SEQ ID NO 100
<211> LENGTH: 23
```

```
<212> TYPE: DNA
<213> ORGANISM: Artificial Sequence
<220> FEATURE:
<223> OTHER INFORMATION: Off-target Sequence

<400> SEQUENCE: 100
gagttagagc agaggaagag agg                                              23

<210> SEQ ID NO 101
<211> LENGTH: 23
<212> TYPE: DNA
<213> ORGANISM: Artificial Sequence
<220> FEATURE:
<223> OTHER INFORMATION: Off-target Sequence

<400> SEQUENCE: 101
cagtccaaac agaagaggaa tgg                                              23

<210> SEQ ID NO 102
<211> LENGTH: 23
<212> TYPE: DNA
<213> ORGANISM: Artificial Sequence
<220> FEATURE:
<223> OTHER INFORMATION: Off-target Sequence

<400> SEQUENCE: 102
gagtccggga aggagaagaa agg                                              23

<210> SEQ ID NO 103
<211> LENGTH: 23
<212> TYPE: DNA
<213> ORGANISM: Artificial Sequence
<220> FEATURE:
<223> OTHER INFORMATION: Off-target Sequence

<400> SEQUENCE: 103
aaggcaaagc aaaagaagag ggg                                              23

<210> SEQ ID NO 104
<211> LENGTH: 23
<212> TYPE: DNA
<213> ORGANISM: Artificial Sequence
<220> FEATURE:
<223> OTHER INFORMATION: Off-target Sequence

<400> SEQUENCE: 104
gaggtagagc agaagaagaa gcg                                              23

<210> SEQ ID NO 105
<211> LENGTH: 23
<212> TYPE: DNA
<213> ORGANISM: Artificial Sequence
<220> FEATURE:
<223> OTHER INFORMATION: Off-target Sequence

<400> SEQUENCE: 105
aagtcccagc aacagaagaa agg                                              23

<210> SEQ ID NO 106
<211> LENGTH: 23
<212> TYPE: DNA
<213> ORGANISM: Artificial Sequence
<220> FEATURE:
<223> OTHER INFORMATION: Off-target Sequence

<400> SEQUENCE: 106
```
gactcctagc aaaagaagaa tgg                                              23

<210> SEQ ID NO 107
<211> LENGTH: 23
<212> TYPE: DNA
<213> ORGANISM: Artificial Sequence
<220> FEATURE:
<223> OTHER INFORMATION: Off-target Sequence

<400> SEQUENCE: 107
gaggccttgc agaagaagaa ggc                                              23

<210> SEQ ID NO 108
<211> LENGTH: 23
<212> TYPE: DNA
<213> ORGANISM: Artificial Sequence
<220> FEATURE:
<223> OTHER INFORMATION: Off-target Sequence

<400> SEQUENCE: 108
gaatcccagc aggagaggaa tgg                                              23

<210> SEQ ID NO 109
<211> LENGTH: 23
<212> TYPE: DNA
<213> ORGANISM: Artificial Sequence
<220> FEATURE:
<223> OTHER INFORMATION: Off-target Sequence

<400> SEQUENCE: 109
caatccgggc agaagaagga gag                                              23

<210> SEQ ID NO 110
<211> LENGTH: 23
<212> TYPE: DNA
<213> ORGANISM: Artificial Sequence
<220> FEATURE:
<223> OTHER INFORMATION: Off-target Sequence

<400> SEQUENCE: 110
aagtccaaaa agaagaaaaa agg                                              23

<210> SEQ ID NO 111
<211> LENGTH: 23
<212> TYPE: DNA
<213> ORGANISM: Artificial Sequence
<220> FEATURE:
<223> OTHER INFORMATION: Off-target Sequence

<400> SEQUENCE: 111
taggctgagc agaagaaaaa gga                                              23

<210> SEQ ID NO 112
<211> LENGTH: 23
<212> TYPE: DNA
<213> ORGANISM: Artificial Sequence
<220> FEATURE:
<223> OTHER INFORMATION: Off-target Sequence

<400> SEQUENCE: 112
aagtctgaga agaagaagac atg                                              23

<210> SEQ ID NO 113
<211> LENGTH: 23
<212> TYPE: DNA
<213> ORGANISM: Artificial Sequence

```
<220> FEATURE:
<223> OTHER INFORMATION: Off-target Sequence

<400> SEQUENCE: 113
tagtcctagc aaaagcagaa ggg                                              23

<210> SEQ ID NO 114
<211> LENGTH: 22
<212> TYPE: DNA
<213> ORGANISM: Artificial Sequence
<220> FEATURE:
<223> OTHER INFORMATION: Off-target Sequence

<400> SEQUENCE: 114
gaatccaaga gaagaagaat gg                                               22

<210> SEQ ID NO 115
<211> LENGTH: 23
<212> TYPE: DNA
<213> ORGANISM: Artificial Sequence
<220> FEATURE:
<223> OTHER INFORMATION: Off-target Sequence

<400> SEQUENCE: 115
gagtctaagc agaagaggac tgg                                              23

<210> SEQ ID NO 116
<211> LENGTH: 23
<212> TYPE: DNA
<213> ORGANISM: Artificial Sequence
<220> FEATURE:
<223> OTHER INFORMATION: Off-target Sequence

<400> SEQUENCE: 116
gagtcccagc aggagaagaa aga                                              23

<210> SEQ ID NO 117
<211> LENGTH: 23
<212> TYPE: DNA
<213> ORGANISM: Artificial Sequence
<220> FEATURE:
<223> OTHER INFORMATION: Off-target Sequence

<400> SEQUENCE: 117
aagttggagc aggagaagaa ggg                                              23

<210> SEQ ID NO 118
<211> LENGTH: 23
<212> TYPE: DNA
<213> ORGANISM: Artificial Sequence
<220> FEATURE:
<223> OTHER INFORMATION: Off-target Sequence

<400> SEQUENCE: 118
gaagtggagc aggagaagaa ggg                                              23

<210> SEQ ID NO 119
<211> LENGTH: 23
<212> TYPE: DNA
<213> ORGANISM: Artificial Sequence
<220> FEATURE:
<223> OTHER INFORMATION: Off-target Sequence

<400> SEQUENCE: 119
gagtccatac aggagaagaa aga                                              23
```

<210> SEQ ID NO 120
<211> LENGTH: 22
<212> TYPE: DNA
<213> ORGANISM: Artificial Sequence
<220> FEATURE:
<223> OTHER INFORMATION: Off-target Sequence

<400> SEQUENCE: 120
gagtcgagaa gaagaaaaaa gg                                    22

<210> SEQ ID NO 121
<211> LENGTH: 23
<212> TYPE: DNA
<213> ORGANISM: Artificial Sequence
<220> FEATURE:
<223> OTHER INFORMATION: Off-target Sequence

<400> SEQUENCE: 121
gaatcccagc aggagaagac agg                                   23

<210> SEQ ID NO 122
<211> LENGTH: 23
<212> TYPE: DNA
<213> ORGANISM: Artificial Sequence
<220> FEATURE:
<223> OTHER INFORMATION: Off-target Sequence

<400> SEQUENCE: 122
gagtaggagc aggagaagaa gga                                   23

<210> SEQ ID NO 123
<211> LENGTH: 22
<212> TYPE: DNA
<213> ORGANISM: Artificial Sequence
<220> FEATURE:
<223> OTHER INFORMATION: Off-target Sequence

<400> SEQUENCE: 123
gagtagagca gaggaggaag gg                                    22

<210> SEQ ID NO 124
<211> LENGTH: 23
<212> TYPE: DNA
<213> ORGANISM: Artificial Sequence
<220> FEATURE:
<223> OTHER INFORMATION: Off-target Sequence

<400> SEQUENCE: 124
ctctccaagc agaagaagaa gaa                                   23

<210> SEQ ID NO 125
<211> LENGTH: 23
<212> TYPE: DNA
<213> ORGANISM: Artificial Sequence
<220> FEATURE:
<223> OTHER INFORMATION: Off-target Sequence

<400> SEQUENCE: 125
gaggccgggc aggagaagga ggg                                   23

<210> SEQ ID NO 126
<211> LENGTH: 23
<212> TYPE: DNA
<213> ORGANISM: Artificial Sequence
<220> FEATURE:
<223> OTHER INFORMATION: Off-target Sequence

<400> SEQUENCE: 126
gcatccaagc aggaggagaa ggg                                          23

<210> SEQ ID NO 127
<211> LENGTH: 23
<212> TYPE: DNA
<213> ORGANISM: Artificial Sequence
<220> FEATURE:
<223> OTHER INFORMATION: Off-target Sequence

<400> SEQUENCE: 127
aagcccaagg agaagaagaa agg                                          23

<210> SEQ ID NO 128
<211> LENGTH: 23
<212> TYPE: DNA
<213> ORGANISM: Artificial Sequence
<220> FEATURE:
<223> OTHER INFORMATION: Off-target Sequence

<400> SEQUENCE: 128
aagtcaaagc aggagaagaa aga                                          23

<210> SEQ ID NO 129
<211> LENGTH: 23
<212> TYPE: DNA
<213> ORGANISM: Artificial Sequence
<220> FEATURE:
<223> OTHER INFORMATION: Off-target Sequence

<400> SEQUENCE: 129
gagagagagc aaaaaaagaa ggg                                          23

<210> SEQ ID NO 130
<211> LENGTH: 23
<212> TYPE: DNA
<213> ORGANISM: Artificial Sequence
<220> FEATURE:
<223> OTHER INFORMATION: Off-target Sequence

<400> SEQUENCE: 130
aagcccgggc agaagaagca cag                                          23

<210> SEQ ID NO 131
<211> LENGTH: 23
<212> TYPE: DNA
<213> ORGANISM: Artificial Sequence
<220> FEATURE:
<223> OTHER INFORMATION: Off-target Sequence

<400> SEQUENCE: 131
gtgtcagagc agaaaaagag tgg                                          23

<210> SEQ ID NO 132
<211> LENGTH: 23
<212> TYPE: DNA
<213> ORGANISM: Artificial Sequence
<220> FEATURE:
<223> OTHER INFORMATION: Off-target Sequence

<400> SEQUENCE: 132
cattccaagc agcagaagaa gag                                          23

<210> SEQ ID NO 133

```
<211> LENGTH: 23
<212> TYPE: DNA
<213> ORGANISM: Artificial Sequence
<220> FEATURE:
<223> OTHER INFORMATION: Off-target Sequence

<400> SEQUENCE: 133
aagtccaagc ataagaaaac agg                                          23

<210> SEQ ID NO 134
<211> LENGTH: 23
<212> TYPE: DNA
<213> ORGANISM: Artificial Sequence
<220> FEATURE:
<223> OTHER INFORMATION: Off-target Sequence

<400> SEQUENCE: 134
gagagagagc aggagaggaa agg                                          23

<210> SEQ ID NO 135
<211> LENGTH: 23
<212> TYPE: DNA
<213> ORGANISM: Artificial Sequence
<220> FEATURE:
<223> OTHER INFORMATION: Off-target Sequence

<400> SEQUENCE: 135
gagtcagagc agaagaaaga gga                                          23

<210> SEQ ID NO 136
<211> LENGTH: 23
<212> TYPE: DNA
<213> ORGANISM: Artificial Sequence
<220> FEATURE:
<223> OTHER INFORMATION: Off-target Sequence

<400> SEQUENCE: 136
atctccaagc agaagaaaaa tgg                                          23
```

COMPREHENSIVE IN VITRO REPORTING OF CLEAVAGE EVENTS BY SEQUENCING (CIRCLE-SEQ)

CLAIM OF PRIORITY

This application claims the benefit of U.S. Patent Application Ser. No. 62/235,154, filed on Sep. 30, 2015. The entire contents of the foregoing are hereby incorporated by reference.

FEDERALLY SPONSORED RESEARCH OR DEVELOPMENT

This invention was made with Government support under Grant No. DP1 GM105378 awarded by the National Institutes of Health. The Government has certain rights in the invention.

TECHNICAL FIELD

Described herein are in vitro methods for defining the genome-wide cleavage specificities of engineered nucleases such as CRISPR-Cas9 Nucleases.

BACKGROUND

Engineered nuclease technology including zinc fingers, TALENs, and CRISPR-Cas9 nucleases, is revolutionizing biomedical research and providing important new modalities for therapy of gene-based diseases. Sensitive detection of off-target effects is important for translating these methods into human therapeutics. In vitro biochemical methods for finding off-targets offer potential advantages of greater reproducibility and scalability while avoiding limitations associated with strategies that require the culture and manipulation of living cells.

SUMMARY

At least in part, the present invention is based on the development of sensitive, unbiased methods for genome-wide detection of potential engineered nuclease (e.g., CRISPR-Cas9) off-target cleavage sites from cell type-specific genomic DNA samples. The present methods use exonuclease selection of covalently closed DNA molecules to create a population of genomic DNA molecules with very few free DNA ends, as a starting population for cleavage-specific enrichment and sequencing. Enrichment of these cleaved fragments, estimated to be >500,000× from human genomic DNA, enables very sequencing-efficient discovery of in vitro cleaved DNA fragments, in contrast to methods such as Digenome-Seq (Kim et al., Nat Methods. 2015 March; 12(3):237-43) that rely on whole-genome sequencing and that have much higher background. After optimization, the present in vitro assay detected 100% of off-target cleavage sites detected by the in-cell GUIDE-seq assay at the VEGFA site 1 and EMX1 target sites performed in human U2OS cells and described in Tsai et al., Nat Biotechnol. 2015 February; 33(2):187-97 as well as additional new off-target sites not found by the GUIDE-seq experiments (in other words, the present in vitro assay detects a superset of GUIDE-seq detected cleavage sites).

Described herein are methods of enzymatically preparing a library of covalently closed fully circularized DNA fragments with minimized numbers of DNA double-stranded breaks (DSBs) by ligation of stem-loop or hairpin adapters, exonuclease selection, enzymatic opening of the stem-loop and repair of ends, and intramolecular ligation. These circles can then be manipulated to detect nuclease-induced cleavage of this enzymatically purified library of covalently closed fully circularized DNA fragments by sequencing. Together, these two methods comprise a strategy for efficiently mining for nuclease-induced cleavage sites in complex mixtures of DNA. Thus, the methods can include creating a population of DNA molecules without ends, treating that population with a nuclease, and finding DNA molecules in this population that have newly created ends as a result of nuclease-induced cleavage.

Thus, provided herein are methods for preparing a library of covalently closed circular double-stranded DNA fragments. The methods can include providing dsDNA, e.g., genomic DNA (gDNA) from a cell type or organism of interest or synthetic DNA; randomly shearing the DNA to a defined average length, e.g., an average length of about 200-500 bps, e.g., about 300 bps, to provide a population of DNA fragments; optionally preparing the fragments for end-ligation, e.g., by end-repairing and/or A-tailing the sheared DNA; ligating to the ends of the fragments a stem-loop adapter comprising at least a single deoxyuridine adjacent to or within a loop sequence comprising a palindromic sequence, to prepare a population of ligated linear dsDNA fragments; contacting the library with an exonuclease (e.g., a cocktail such as Lambda exonuclease and/or E. coli Exonuclease I) to degrade any remaining linear fragments with unligated ends, to produce a purified population of ligated linear dsDNA fragments; contacting the library with enzymes that nick the ligated dsDNA fragments at the deoxyuridine and to remove a 3' terminal phosphate, e.g., with uracil DNA glycosylase (UDG) and/or endonuclease VIII, a DNA glycosylase-lyase, to nick the DNA at the deoxyuridine and T4 Polynucleotide Kinase to remove a 3' terminal phosphate; incubating the nicked linear dsDNA fragments under conditions sufficient to promote intramolecular ligation and formation of circular DNA molecules; and purifying the ligated fragments using an exonuclease, thereby preparing a library of covalently closed fully circular double-stranded DNA fragments.

In some embodiments, the methods include contacting the library of covalently closed fully circular dsDNA fragments with a nuclease (e.g., an engineered nuclease as described herein) to induce site-specific cleavage; optionally preparing the cleaved fragments for end-ligation, e.g., by end-repairing and/or A-tailing the sheared DNA ligating a sequencing adapter comprising at least (and preferably only) a single deoxyuridine and a primer site compatible for use in PCR priming and/or sequencing at the cleavage site; contacting the library with an enzyme, e.g., uracil DNA glycosylase (UDG) and/or endonuclease VIII, a DNA glycosylase-lyase, that nicks at the deoxyuridine; and sequencing those fragments using the sequencing adapter.

Also provided herein are methods for preparing a library of fragments comprising nuclease-induced double stranded breaks in dsDNA, e.g., genomic DNA (gDNA). The methods can include providing dsDNA, e.g., gDNA from a cell type or organism of interest; randomly shearing the dsDNA to a defined average length, e.g., an average length of about 200-500 bps, e.g., about 300 bps; optionally end-repairing and/or A-tailing the sheared DNA; ligating a first stem-loop adapter, preferably comprising a first region, e.g., of about 10-15, e.g., about 12 nucleotides; a second region preferably of about 5 nucleotides, that forms one or more loops and comprises a single deoxyuridine nucleotide adjacent to a palindromic sequence for intramolecular ligation; and a third region that is complementary to the first region with one additional nucleotide, e.g., about 13 nucleotides; contacting the library with uracil DNA glycosylase (UDG) and/or endonuclease VIII, a DNA glycosylase-lyase, to nick the dsDNA at the deoxyuridine and T4 Polynucleotide Kinase to remove a terminal 3' phosphate that is molecularly incompatible with ligation; incubating the nicked dsDNA under conditions sufficient to promote intramolecular ligation and formation of a sample comprising circular dsDNA molecules; contacting the sample with one or more exonucleases (e.g., bacteriophage lambda exonuclease, E. coli ExoI, PlasmidSafe™ ATP-dependent exonuclease), sufficient to degrade any dsDNA molecules that are not circular; treating the sample with a nuclease to induce site-specific cleavage (e.g., of on- and/or off-target sites, e.g., to induce blunt or staggered/overhanging ends) optionally end-repairing and then A-tailing the resulting ends; ligating a sequencing adapter comprising a first region of about 12 nucleotides; a second region of about 40 nucleotides that forms a loop, e.g., one or more hairpin loops, and comprises a second primer compatible for use in PCR priming and/or sequencing, e.g., next generation sequencing (NGS); and a third region of about 13 nucleotides (e.g., one longer than the first region) that is complementary to the first region; and a single deoxyuridine nucleotide between the second and third regions, to create a population wherein the DNA fragments that were cleaved by the nuclease have a sequencing adapter ligated to the ends; thereby preparing a library of fragments enriched for nuclease-cleaved adapter-ligated fragments, e.g., wherein each end was created by a nuclease-induced double stranded break in the dsDNA and then ligated with an adapter.

In some embodiments, the methods include contacting the library with uracil DNA glycosylase (UDG) and/or endonuclease VIII, a DNA glycosylase-lyase to nick the DNA at the deoxyuridine; and sequencing those fragments bearing a sequencing adapter.

In some embodiments, the exonuclease used to degrade any remaining linear fragments with unligated ends is a cocktail of nucleases comprising one or more of bacteriophage Lambda exonuclease, E. coli Exonuclease I, and an ATP-dependent exonuclease.

In some embodiments, the engineered nuclease is selected from the group consisting of meganucleases, MegaTALs, zinc-finger nucleases, transcription activator effector-like nucleases (TALEN), Clustered Regularly Interspaced Short Palindromic Repeats (CRISPR)/Cas RNA-guided nucleases (CRISPR/Cas RGNs), and FokI-dCas9 fusion proteins.

In some embodiments of the methods described herein, treating the sample with a nuclease to induce site-specific cleavage, e.g., at on- and off-target sites, comprises contacting the sample with a Cas9 nuclease complexed with a specific guide RNA (gRNA).

In some embodiments, the primer site in the hairpin comprises a next generation sequencing primer site, a randomized DNA barcode or unique molecular identifier (UMI).

In some embodiments, the methods include contacting the library with uracil DNA glycosylase (UDG) and/or endonuclease VIII, a DNA glycosylase-lyase to nick the DNA at the deoxyuridine; and sequencing those fragments bearing a first and a second hairpin adapter.

In some embodiments, the engineered nuclease is selected from the group consisting of meganucleases, MegaTALs, zinc-finger nucleases, transcription activator effector-like nucleases (TALEN), Clustered Regularly Interspaced Short Palindromic Repeats (CRISPR)/Cas RNA-guided nucleases (CRISPR/Cas RGNs), and FokI-dCas9 fusions (RNA-guided FokI nuclease).

In some embodiments, treating the sample with a nuclease to induce site-specific cleavage, e.g., at on- and off-target sites, comprises contacting the sample with a Cas9 nuclease complexed with a specific guide RNA (gRNA).

In some embodiments, the DNA is isolated from a mammalian, plant, bacterial, or fungal cell (e.g., gDNA).

In some embodiments, the DNA is synthetic.

In some embodiments, the engineered nuclease is a TALEN, zinc finger, meganuclease, megaTAL, FokI-dCas9 fusion or a Cas9 nuclease or Cpf1 nuclease, e.g., wild type or a variant thereof.

In some embodiments, wherein the engineered nuclease is a Cas9 nuclease, the method also includes utilizing a guide RNA that directs the Cas9 nuclease to a target sequence in the genome. In some embodiments, the engineered nuclease is a Cas9 nuclease, and the method also includes expressing in the cells a guide RNA that directs the Cas9 nuclease to a target sequence in the genome.

In some embodiments, the primer site in the hairpin comprises a next generation sequencing primer site, a randomized DNA barcode or unique molecular identifier (UMI).

The present methods have several advantages over previously described approaches for finding off-target sites of engineered nucleases. For example, the present methods are in vitro; in contrast, cell-based methods (such as GUIDE-seq (see WO 2015/200378 and Tsai et al., Nature Biotechnology 33:187-197 (2015)) require the introduction of double stranded oligodeoxynucleotides (dsODN) as well as expression or introduction of nuclease or nuclease-encoding components into cells. Not all cells will allow the introduction of dsODNs and/or nuclease or nuclease-encoding components, and these reagents can be toxic in some cases. If a cell type of particular interest is not amenable to introduction of dsODNs, nucleases, or nuclease-encoding components, a surrogate cell type might be used, but cell-specific effects might not be detected. The present methods do not require delivery of dsODNs, nucleases, or nuclease-encoding components into a cell, are not influenced by chromatin state, do not create toxicity issues, do not require growth and propagation of a cell line, and enable interrogation of specific cellular genomes by cleavage of genomic DNA that is obtained from the cell-type of interest. Furthermore, because the exonuclease has activity against double-stranded linear DNA but essentially none against circular DNA, the background is very low providing a very high signal to noise ratio.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 4A-G. CIRCLE-seq detected off-target cleavage sites can also be cleaved in human cells. (A) Stem-leaf plot of CIRCLE-seq read counts for 10 gRNAs previously analyzed by GUIDE-seq. The on-target and off-target sites are shown. (B) Schematic overview of the targeted tag sequencing approach. Primers are designed to amplify genomic regions flanking nuclease-induced DSBs from genomic DNA of cells treated with nuclease and double-stranded oligodeoxynucleotide (dsODN) tag. (c-d) Targeted tag integration frequencies at control off-target sites detected by both CIRCLE-seq and GUIDE-seq (upper part of panel) and off-target sites detected by CIRCLE-seq but not GUIDE-seq) for gRNAs targeted to EMX1 and VEGFA site 1. Off-target sites are ordered top to bottom by CIRCLE-seq read count with mismatches to the intended target sequence indicated. Observed tag integration frequencies observed for control and nuclease-treated cells are plotted on a log scale. (E) Pie charts showing fractions of CIRCLE-seq sites analyzed that are also detected by targeted tag sequencing. (F) Plots of integration positions observed by targeted tag sequencing. PAM bases are the last three nucleotides from the right. Integrations occur at positions proximal to the location of the predicted DSB (three base pairs away the PAM). (G) Percentage of unique cleavage sites that can be found using a reference-independent site discovery algorithm, for CIRCLE-seq experiments performed with gRNAs targeting non-repetitive sites in HEK293, K562, and U2OS genomic DNA.

FIGS. 5A-E. Using CIRCLE-seq to assess the impacts of personalized SNPs on off-target site analysis. (A) Scatterplots of CIRCLE-seq read counts from experiments performed on genomic DNA from two different cell types. Sites with non-reference genetic variation in only one cell type are black, while those with non-reference variation in both cell types are shaded. (B) Examples of allele-specific CIRCLE-seq read counts at off-target sites with non-reference genetic variation. Mismatches to the intended target sequence are indicated with colored nucleotides, while matching bases are indicated with a dot. The base position harboring the differential genetic change between cell types is indicated with a small arrow. (C) Proportion of CIRCLE-seq off-target sites where non-reference genetic variation was identified in genotyped individuals from the 1000 Genomes Project: African (AFR), Ad Mixed American (AMR), East Asian (EAS), European (EUR), and Southeast Asian (SAS) super-populations, and a combined population average. (D) Histogram showing distribution of CIRCLE-seq off-target sites by numbers of mismatches in reference human genome sequence (striped bars) and in 1000 Genomes Project data-derived off-target site haplotypes (white bars). (E) Proportion of 1000 Genomes Project-derived haplotypes with increased, decreased, or the same numbers of mismatches in off-target sites identified by CIRCLE-seq.

DETAILED DESCRIPTION

Figures 1A, 1B:
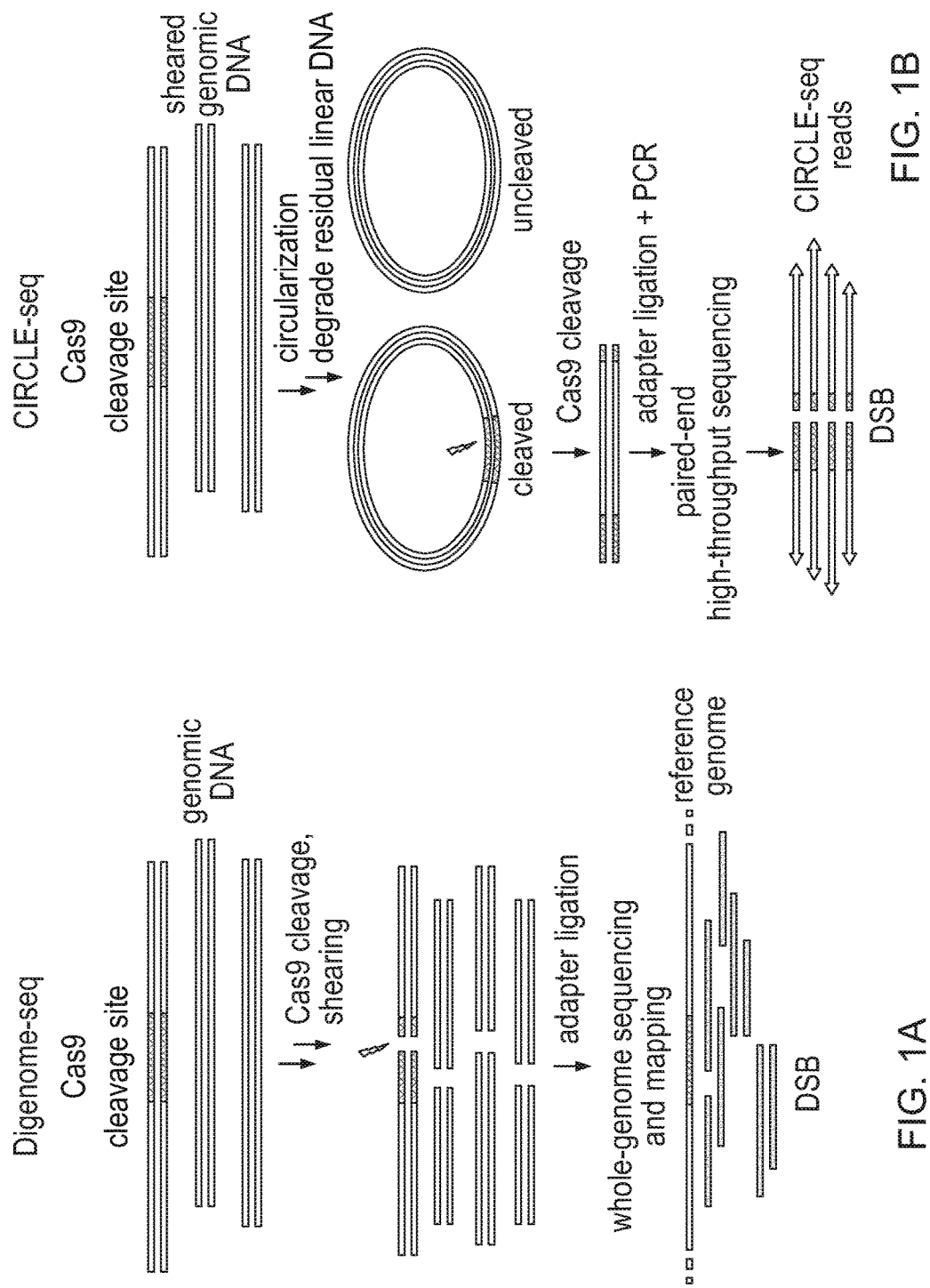
FIGS. 1A-D. Overview of in vitro Digenome-seq and CIRCLE-seq methods for genome-wide detection of CRISPR-Cas9 nuclease off-target cleavage. (A) Schematic overview of the digested genome sequencing (Digenome-seq) method. Genomic DNA is cleaved with Cas9 nuclease in vitro, purified, sheared, and then ligated to adapters for whole genome sequencing. Candidate off-target sites with an enrichment of uniform start mapping positions are identified by a scoring algorithm. (B) Schematic overview of the circularization for in vitro reporting of cleavage effects by sequencing (CIRCLE-seq) method. Genomic DNA is sheared and circularized and undesired linear DNA molecules are degraded away by exonuclease treatment. Circular DNA molecules containing a Cas9 cleavage site (shaded) can be linearized with Cas9, releasing those DNA ends for adapter ligation, PCR amplification, and paired-end high-throughput sequencing. Note how each pair of reads generated by Cas9 cleavage contains complete sequence information for a single off-target site. (C) Detailed schematic overview of exemplary CIRCLE-seq method. Genomic DNA is randomly sheared to an average of ~300 bp, end-repaired, A-tailed, and ligated to uracil-containing stem-loop adapters. Covalently closed DNA molecules with stem-loop adapters ligated to both ends are selected for by treatment with a mixture of Lambda exonuclease and E. coli Exonuclease I. 4 bp overhangs are released with a mixture of USER enzyme and T4 PNK, and DNA molecules are circularized at low concentrations favoring intramolecular ligation. Unwanted linear DNA is degraded with Plasmid-Safe ATP-dependent DNase. Circular DNA is treated with Cas9-gRNA complex and cleaved, linearized DNA is ligated to sequencing adapters and amplified for high throughput sequencing. (D) CIRCLE-seq read counts were highly reproducible between independent CIRCLE-seq experiments. Scatterplots of CIRCLE-seq read counts between two independent CIRCLE-seq libraries prepared from the same source of genomic DNA (human U2OS cells). CIRCLE-seq read counts were strongly correlated.

Engineered genome-editing nucleases are transformative technologies for both scientific research and human medicine. An important issue with the use of this technology is the extent to which off-target cleavage events occur at unintended target sites in the genome of a living cell.[10,24-27] This is significant particularly because, in nearly all cell types, repair of nuclease-induced breaks by non-homologous end-joining can lead to the efficient introduction of insertion or deletion mutations (indels). For both research and therapeutic applications, in which millions to billions of cells may be treated with these nucleases, even low-frequency mutations may lead to unwanted cellular phenotypes or undesired clinical consequences.

A number of genome-wide approaches have recently been developed to define the landscape of off-target cleavage events induced by genome-editing nucleases. For example, various cell-based methods for genome-wide detection of such mutations have been described.[28-32] These include Genome-wide Unbiased Identification of DSBs enabled by sequencing (GUIDE-seq) and High-throughput, Genome-wide Translocation Sequencing (HTGTS). For example, the GUIDE-seq method, which relies on uptake of a short double-stranded oligonucleotide "tag" into nuclease-induced DSBs in living cells, has been shown to define off-target sites on a genome-wide scale, identifying sites that are mutagenized with frequencies as low as 0.1% of the time in a population of cells (Tsai et al., Nat Biotechnol. 2015). Other cell-based methods for defining nuclease-induced off-target breaks include a method that maps translocation fusions to the on-target site and another that relies on uptake of integration-deficient lentivirus (IDLV) genomes into sites of DSBs. However, the requirements of these methods for efficient manipulation of cells can limit their feasibility, scalability, and reproducibility, particularly when working with more challenging non-transformed cell types that would be most relevant and useful for therapeutics.

Despite this recent progress, cell-based methods for off-target determination have a number of limitations including: (1) a requirement to be able to introduce both the nuclease components and a tag such as the dsODN or IDLV genome into cells; (2) biological selection pressures that might favor or disfavor the growth of cells harboring certain types of off-target mutations; (3) the potential confounding effects of cell-type-specific parameters such as chromatin, DNA methylation, gene expression, and nuclear architecture on nuclease off-target activities/effects; and/or (4) the requirement to be able to grow the cells of interest in culture.

In vitro methods using purified genomic DNA provide an attractive alternative because they would sidestep these various limitations of cell-based approaches. (Note that in this description, in vitro refers to experiments performed with purified components in cell-free reactions). In vitro methods for detecting off-target cleavage sites have potential advantages over cell-based methods that can include: a) they are not affected by chromatin context, gene expression levels, or intra-nuclear localization because they are performed on purified protein-free DNA, b) they do not depend on error-prone cellular DNA repair for detection of sites, which can be influenced by the factors listed in a) as well as by sequence-dependent effects, and c) they offer the potential to be highly sensitive for detection of low frequency cleavage events because the concentrations of nuclease, genomic DNA, and length of time for cleavage can all be varied. Biochemical assays using defined and purified components improve reproducibility, bypass the need for efficient cell transduction or transfection, and avoid potential biases caused by positive or negative effects on cell fitness. Importantly, the concentrations of active nuclease and genomic DNA can be raised to very high levels in vitro, potentially enabling identification of sequences that may be cleaved at very rare frequencies in cells and/or at the highest concentrations of nucleases that can be expressed in cells. An in vitro method for characterizing Cas9 cleavage specificity of partially degenerate DNA libraries biased towards specific target DNA sites has been previously described but when used with Cas9 nuclease and various gRNAs, most of the sites identified did not actually occur in the human genome[33].

However, in vitro methods face the challenge that isolated genomic DNA is by experimental necessity randomly sheared (or broken) into smaller pieces. This poses a challenge because it is not easy to differentially identify DSBs induced by shearing from DSBs induced by treatment of the genomic DNA in vitro with nucleases. To date, only a single in vitro genome-wide off-target identification method, known as Digenome-seq[34], has been described for use with human genomic DNA. This approach relies on nuclease cleavage of bulk genomic DNA, ligation of sequencing adapters to all free ends (nuclease- and non-nuclease-induced), high-throughput sequencing, and bioinformatic identification of nuclease-cleaved sites with signature uniform mapping ends. However, the extremely high background of randomly sheared genomic DNA fragments sequenced with Digenome-seq makes it exceedingly challenging to identify lower frequency nuclease-induced cleavage events and requires access to HiSeq or HiSeq X10 machines used for production-scale human genome resequencing that can generate the required number of reads (>400 million).

The Digenome-seq method suffers from a high background of sequencing reads that are uninformative about nuclease off-target activity, making it inefficient with respect to sequencing resources and therefore less sensitive in its ability to detect off-target sites. With Digenome-seq, randomly sheared genomic DNA is subjected to digestion by an engineered nuclease and then these fragments are subjected to whole genome re-sequencing. Randomly sheared fragments will align randomly to the genome, whereas those fragments that have been digested by the nuclease will have uniform ends that when mapped back to the genome will line up at the same genomic base position. An initial validation of this method showed that it had some ability to detect off-target cleavage sites for CRISPR-Cas9 nucleases. However, with Digenome-seq, less than 1 in every million sequencing reads are mapped to a nuclease off-target site. This high background causes several disadvantages for the method: (A) it makes the method extremely cost-ineffective with respect to sequencing, requiring the use of methods such as the HiSeq or HiSeqx10 platform; (B) the high background of randomly broken DNA fragments that map to the genome make it challenging to identify low frequency nuclease-induced breaks, a signal-to-noise problem; and (C) the low yield of information makes it challenging to find low frequency nuclease off-target sites even with the large number of sequencing reads that can be obtained with state of the art methods such as the HiSeqx10 platform. Indeed, Digenome failed to identify a number of off-target sites found by GUIDE-seq for a particular gRNA (although the caveat must be added that the two experiments were performed with genomic DNA from different cell lines).

Described herein is an in vitro method that enables comprehensive determination of DSBs induced by nucleases on any genomic DNA of interest. This method enables enrichment of nuclease-induced DSBs over random DSBs induced by shearing of genomic DNA.

Figure 3A:
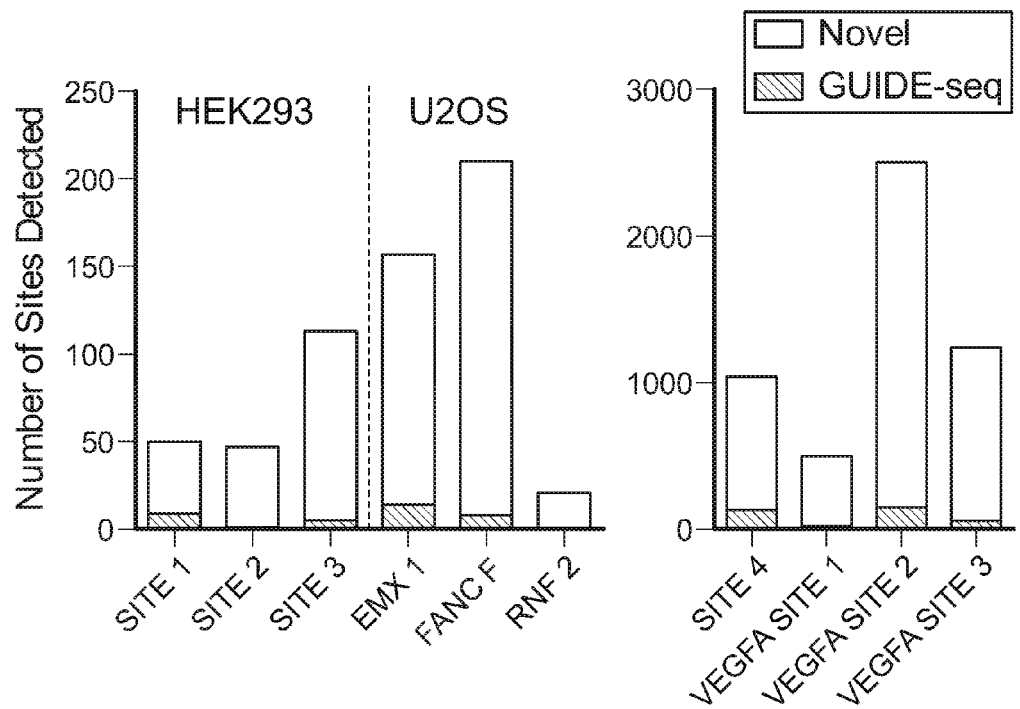
FIGS. 3A-E. Comparisons of CIRCLE-seq with cell-based GUIDE-seq and HTGTS methods. (A) Histogram showing the number of sites identified exclusively by CIRCLE-seq (white bars) and by both CIRCLE-seq and GUIDE-seq (shaded bars) (B) Manhattan plots of CIRCLE-seq detected off-target sites, with bar heights representing CIRCLE-seq read count (normalized to site with highest read count) and organized by chromosomal position. (C) Venn diagrams showing intersection of CIRCLE-seq and GUIDE-seq detected genomic off-target cleavage sites. (D) Histogram showing the number of sites detected exclusively by CIRCLE-seq or by both CIRCLE-seq and HTGTS. (E) Venn diagrams showing overlap between sets of off-target cleavage sites detected between CIRCLE-seq, GUIDE-seq, and HTGTS. CIRCLE-seq detects virtually all off-target cleavage sites detected by both GUIDE-seq and HTGT).
Figures 1, 3B:
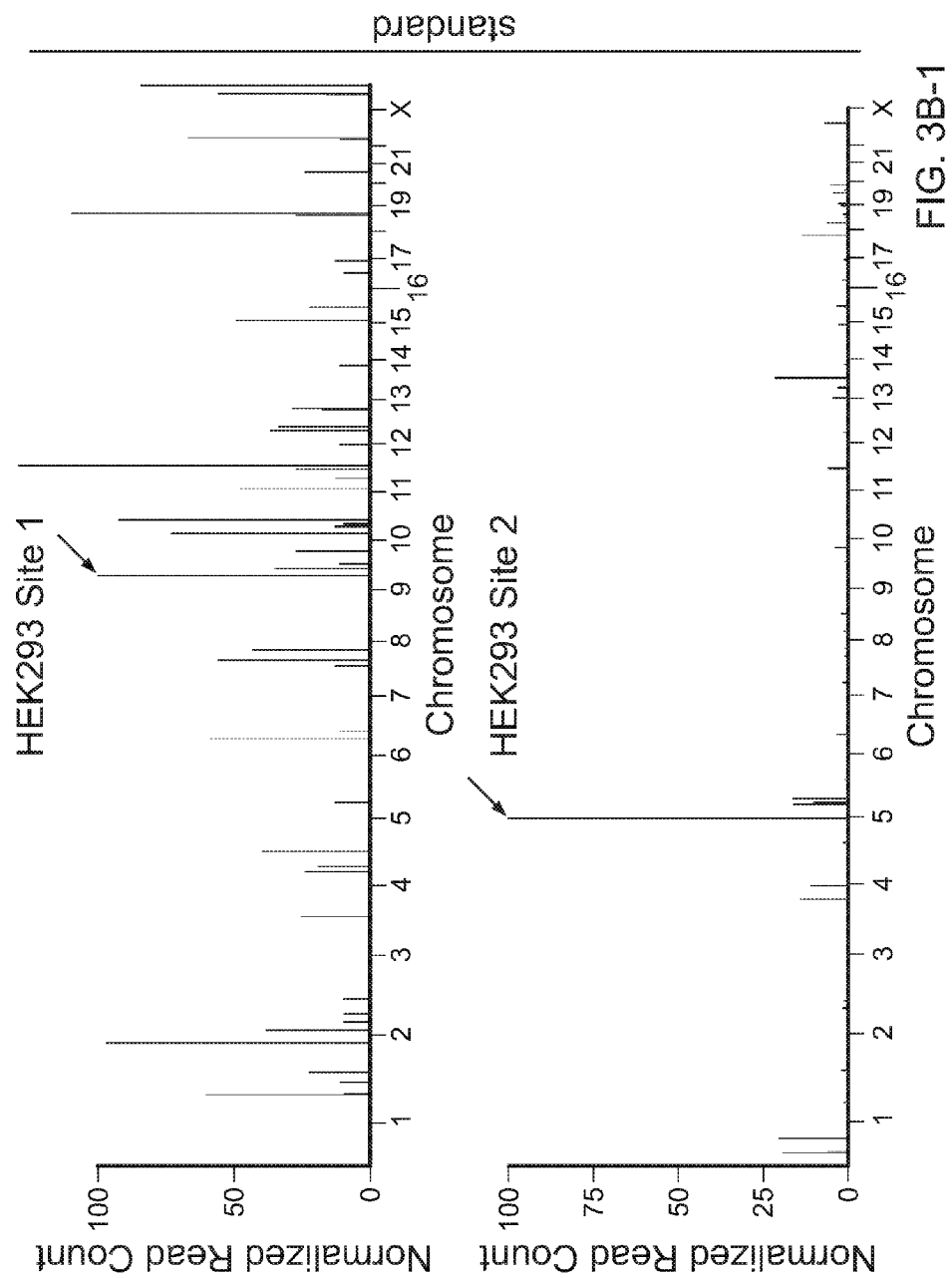
Figures 2, 3B:
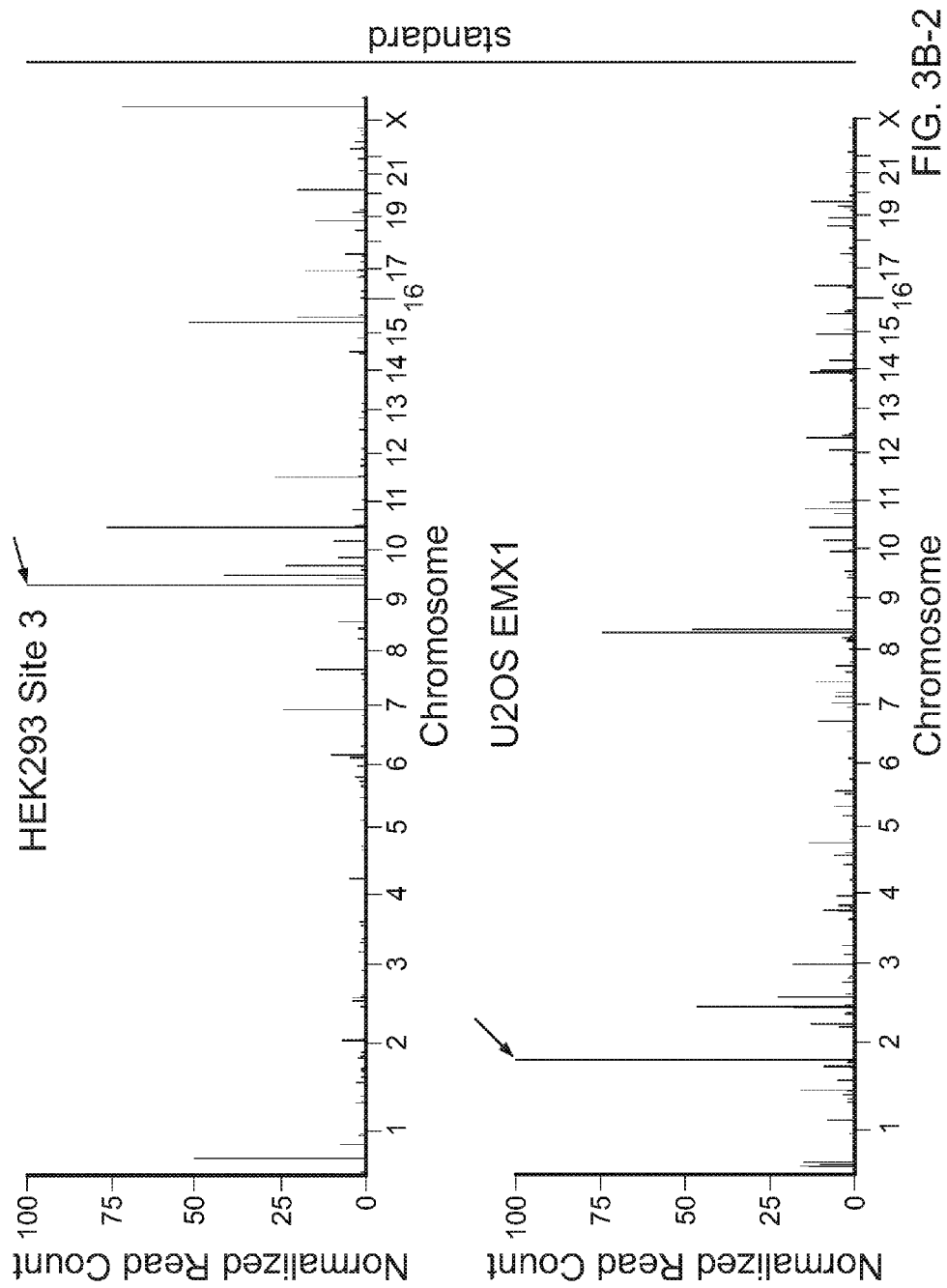
Figures 3, 3B:
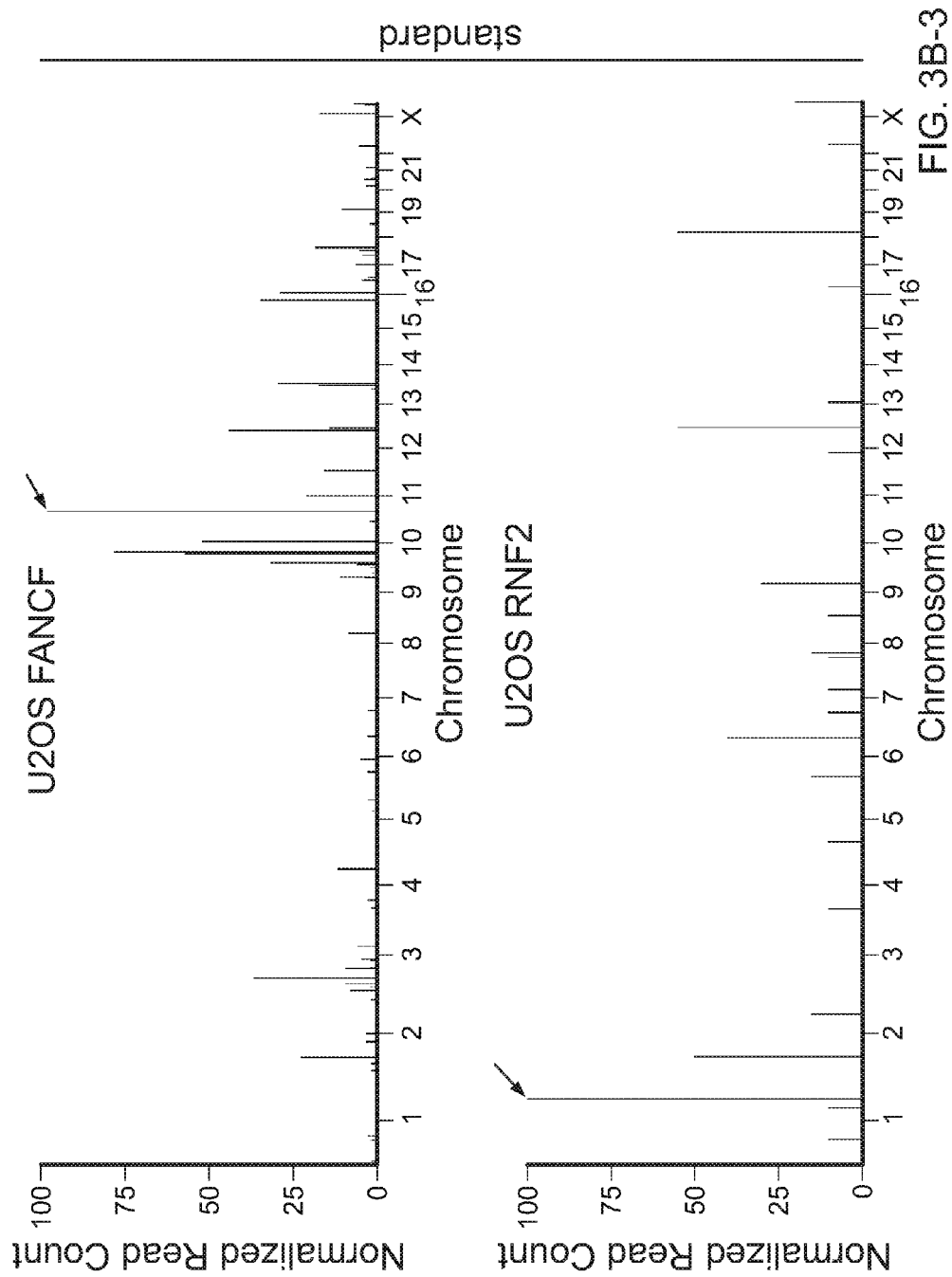

An exemplary method, described herein as Circularization for In vitro Reporting of CLeavage Effects by sequencing (CIRCLE-seq), is a novel cell-free strategy that enables highly efficient selective enrichment of nuclease-cleaved genomic DNA, which can then be used for high-throughput sequence and genomic off-target cleavage site discovery. Similar to the Full Interrogation of Nuclease DSBs by sequencing (FIND-seq) method (described in U.S. Ser. No. 62/217,690), CIRCLE-seq is based on the principle of generating a starting library of randomly sheared genomic DNA fragments whose DNA ends are protected in a way that prevents any subsequent ligation of a sequencing adapter. However, in CIRCLE-seq, this population of molecules is created by a novel unbiased intramolecular circularization method followed by exonuclease treatment to degrade any remaining residual linear fragments (FIG. 2). This enzymatically purified population of covalently closed circular genomic DNA molecules is then treated with an engineered nuclease of choice. Any DNA fragments harboring sites cleaved by this nuclease will be linearized, thereby releasing two available DNA ends to which a sequencing adapter can be ligated. Linearized, adapter-ligated fragments are subsequently amplified by PCR for high-throughput sequencing (See FIG. 2). Thus, CIRCLE-Seq virtually eliminates the very high background of random genomic reads observed with Digenome-seq.

In vitro conditions for the efficient intramolecular circularization of gDNA molecules at low concentrations of DNA were optimized, as this process is critical for the success and low background of this method. CIRCLE-seq enrichment of nuclease-cleaved fragments (based on experiments with CRISPR-Cas9 nucleases) was estimated to be nearly 6 orders of magnitude above background, thereby substantially reducing the high background of randomly sheared DNA fragments that are sequenced with a brute-force in vitro off-target cleavage site discovery method like Digenome-seq (FIG. 1A). The enrichment factor was calculated at the on-target site (where nearly 100% of fragments are expected to be cleaved in vitro) by dividing the number of reads that originate from the predicted breakpoint by the number of reads at those positions that would be expected by chance at the sequencing depth of the experiment.

Importantly, reducing the background dramatically increased the signal-to-noise ratio resulting from the CIRCLE-seq method, and reduced the probability of false positive calls due to the recovery of reads with uniform ends that can occur by chance with Digenome-seq. Initial circularization of genomic DNA fragments also enables the simultaneous recovery of both ends of a DSB in a single DNA molecule (and therefore a single DNA sequencing read), which in turns enables reference-independent discovery of off-target cleavage sites, an improvement over all previously described method for identifying nuclease-induced off-target effects that enables the approach to be used with genomic DNA from any organism, regardless of whether its genome sequence is known in advance. In addition, because there is minimal processing of the ends in vitro (as opposed to in cells where DNA repair pathways can resect or degrade ends), this method also greatly improves the nucleotide-level precision with which one can assign the location of the nuclease-induced break.

In initial validation experiments of CIRCLE-seq using CRISPR-Cas9 nucleases, the enrichment for Cas9 nuclease-cleaved fragments was nearly 20-fold more for CIRCLE-seq compared to the FIND-seq method (described in U.S. Ser. No. 62/217,690 and FIG. 1). A fundamental difference between these two methods is that FIND-seq is based on linear DNA substrate that is covalently closed with stem-loop adapters, whereas CIRCLE-seq is based on covalently closed fully circularized DNA substrates (FIG. 1A). One of the preferred exonucleases (the commercially-available PlasmidSafe ATP-dependent DNase from Epicentre) may retain some activity against the exposed ssDNA portions of the FIND-seq stem-loop ligated DNA substrates, which may explain why the CIRCLE-seq method results in higher enzymatic discrimination between linear and covalently closed DNA fragments and lower overall background.

Thus, the results provided show that CIRCLE-seq method is the most sensitive and sequencing-efficient in vitro approach described to date for determining genome-wide off-target cleavage sites of CRISPR-Cas9 nucleases. CIRCLE-seq has a substantially reduced rate of observed background reads relative to Digenome-seq, enabling it to sensitively identify off-target sites using a small fraction (~1.7%) of the total number of sequencing reads required with Digenome-seq. This need for only a more modest number of reads (e.g., those obtained with a benchtop sequencing instrument such as the Illumina MiSeq) makes the method accessible to most labs and more amenable from a cost perspective to automation and scaling.

CIRCLE-seq enables the production of larger datasets that permit the training of more accurate predictive algorithms for Cas9 off-target cleavage. The method can be cost-effectively automated and scaled and therefore it should be feasible to produce data identifying the off-target cleavage sites and relative in vitro cleavage efficiencies (as measured by CIRCLE-seq read counts) of thousands of gRNAs. Furthermore, if coupled with large-scale cell-based off-target datasets determined in ENCODE-characterized cell lines[39] with methods such as GUIDE-seq, it may be possible to better understand and quantify the impacts of chromatin and epigenetic modifications on the ability of nucleases to induce DNA DSBs.

For therapeutic applications, because CIRCLE-seq outperforms even the most highly sensitive cell-based genome-wide off-target detection methods such as GUIDE-seq and HTGTS, the method could be used as an initial screen to identify potential off-target sites that can then be verified with an orthogonal approach in actual nuclease-modified cells. In this study, targeted sequencing was used to search for GUIDE-seq dsODN tags to validate low-frequency sites (<0.1%) that would be challenging to identify by standard amplicon sequencing due to the indel error rate associated with next-generation sequencing (typically ~0.1%). However, this approach is limited to cells that can be transfected with the GUIDE-seq dsODN tag, something that may not be possible to do for all cells. Thus, an important and urgent area for future studies will be the development of alternative orthogonal cell-based methods to more sensitively measure off-target mutagenesis below the error rate of current high-throughput sequencing technologies. CIRCLE-seq can also be extended to analyze off-target effects of other nuclease platforms already in use for human therapeutics such as engineered zinc finger nucleases (ZFNs) and transcription activator-like effector nucleases (TALENs).

The CIRCLE-seq data herein provide greater support for the potential impacts of human genetic variation on off-target cleavage, a concept initially raised by others[36]. Our findings reinforce the importance of considering genotypes when evaluating off-target risk and argue that safety assessments of nucleases should include specificity profiles performed in a patient-specific way. Alternatively, CIRCLE-seq performed on a genomic DNAs from a large panel of genetically diverse cells may provide an effective way to define the vast majority of common and SNP-specific off-target effects for any given nuclease. In this regard, CIRCLE-seq has been performed on genomic DNA isolated from primary fibroblasts as would be obtained from a skin biopsy and buffy coat from a standard blood draw would also provide ample amounts of DNA to perform the assay. The simplicity, scalability, and reproducibility of CIRCLEseq makes it ideally suited for defining genome-wide off-target profiles on a large series of genomic DNA samples.

Stem-Loop Adapters and Sequencing Adapters

The present methods include the use of non-naturally occurring stem-loop adapters for circularizing the fragments by intramolecular ligation. The stem loop adapters include (from 5' to 3') a first region, e.g., of about 10-15, e.g., 12, nucleotides; a second region, e.g., of about 4-6, e.g., 5, nucleotides that forms at least one (and preferably only one) hairpin loops and includes a palindromic sequence suitable for intramolecular ligation, flanked by at least one (and preferably only one) uracil; and a third region, e.g., of about 10-15, e.g., 13, nucleotides that is complementary to the first region.

The present methods also include the use of sequencing adapters, which include a sequence of nucleotides for use in priming PCR or sequencing. The sequencing adapters typically include (from 5' to 3') a first region, e.g., of about 10-15, e.g., 12, nucleotides; a second region, e.g., of about 20-60, e.g., 40, nucleotides that forms at least one (and preferably only one) hairpin loops and includes a sequence suitable for use in PCR priming and/or sequencing, e.g., next generation sequencing (NGS), flanked by at least one (and preferably only one) uracil; and a third region, e.g., of about 10-15, e.g., 13, nucleotides that is complementary to the first region. The lengths of the first, second and third regions can vary depending on the NGS method selected, as they are dependent on the sequences that are necessary for priming for use with the selected NGS platform. In some embodiments, commercially available adapters that are variations of standard adapters (e.g., from Illumina or NEB) can be used.

The stem loop and sequencing adapters include at least one, preferably only one, uracil that allows the adaptor to be opened by Uracil DNA glycosylase (UDG) and Endonuclease VIII, a DNA glycosylase-lyase, e.g., the USER (Uracil-Specific Excision Reagent) Enzyme mixture (New England BioLabs). The UDG catalyzes the excision of uracil bases to form an abasic site but leave the phosphodiester backbone intact (see, e.g., Lindhal et al., J. Biol. Chem. 252:3286-3294 (1977); Lindhal, Annu. Rev. Biochem. 51:61-64 (1982)). The Endonuclease VIII breaks the phosphodiester backbone at the 3' and 5' sides of the abasic site (see, e.g., Melamede et al., Biochemistry 33:1255-1264 (1994); Jiang et al., J. Biol. Chem. 272:32230-32239 (1997)). This combination generates a single nucleotide gap at the location of a uracil. In some embodiments, the uracil is placed at or within 1, 2, 3, or 4 nucleotides of the 3' or 5' end of the sequence compatible for use in PCR priming and/or sequencing or the palindromic sequence.

In the present methods, all parts of the adapters are preferably orthogonal to the genome of the cell (i.e., are not present in or complementary to a sequence present in, i.e., have no more than 10%, 20%, 30%, 40%, or 50% identity to a sequence present in, the genome of the cell).

The sequencing adapters should preferably include a sequence compatible for use in PCR priming and/or sequencing, e.g., a primer site that is a randomized DNA barcode (e.g., SHAPE-SEQ, Lucks et al., Proc Natl Acad Sci USA 108: 11063-11068), unique molecular identifier (UMI) (see, e.g., Kivioja et al., Nature Methods 9, 72-74 (2012); Islam et al., Nature Methods 11, 163-166 (2014); Karlsson et al., Genomics. 2015 March; 105(3):150-8), or unique PCR priming sequence and/or unique sequence compatible for use in sequencing (e.g., NGS). The sequence compatible for use in sequencing can be selected for use with a desired sequencing method, e.g., a next generation sequencing method, e.g., Illumina, Ion Torrent or library preparation method like Roche/454, Illumina Solexa Genome Analyzer, the Applied Biosystems SOLiD™ system, Ion Torrent™ semiconductor sequence analyzer, PacBio® real-time sequencing and Helicos™ Single Molecule Sequencing (SMS). See, e.g., WO2014020137, Voelkerding et al., Clinical Chemistry 55:4 641-658 (2009) and Metzker, Nature Reviews Genetics 11:31-46 (2010)). A number of kits are commercially available for preparing DNA for NGS, including the ThruPLEX DNA-seq Kit (Rubicon; see U.S. Pat. Nos. 7,803,550; 8,071,312; 8,399,199; 8,728,737) and NEBNext® (New England BioLabs; see e.g., U.S. Pat. No. 8,420,319)). An exemplary stem loop adapter sequence is /5Phos/CGGTGGACCGATGATC/ideoxyU/ATCGGTCCACCG*T (SEQ ID NO:1; the asterisk indicates a phosphorothioate linkage). In some embodiments, the sequencing adapter is a commercially available sequencing adapter, e.g., from the NEBNext kit.

In some embodiments, the adapters include a restriction enzyme recognition site, preferably a site that is relatively uncommon in the genome of the cell.

The adapters are preferably modified; in some embodiments, the 5' ends of the hairpin adapters are phosphorylated, and/or the 3' ends include a phosphorothioate linkage. In some embodiments, the adapters are blunt ended. In some embodiments, the adapters include a random variety of 1, 2, 3, 4 or more nucleotide overhangs on the 5' or 3' ends, or include a single T at the 5' or 3' end.

The adapters can also include one or more additional modifications, e.g., as known in the art or described in PCT/US2011/060493. For example, in some embodiments, the hairpin adapters is biotinylated. The biotin can be anywhere internal to the hairpin adapters (e.g., a modified thymidine residue (Biotin-dT) or using biotin azide), but not on the 5' or 3' ends. This provides an alternate method of recovering fragments that contain ligated sequencing adapters. Whereas in some embodiments, these sequences are retrieved and amplified by PCR, in this approach they are physically pulled down and enriched by using the biotin, e.g., by binding to streptavidin-coated magnetic beads, or using solution hybrid capture; see, e.g., Gnirke et al., Nature Biotechnology 27, 182-189 (2009).

Engineered Nucleases

There are presently four main classes of engineered nucleases: 1) meganucleases, 2) zinc-finger nucleases, 3) transcription activator effector-like nucleases (TALEN), and 4) Clustered Regularly Interspaced Short Palindromic Repeats (CRISPR) Cas RNA-guided nucleases (RGN). Various components of these platforms can also be fused together to create additional nucleases such as MegaTALs and FokI-dCas9 fusions. See, e.g., Gaj et al., Trends Biotechnol. 2013 July; 31(7):397-405. The nuclease can be transiently or stably expressed in the cell, using methods known in the art; typically, to obtain expression, a sequence encoding a protein is subcloned into an expression vector that contains a promoter to direct transcription. Suitable eukaryotic expression systems are well known in the art and described, e.g., in Sambrook et al., *Molecular Cloning, A Laboratory Manual* (4th ed. 2013); Kriegler, Gene *Transfer and Expression: A Laboratory Manual* (2006); and *Current Protocols in Molecular Biology* (Ausubel et al., eds., 2010). Transformation of eukaryotic and prokaryotic cells are performed according to standard techniques (see, e.g., the reference above and Morrison, 1977, J. Bacteriol. 132:349-351; Clark-Curtiss & Curtiss, Methods in Enzymology 101:347-362 (Wu et al., eds, 1983).

Homing Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G, et al., Current Gene Therapy, 11:11-27, (2011); Arnould et al., Journal of Molecular Biology, 355:443-58 (2006); Arnould et al., Protein Engineering Design & Selection, 24:27-31 (2011); and Stoddard, Q. Rev. Biophys. 38, 49 (2005); Grizot et al., Nucleic Acids Research, 38:2006-18 (2010).

CRISPR-Cas Nucleases

Recent work has demonstrated that clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis of a simple and highly efficient method for performing genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas9 nuclease from *S. pyogenes* (hereafter simply Cas9) can be guided via simple base pair complementarity between 17-20 nucleotides of an engineered guide RNA (gRNA), e.g., a single guide RNA or crRNA/tracrRNA pair, and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). The engineered CRISPR from Prevotella and Francisella 1 (Cpf1) nuclease can also be used, e.g., as described in Zetsche et al., Cell 163, 759-771 (2015); Schunder et al., Int J Med Microbiol 303, 51-60 (2013); Makarova et al., Nat Rev Microbiol 13, 722-736 (2015); Fagerlund et al., Genome Biol 16, 251 (2015). Unlike SpCas9, Cpf1 requires only a single 42-nt crRNA, which has 23 nt at its 3' end that are complementary to the protospacer of the target DNA sequence (Zetsche et al., 2015). Furthermore, whereas SpCas9 recognizes an NGG PAM sequence that is 3' of the protospacer, AsCpf1 and LbCp1 recognize TTTN PAMs that are found 5' of the protospacer (Id.).

In some embodiments, the present system utilizes a wild type or variant Cas9 protein from *S. pyogenes* or *Staphylococcus aureus*, or a wild type Cpf1 protein from *Acidaminococcus* sp. BV3L6 or *Lachnospiraceae bacterium* ND2006 either as encoded in bacteria or codon-optimized for expression in mammalian cells and/or modified in its PAM recognition specificity and/or its genome-wide specificity. A number of variants have been described; see, e.g., WO 2016/141224, PCT/US2016/049147, Kleinstiver et al., Nat Biotechnol. 2016 August; 34(8):869-74; Tsai and Joung, Nat Rev Genet. 2016 May; 17(5):300-12; Kleinstiver et al., Nature. 2016 Jan. 28; 529(7587):490-5; Shmakov et al., Mol Cell. 2015 Nov. 5; 60(3):385-97; Kleinstiver et al., Nat Biotechnol. 2015 December; 33(12):1293-1298; Dahlman et al., Nat Biotechnol. 2015 November; 33(11):1159-61; Kleinstiver et al., Nature. 2015 Jul. 23; 523(7561):481-5; Wyvekens et al., Hum Gene Ther. 2015 July; 26(7):425-31; Hwang et al., Methods Mol Biol. 2015; 1311:317-34; Osborn et al., Hum Gene Ther. 2015 February; 26(2):114-26; Konermann et al., Nature. 2015 Jan. 29; 517(7536):583-8; Fu et al., Methods Enzymol. 2014; 546:21-45; and Tsai et al., Nat Biotechnol. 2014 June; 32(6):569-76, inter alia. The guide RNA is expressed or present in the cell together with the Cas9 or Cpf1. Either the guide RNA or the nuclease, or both, can be expressed transiently or stably in the cell or introduced as a purified protein or nucleic acid.

In some embodiments, the nuclease is a FokI-dCas9 fusion, RNA-guided FokI nucleases in which Cas9 nuclease has been rendered catalytically inactive by mutation (e.g., dCas9) and a FokI nuclease fused in frame, optionally with an intervening linker, to the dCas9. See, e.g., WO 2014/144288 and WO 2014/204578.

TAL Effector Repeat Arrays

TAL effectors of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in U.S. Ser. No. 61/610,212, and Reyon et al., Nature Biotechnology 30, 460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

Also suitable for use in the present methods are Mega-TALs, which are a fusion of a meganuclease with a TAL effector; see, e.g., Boissel et al., Nucl. Acids Res. 42(4): 2591-2601 (2014); Boissel and Scharenberg, Methods Mol Biol. 2015; 1239:171-96.

Zinc Fingers

Zinc finger proteins are DNA-binding proteins that contain one or more zinc fingers, independently folded zinc-containing mini-domains, the structure of which is well known in the art and defined in, for example, Miller et al., 1985, EMBO J., 4:1609; Berg, 1988, Proc. Natl. Acad. Sci. USA, 85:99; Lee et al., 1989, Science. 245:635; and Klug, 1993, Gene, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, Science, 252:809; Elrod-Erickson et al., 1998, Structure, 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, Gene 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, Gene Ther., 15:1463-68; Cathomen, 2008, Mol. Ther., 16:1200-07; Wu et al., 2007, Cell. Mol. Life Sci., 64:2933-44).

One existing method for engineering zinc finger arrays, known as "modular assembly," advocates the simple joining together of pre-selected zinc finger modules into arrays (Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277: 3850-56; Bae et al., 2003, Nat. Biotechnol., 21:275-280; Wright et al., 2006, Nat. Protoc., 1:1637-52). Although straightforward enough to be practiced by any researcher, recent reports have demonstrated a high failure rate for this method, particularly in the context of zinc finger nucleases (Ramirez et al., 2008, Nat. Methods, 5:374-375; Kim et al., 2009, Genome Res. 19:1279-88), a limitation that typically necessitates the construction and cell-based testing of very large numbers of zinc finger proteins for any given target gene (Kim et al., 2009, Genome Res. 19:1279-88).

Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

DNA

The methods described herein can be applied to DNA, e.g., genomic DNA isolated from any cell, artificially created populations of DNAs, or any other DNA pools, as it is performed in vitro.

Sequencing

As used herein, "sequencing" includes any method of determining the sequence of a nucleic acid. Any method of sequencing can be used in the present methods, including chain terminator (Sanger) sequencing and dye terminator sequencing. In preferred embodiments, Next Generation Sequencing (NGS), a high-throughput sequencing technology that performs thousands or millions of sequencing reactions in parallel, is used. Although the different NGS platforms use varying assay chemistries, they all generate sequence data from a large number of sequencing reactions run simultaneously on a large number of templates. Typically, the sequence data is collected using a scanner, and then assembled and analyzed bioinformatically. Thus, the sequencing reactions are performed, read, assembled, and analyzed in parallel; see, e.g., US 20140162897, as well as Voelkerding et al., Clinical Chem., 55: 641-658, 2009; and MacLean et al., Nature Rev. Microbiol., 7: 287-296 (2009). Some NGS methods require template amplification and some that do not. Amplification-requiring methods include pyrosequencing (see, e.g., U.S. Pat. Nos. 6,210,89 and 6,258,568; commercialized by Roche); the Solexa/Illumina platform (see, e.g., U.S. Pat. Nos. 6,833,246, 7,115,400, and 6,969,488); and the Supported Oligonucleotide Ligation and Detection (SOLiD) platform (Applied Biosystems; see, e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146;

7,313,308; and 7,476,503). See, e.g., US 20130274147; US20140038831; Metzker, Nat Rev Genet 11(1): 31-46 (2010).

Alternatively, hybridization-based sequence methods or other high-throughput methods can also be used, e.g., microarray analysis, NANOSTRING, ILLUMINA, or other sequencing platforms.

Kits

Also provided herein are kits for use in the methods described herein. The kits can include one or more of the following: hairpin adapters; reagents and/or enzymes for end repair and A tailing (e.g., T4 polymerase, Klenow fragment, T4 Polynucleotide Kinase (PNK), and/or Taq DNA Polymerase); exonuclease; uracil DNA glycosylase (UDG) and/or endonuclease VIII, a DNA glycosylase-lyase, e.g., the USER (Uracil-Specific Excision Reagent) Enzyme mixture (New England BioLabs); purified nuclease, e.g., cas9 protein; guideRNA (e.g., control gRNA); gDNA template (e.g., control gDNA template); and/or instructions for use in a method described herein.

EXAMPLES

The invention is further described in the following examples, which do not limit the scope of the invention described in the claims.

Materials and Methods

The following materials and methods were used in Examples 1-6 below.

Cell Culture and Transfection

Cell culture experiments were performed on human U2OS (gift from T. Cathomen), HEK293 (Thermo-Fisher), K562, and PGP1 fibroblast cells (gift from G. Church). U2OS and HEK293 cells were cultured in Advanced DMEM (Life Technologies) supplemented with 10% FBS, 2 mM GlutaMax (Life Technologies) and penicillin/streptomycin at 37° C. with 5% $CO_2$. K562 cells were cultured in RPMI 1640 (Life Technologies) supplemented with 10% FBS, 2 mM GlutaMax and penicillin/streptomycin at 37° C. with 5% $CO_2$. Human PGP1 fibroblasts were cultured in Eagle's DMEM (ATCC) with 10% FBS, 2 mM GlutaMax and penicillin/streptomycin at 37° C. with 5% $CO_2$. For CIRCLE-seq experiments, genomic DNA was isolated using Gentra Puregene Tissue Kit (Qiagen) and quantified by Qubit (Thermo Fisher). For targeted tag-integration deep-sequencing experiments, U2OS cells (program DN-100), HEK293 cells (program CM-137), and K562 cells (program FF-120) were transfected in 20 µl Solution SE (Lonza) on a Lonza Nucleofector 4-D, according to the manufacturer's instructions. In U2OS cells, 500 ng of pCAG-Cas9 (pSQT817), 250 ng of gRNA encoding plasmids, and 100 pmol of GUIDE-seq end-protected dsODN were cotransfected. Genomic DNA for targeted tag integration sequencing was harvested approximately 72 hours post transfection using the Agencourt DNAdvanced Genomic DNA Isolation Kit (Beckman Coulter Genomics).

In Vitro Transcription of gRNAs

Annealed oligonucleotides containing gRNA target sites were cloned into plasmid NW59 containing a T7 RNA polymerase promoter site. The gRNA expression plasmid was linearized with HindIII restriction enzyme (NEB) and purified with MinElute PCR Purification Kit (Qiagen). The linearized plasmid was used as DNA template for in vitro transcription of the gRNA using MEGAshortscript Kit, according to the manufacturer's instructions (Thermo Fisher).

CIRCLE-Seq Library Preparation

For the experiments with gRNAs previously evaluated by GUIDE-seq, CIRCLE-seq experiments were performed on genomic DNA from the same cells in which they were evaluated by GUIDE-seq (either U2OS or HEK293 cells). Purified genomic DNA was sheared with a Covaris S200 instrument to an average length of 300 bp, end-repaired, A-tailed, and ligated to uracil (deoxyuridine)-containing stem-loop adapter oSQT1288 5'-P-CGGTGGACCGATGATCUATCGGTCCACCG*T-3' (SEQ ID NO:1), where * indicates phosphorothioate linkage. Adapter-ligated DNA was treated with a mixture of Lambda Exonuclease (NEB) and E. coli Exonuclease I (NEB), then with USER enzyme (NEB) and T4 polynucleotide kinase (NEB). DNA was circularized at 5 ng/ul concentration with T4 DNA ligase, and treated with Plasmid-Safe ATP-dependent DNase (Epicentre) to degrade remaining linear DNA molecules. In vitro cleavage reactions were performed in a 100 µl, with Cas9 nuclease buffer (NEB), 90 nM SpCas9 protein, 90 nM in vitro transcribed gRNA, and 250 ng of Plasmid-Safe-treated circularized DNA. Digested products were A-tailed, ligated with a hairpin adapter, treated with USER enzyme (NEB), and amplified by PCR using Kapa HiFi polymerase (Kapa Biosystems). Completed libraries were quantified by droplet digital PCR (Bio-Rad) and sequenced with 150 bp paired end reads on an Illumina MiSeq instrument. Detailed user protocols for CIRCLE-seq library construction is provided in Example 7.

Targeted Deep-Sequencing

U2OS cells were transfected with Cas9 and gRNA expression plasmids, in addition to the GUIDE-seq dsODN as described above. Off-targets sites identified by CIRCLE-seq were amplified from the isolated U2OS genomic DNA using Phusion Hot Start Flex DNA polymerase (New England Biolabs). Triplicates of PCR products were generated from each transfection condition with 100 ng of genomic DNA as the input for each PCR. PCR products were normalized in concentration, pooled into different libraries corresponding to different transfection conditions, and purified with Ampure XP magnetic beads (Agencourt). Illumina Tru-seq deep-sequencing libraries were constructed using 500 ng of each pooled samples (KAPA Biosystems), quantified by real-time PCR (KAPA Biosystems), and sequenced on an Illumina MiSeq instrument.

CIRCLE-Seq Data Analysis

Paired-end reads were merged and then mapped using bwa[40] mem with default parameters. The start mapping positions of reads that map in the expected orientation with mapping quality ≥50 were tabulated and genomic intervals that are enriched in nuclease-treated samples were identified. The interval and 20-bp of flanking reference sequence on either side was searched for potential nuclease-induced off-target sites with an edit distance of less than or equal to 6, allowing for gaps.

samtools[41,42] mpileup was used to non-reference genetic variation in identified off-target sites. Positions with average quality score greater than 20 were considered as possible variants and confirmed by visual inspection.

Reference-independent discovery of off-target cleavage sites was performed by reverse complementing the sequence of one read of a pair and concatenating it with the other. An interval of starting 20-bp on either side of the junction was directly searched for potential off-target cleavage sites with edit distance of ≤6 allowing for gaps and read counts corresponding to identified sites were tabulated.

CIRCLE-Seq Open-Source Analysis Software

To enable the broad use of CIRCLE-seq for genome-wide detection of nuclease off-target sites, we developed a freely available, open-source Python package circleseq for the analysis of CIRCLE-seq experimental data. Provide with a simple sample manifest, the circleseq software performs full end-to-end analysis of CIRCLE-seq sequencing data with a single command, and returns tables of candidate off-target cleavage site positions, as well as visual alignments of off-target sequences.

Digenome-Seq Data Analysis

Figure 2B:
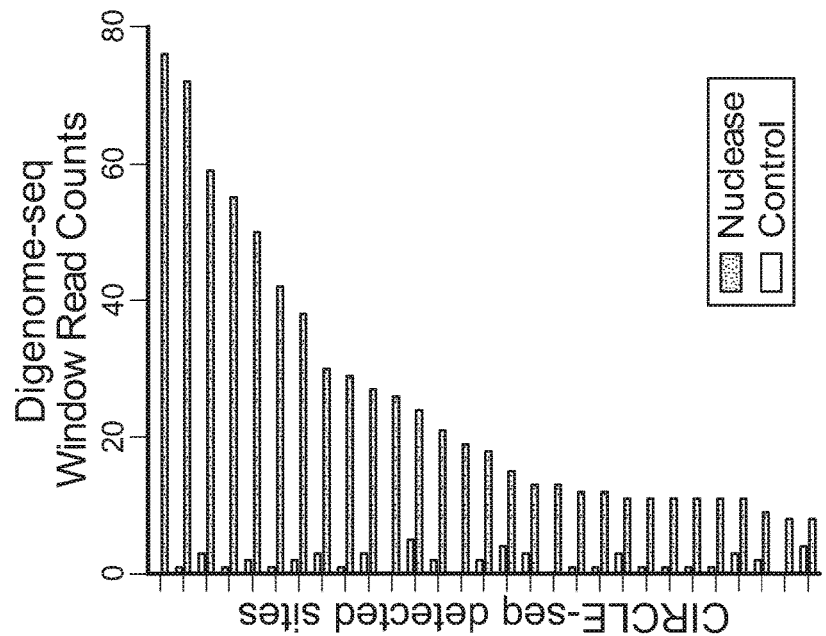
FIGS. 2A-D. Comparison of CIRCLE-seq with Digenome-seq. (A) Venn diagram showing intersections of off-target sites of Cas9 and a gRNA targeted against the HBB gene detected by CIRCLE-seq and Digenome-seq. (B) Barplot of Digenome-seq read counts at off-target cleavage positions found by CIRCLE-seq but not Digenome-seq for nuclease-treated (shaded bars) and control (open bars) HAP1 genomic DNA. (C) Plots comparing mapping of sequencing reads for CIRCLE-seq and Digenome-seq at the on-target site of a gRNA targeted to the HBB locus. Both nuclease-treated and control samples are shown. Thin grey line indicates expected cleavage site position; read coverage for forward reads is colored in black, and reverse reads in white. (D) CIRCLE-seq start mapping position plot at the on-target site for the HBB gRNA used in (C). (+) strand mapping reads are shown in white bars, (−) strand mapping reads are colored in shaded bars.

Read counts of mapping positions in a narrow window (+/−3 bp) around cleavage sites identified by CIRCLE-seq were tabulated from original Digenome-seq sequencing alignments. Significant evidence of cleavage at a 0.01 significance level was evaluated by fitting a negative binomial distribution, and statistically significant sites by this criteria were included in FIG. 2b.

Example 1. Overview and Optimization of the CIRCLE-Seq Method

Figure 1C:
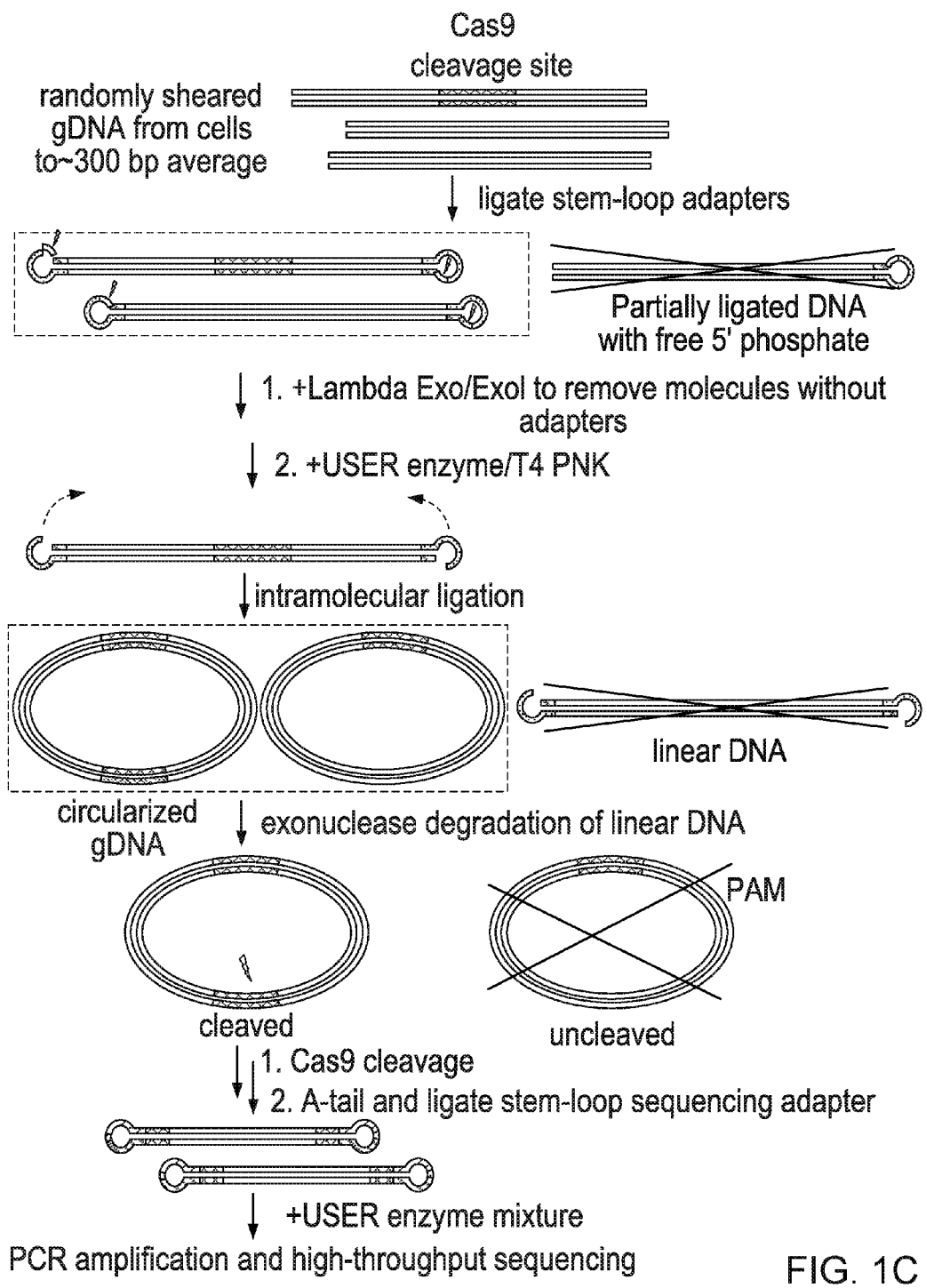

We reasoned that the confounding background reads of random genomic DNA that occur with Digenome-seq (FIG. 1A) would be substantially reduced by the selective enrichment of Cas9 nuclease-cleaved genomic DNA fragments. To accomplish this, we designed a restriction enzyme-independent strategy to circularize randomly sheared linear genomic DNA with subsequent enzymatic degradation of residual uncircularized DNA (FIGS. 1B-C). We envisioned that cleavage of this population of genomic DNA circles by a site-specific nuclease at on- and off-target sites would release linearized DNA ends, to which next-generation sequencing adapters could be ligated. We hypothesized that collectively these steps should enable the selective enrichment and sequencing of nuclease-induced DNA ends and suppress the undesired sequencing of randomly distributed ends sheared genomic DNA preparations. Importantly, in contrast to all other genome-wide methods for nuclease off-target cleavage site discovery, our strategy would uniquely enable sequencing of both sides of a single cleavage site in one DNA molecule using paired-end sequencing.

Figure 1D:
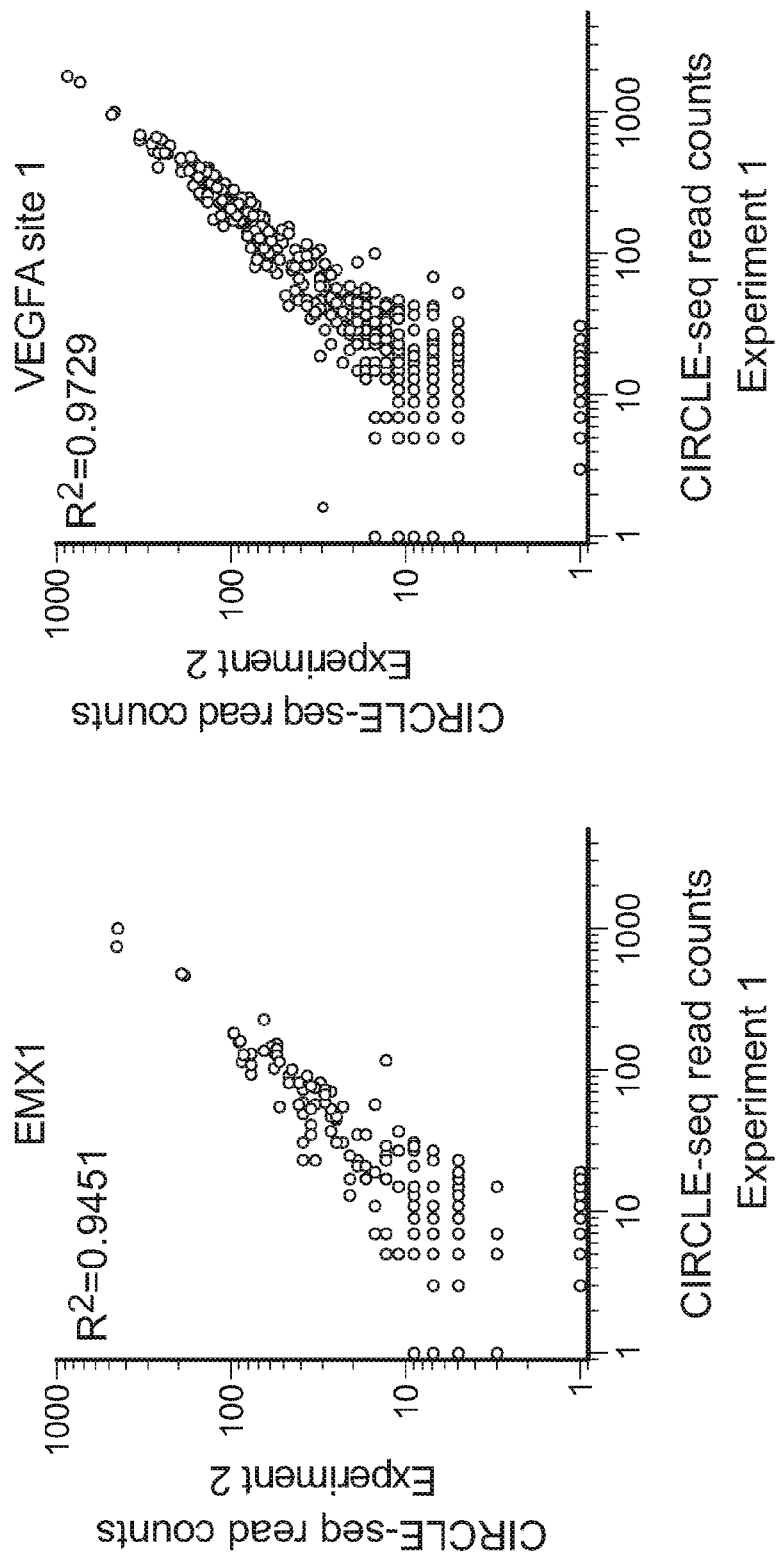

Optimization of this method, which we called CIRCLE-seq, and characterization of its technical reproducibility (FIG. 1D), was performed as follows. To achieve restriction-enzyme independent circularization of genomic DNA, we tested a strategy based on ligation of a uracil-containing stem loop adapter to a end-repaired, A-tailed PCR amplicon. We enzymatically selected for covalently-closed DNA molecules that had stem-loop adapters ligated to both sides with a mixture of Lambda exonuclease and E. coli exonuclease I. 4 bp overhangs were released using a mixture of USER enzyme and T4 PNK, ligation was performed with T4 DNA ligase under conditions favoring intramolecular ligation, and successful circularization was measured by capillary electrophoresis. The conditions resulting in highest circularization efficiency (400 U T4 DNA ligase, 5 ng/ul DNA concentration) were used for subsequent experiments. To characterize the technical reproducibility of CIRCLE-seq, we performed independent library preparations from the same source of U2OS genomic DNA. We observed strong CIRCLE-seq read count correlations in independent technical replicates (FIG. 1D).

Figure 2A:
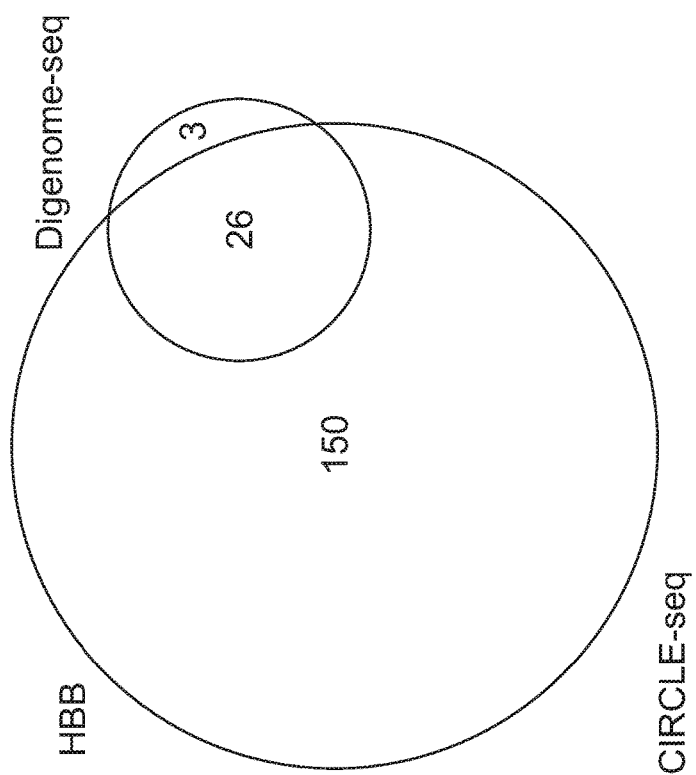
Figure 2C:
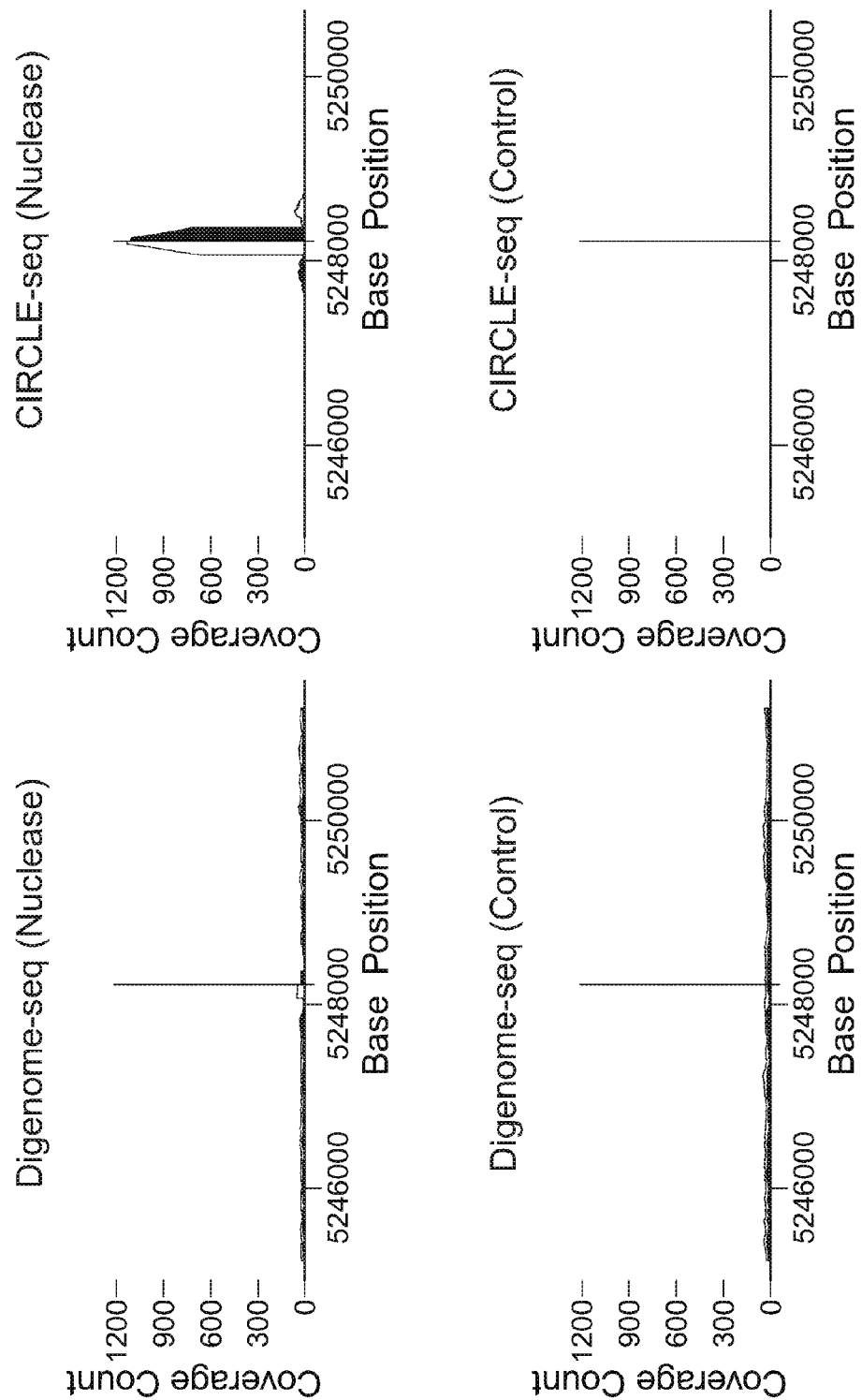
Figure 2D:
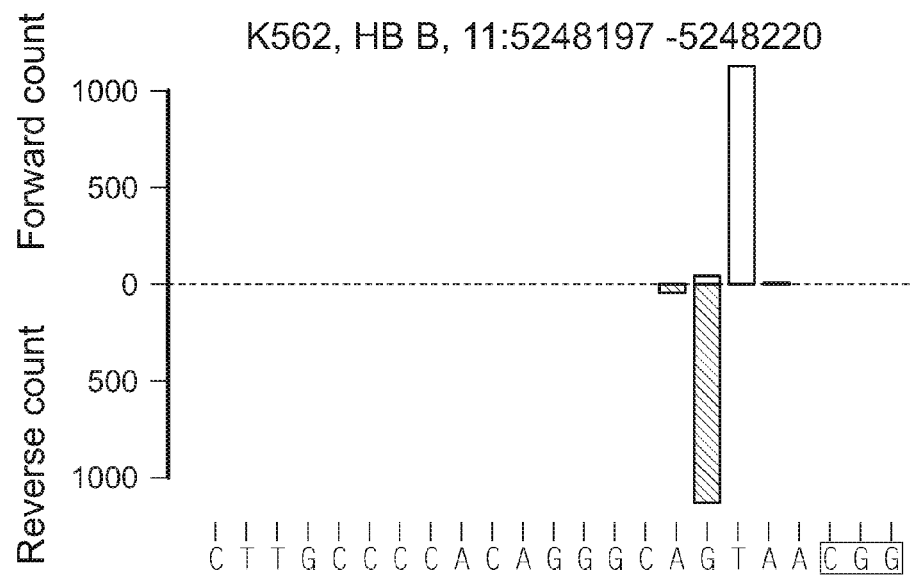

Example 2. CIRCLE-Seq Enables Highly Sensitive In Vitro Detection of CRISPR-Cas9 Genome-Wide Off-Target Cleavage Sites To test the efficacy and sensitivity of CIRCLE-seq, we used it to identify off-target cleavage sites of Cas9 directed by the single published gRNA that has been profiled with the most recent and accurate version of Digenome-seq to date[35]. CIRCLE-seq evaluation of SpCas9 with this gRNA (targeted to the human HBB gene) on human K562 cell genomic DNA identified not only 26 of the 29 off-target sites previously identified by GUIDE-seq but also 156 new off-target sites (FIG. 2A). For the three off-target sites found by Digenome-seq but not by CIRCLE-seq, we observed supporting reads in the CIRCLE-seq data, demonstrating that these sites were simply undersampled in these particular experiments. Of the 156 new off-target cleavage sites detected only by CIRCLE-seq, we found that 29 of these also showed evidence of cleavage in the original Digenome-seq data[34] (FIG. 2B); the inability of Digenome-seq to call these sites is most likely due to stringent informatics scoring criteria required to contend with the abundant genome-wide background reads generated by this method. By contrast, we found that such background reads were rare with CIRCLE-seq (FIG. 2C). Indeed, we estimate the enrichment factor of CIRCLE-seq for nuclease-cleaved sequence reads to random background reads is ~180,000-fold better than that of Digenome-seq based on examinination of an on-target site with the two methods and adjusting for sequencing depth (FIG. 2C). The start mapping positions of bidirectional CIRCLE-seq reads are consistent with the expected cleavage site of SpCas9 (3 bp before the PAM sequence) (FIG. 2D), demonstrating the ability of this method to precisely map cleavage positions with nucleotide-level precision. Taken together, these results demonstrate that CIRCLE-seq possesses higher signal-to-noise relative to Digenome-seq, which most likely accounts for its greater sensitivity for identifying genome-wide off-target sites.

Figures 3, 3B, 4:
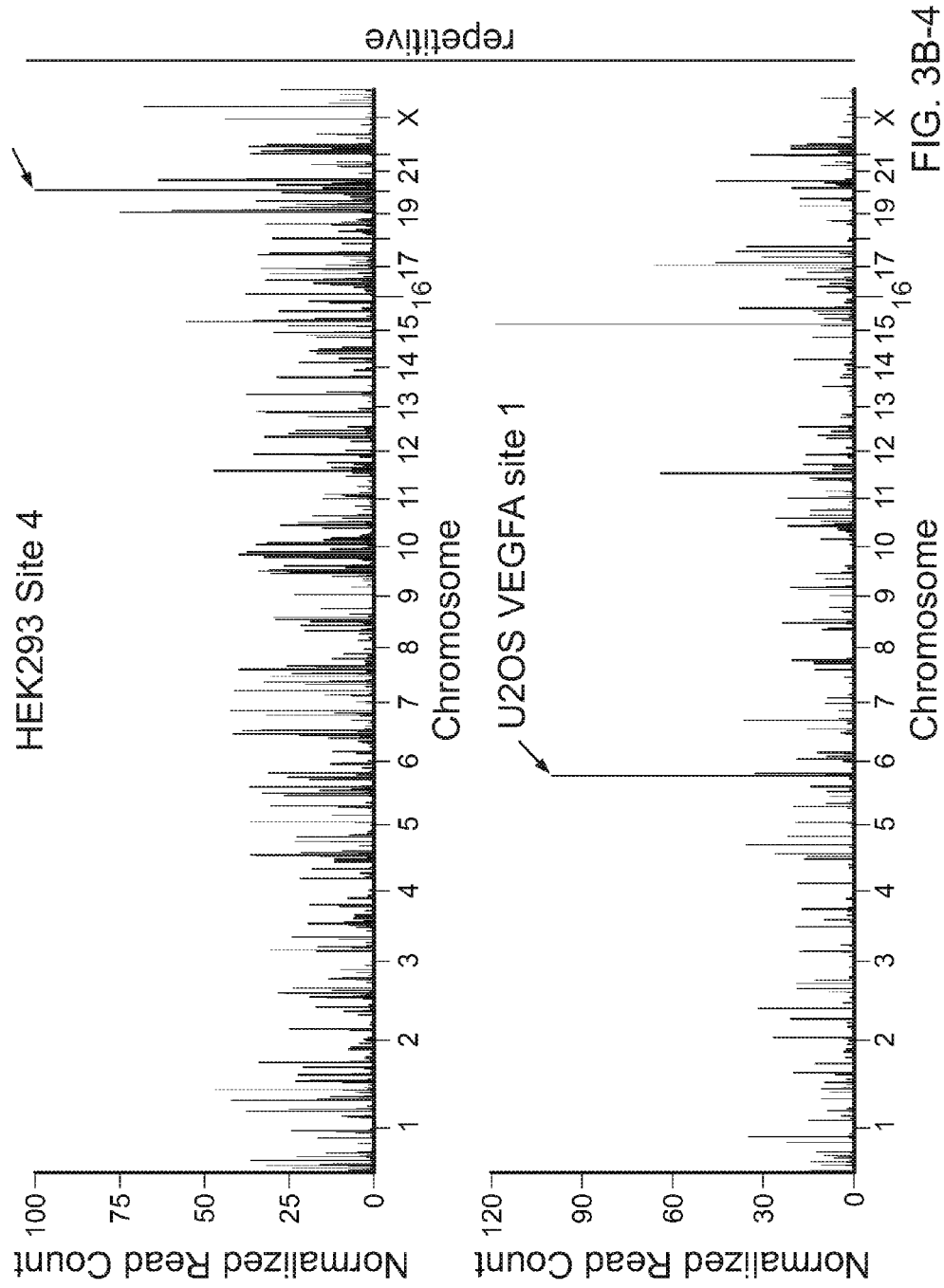
Figures 3, 3B, 4, 5:
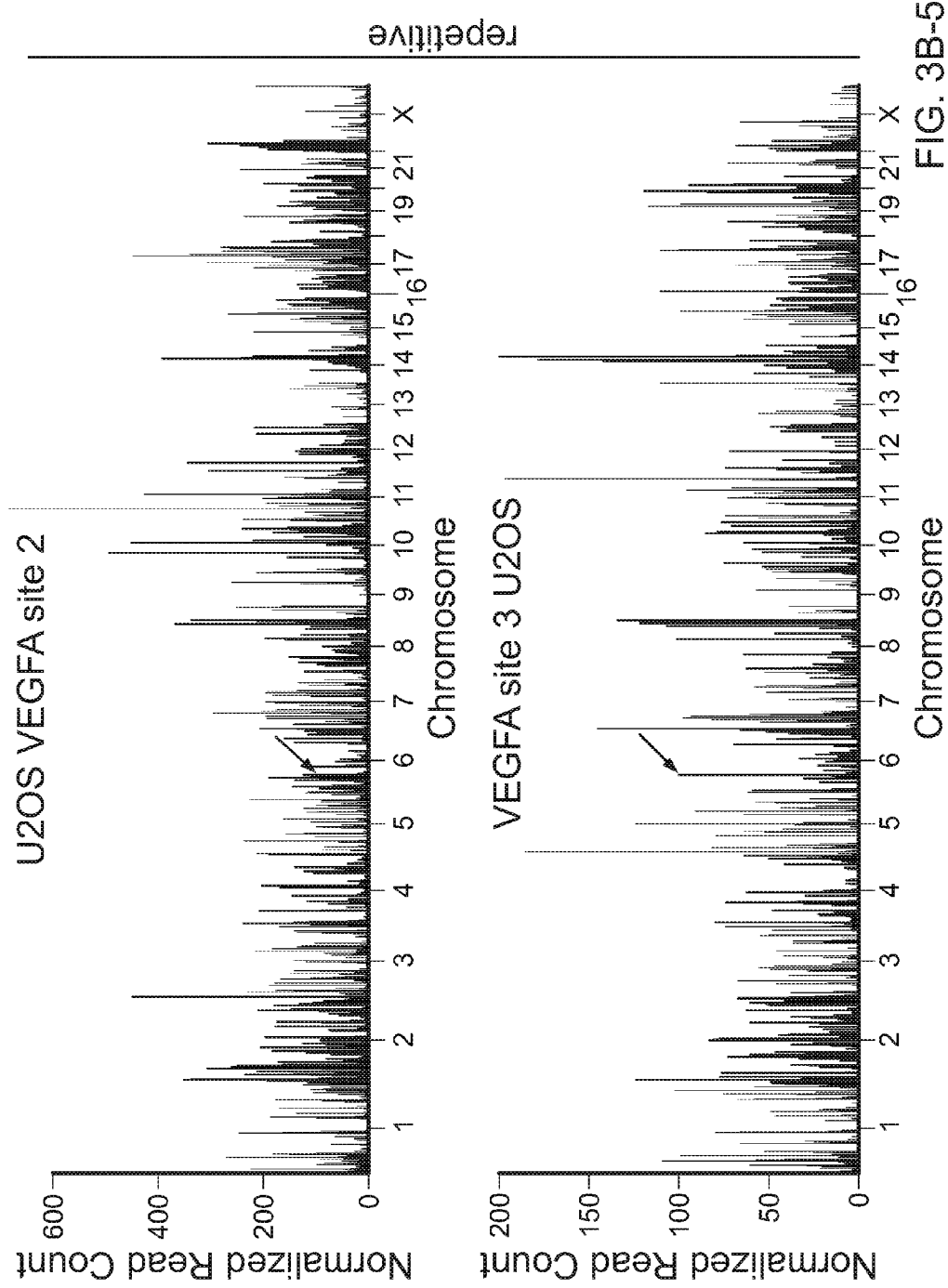
Figure 3C:
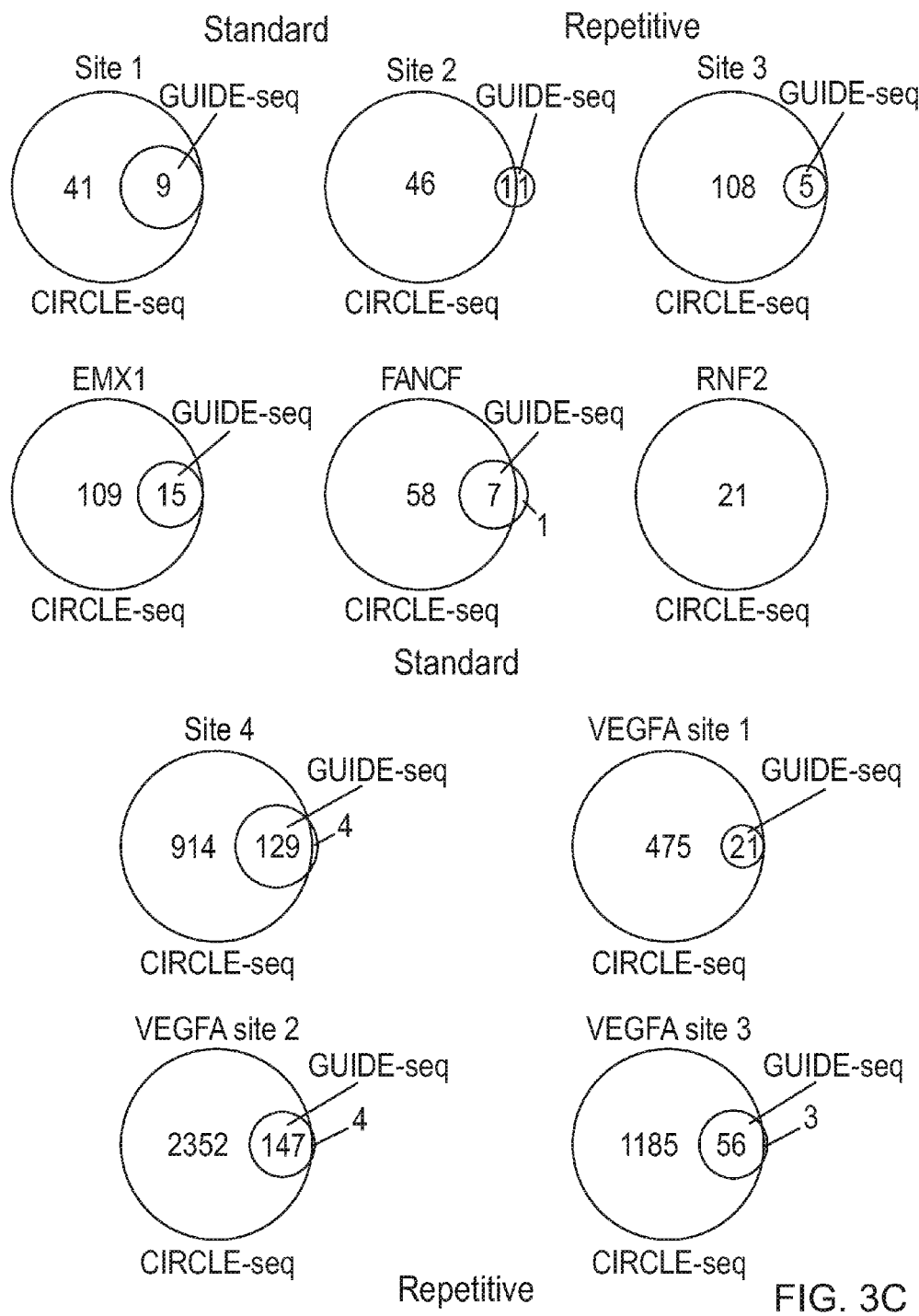

Example 3. Direct Comparisons of CIRCLE-Seq with Cell-Based Off-Target Determination Methods We next compared the performance of CIRCLE-seq with GUIDE-seq, one of the most sensitive cell-based approaches currently available for genome-wide off-target mutation identification[30]. In an initial comparison, we used CIRCLE-seq to assess SpCas9 with six different gRNAs targeted to standard non-repetitive sequences and that had been previously characterized by GUIDE-seq across two different human cell lines. CIRCLE-seq identified variable numbers of off-target cleavage sites for these six different gRNAs, ranging in number from as few as 21 to as many as 124 (FIG. 3A; Exemplary data for one replicate of an EMX1 targeting experiment is shown in Table 2, below; EMX1 target site sequence: GAGTCCGAGCAGAAGAAGAAGG (SEQ ID NO:2)) and distributed throughout the human genome (FIG. 3B). Importantly, for all six gRNAs, CIRCLE-seq identified many more off-target sites than previously found by GUIDE-seq, including the gRNA targeted to RNF2 for which we had previously been unable to identify off-target sites using GUIDE-seq. For four of the six gRNAs, CIRCLE-seq detected all of the off-target sites identified by GUIDE-seq (FIG. 3C) and for the other two gRNAs, it detected all but one off-target for each (FIG. 3C). Closer examination of the CIRCLE-seq data for these experiments actually revealed evidence of some supporting reads for these two off-target sites but not of a sufficient number required to meet our statistical threshold for detection in these experiments. In addition, as might be expected, these two undetected sites had been at the edge of detection in our GUIDE-seq experiments. Taken together, these findings again suggest that these two off-target sites would be detected if we modestly increased CIRCLE-seq sequencing depth.

To provide a more challenging test of CIRCLE-seq, we also profiled SpCas9 with four additional gRNAs that are targeted to repetitive sequences and that had been previously characterized by GUIDE-seq. Due to the repetitive nature of their targets, these four gRNAs have a relatively larger number of closely matched sites in the human genome (Table 1) and, not surprisingly, have been shown by GUIDE-seq to induce a large number of off-target effects in human cells[30]. As expected, CIRCLE-seq also identified a much larger number of off-target sites, ranging in number from 496 to 2503 for each of the four gRNAs (FIG. 3A and Table 2) and distributed throughout the human genome (FIG. 3B). Included among these were 353 of the 364 off-target sites previously identified by GUIDE-seq experiments (FIG. 3C). For 9 of the 11 sites found by GUIDE-seq but not identified by CIRCLE-seq, evidence of supporting reads could be found in the CIRCLE-seq data but not of a sufficiently high number for statistical cutoff, once again suggesting that greater sequencing read depth would enable detection of these sites.

Figure 3D:
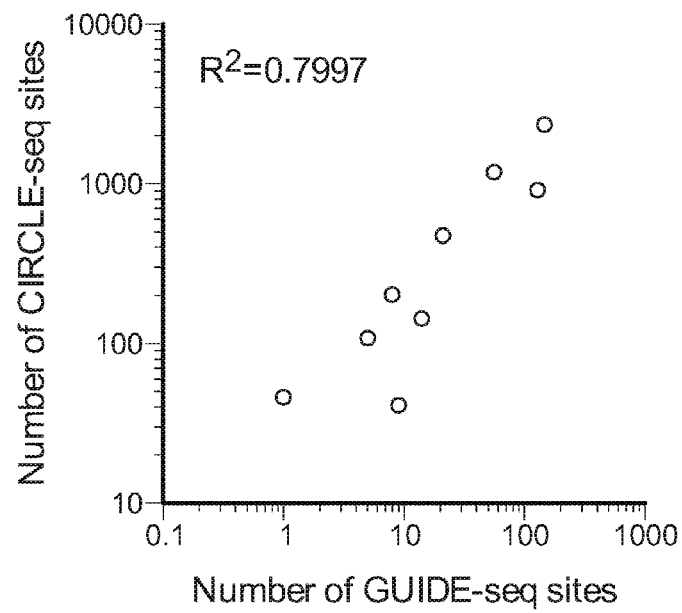
Figure 3E:
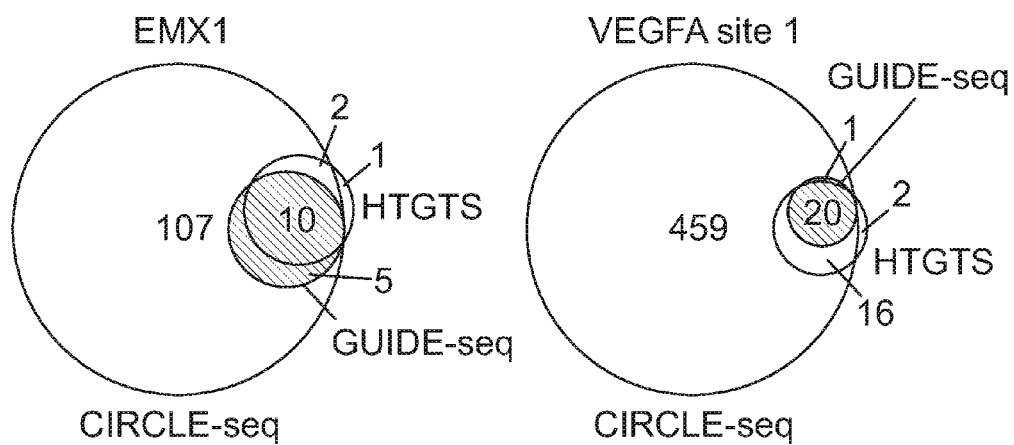

We next used CIRCLE-seq to profile SpCas9 and two gRNAs that had previously been characterized by the cell-based HTGTS method. These experiments revealed that, for both gRNAs (targeted to sites in the EMX1 and VEGFA genes), CIRCLE-seq found 50 of the 53 off-target sites (94%) previously identified by HTGTS (FIG. 3E). Among the three HTGTS sites not detected by CIRCLE-seq, two were found when additional experimental replicates were performed and the third had a low HTGTS score, suggesting that these three sites would be detected with greater CIRCLE-seq sequencing depth. Importantly, CIRCLE-seq also found a much greater number of off-target sites than had been previously identified by HTGTS (FIG. 3D).

TABLE 1

| Target Site Sequence | Target site | Numbers of in silico off-target sites predicted in the human genome | | | | | | | |
|---|---|---|---|---|---|---|---|---|---|
| | | 0 | 1 | 2 | 3 | 4 | 5 | 6 | 7 | 8 |
| GAGTCCGAGCAGAAGAAGAANGG (SEQ ID NO: 2) | EMX1 | 1 | 1 | 2 | 27 | 421 | 4313 | 34761 | 218047 | 1156729 |
| GGAATCCCTTCTGCAGCACCNGG (SEQ ID NO: 3) | FANCF | 1 | 1 | 3 | 33 | 449 | 3155 | 21793 | 135144 | 724696 |
| GTCATCTTAGTCATTACCTGNGG (SEQ ID NO: 4) | RNF2 | 1 | 1 | 1 | 11 | 204 | 2029 | 18023 | 138077 | 830825 |
| GGGAAAGACCCAGCATCCGTNGG (SEQ ID NO: 5) | Site_1 | 1 | 1 | 2 | 14 | 132 | 1499 | 13410 | 99120 | 627262 |
| GAACACAAAGCATAGACTGCNGG (SEQ ID NO: 6) | Site_2 | 1 | 1 | 2 | 16 | 239 | 3075 | 27129 | 180822 | 1026201 |
| GGCCCAGACTGAGCACGTGANGG (SEQ ID NO: 7) | Site_3 | 1 | 1 | 2 | 16 | 156 | 1831 | 15689 | 112679 | 645364 |
| GGCACTGCGGCTGGAGGTGGNGG (SEQ ID NO: 8) | Site_4 | 1 | 1 | 10 | 125 | 1231 | 9452 | 56139 | 297118 | 1471381 |
| GGGTGGGGGGAGTTTGCTCCNGG (SEQ ID NO: 9) | VEGFA_site_1 | 1 | 2 | 6 | 51 | 442 | 3870 | 28723 | 178630 | 929570 |
| GACCCCCTCCACCCCGCCTCNGG (SEQ ID NO: 10) | VEGFA_site_2 | 1 | 1 | 10 | 58 | 726 | 7636 | 51673 | 305299 | 1469770 |
| GGTGAGTGAGTGTGTGCGTGNGG (SEQ ID NO: 11) | VEGFA_site_3 | 1 | 2 | 37 | 1077 | 24857 | 530932 | 921004 | 1538579 | 2944099 |

TABLE 2

| Chromosome:Start-End | Read | Strand | Off-target Sequence | SEQ ID NO: | Distance | Length |
|---|---|---|---|---|---|---|
| 2:73160981-73161004 | 1004 | + | GAGTCCGAGCAGAAGAAGAAGGG | 12. | 0 | 23 |
| 8:120587494-120587517 | 746 | − | AAGGCCAAGCAGAAGAGTAATGG | 13. | 5 | 23 |
| 8:128801241-128801264 | 478 | + | GAGTCCTAGCAGGAGAAGAAGAG | 14. | 3 | 23 |
| 2:219845055-219845078 | 466 | + | GAGGCCGAGCAGAAGAAAGACGG | 15. | 3 | 23 |
| 3:5031597-5031620 | 226 | + | GAATCCAAGCAGGAGAAGAAGGA | 16. | 4 | 23 |
| 3:95690179-95690202 | 182 | − | TCATCCAAGCAGAAGAAGAGAG | 17. | 5 | 23 |
| 2:218378101-218378124 | 180 | − | GAGTCTAAGCAGGAGAATAAAGG | 18. | 4 | 23 |

TABLE 2 -continued

| Chromosome:Start-End | Read | Strand | Off-target Sequence | SEQ ID NO: | Distance | Length |
|---|---|---|---|---|---|---|
| 1:23720611-23720634 | 160 | - | AAGTCCGAGGAGAGGAAGAAAGG | 19. | 3 | 23 |
| 1:234492858-234492881 | 158 | - | GAAGTAGAGCAGAAGAAGAAGCG | 20. | 5 | 23 |
| 1:33606473-33606496 | 152 | - | GAGCCTGAGCAGAAGGAGAAGGG | 21. | 3 | 23 |
| 11:43747931-43747954 | 146 | + | AAGCCCGAGCAAAGGAAGAAAGG | 22. | 4 | 23 |
| 12:106646073-106646096 | 140 | + | AAGTCCATGCAGAAGAGGAAGGG | 23. | 4 | 23 |
| 5:45359060-45359083 | 136 | - | GAGTTAGAGCAGAAGAAGAAAGG | 24. | 2 | 23 |
| 1:21580957-21580980 | 134 | - | TCTTCCAAGCAGAGGAAGAAAGG | 25. | 5 | 23 |
| 10:128080178-128080201 | 132 | + | GAGTACAAGCAGATGAAAAACGG | 26. | 4 | 23 |
| 14:43156800-43156823 | 130 | - | GAGGCCAAGCAGAAAAAAAATGG | 27. | 4 | 23 |
| 2:172374197-172374220 | 128 | - | GAAGTAGAGCAGAAGAAGAAGCG | 28. | 5 | 23 |
| 20:6653992-6654015 | 126 | - | AAGTCCAGACAGAAGAAGAAGGA | 29. | 5 | 23 |
| 16:78848843-78848866 | 116 | - | AAATCCAACCAGAAGAAGAAAGG | 30. | 4 | 23 |
| 15:44109746-44109769 | 114 | + | GAGTCTAAGCAGAAGAAGAAGAG | 31. | 3 | 23 |
| 7:141972555-141972578 | 114 | - | AAGTCCGGGCAAAAGAGGAAAGG | 32. | 4 | 23 |
| 7:31901071-31901094 | 108 | - | GAGGCCAAGCAGAAAGAAAAAGG | 33. | 5 | 23 |
| 1:27913373-27913396 | 102 | + | AGGTCAGAGCAGAAGAAAAGAGG | 34. | 5 | 23 |
| 14:48932102-48932125 | 100 | + | GAGTCCCAGCAAAAGAAGAAAAG | 35. | 3 | 23 |
| 4:48639390-48639413 | 92 | + | CACTCCAAGTAGAAGAAGAAAAG | 36. | 5 | 23 |
| 10:91416144-91416167 | 90 | + | ATGTCCAAGCAGAAGAAGTCTGG | 37. | 5 | 23 |
| 2:54284994-54285017 | 90 | + | AAGGCAGAGCAGAGGAAGAGAGG | 38. | 5 | 23 |
| 15:100292461-100292484 | 82 | + | AAGTCCCGGCAGAGGAAGAAGGG | 39. | 4 | 23 |
| 1:151027591-151027614 | 80 | - | TTCTCCAAGCAGAAGAAGAAGAG | 40. | 5 | 23 |
| 19:1438808-1438831 | 80 | + | GAAGTAGAGCAGAAGAAGAAGCG | 41. | 5 | 23 |
| 19:24250496-24250519 | 76 | - | GAGTCCAAGCAGTAGAGGAAGGG | 42. | 3 | 23 |
| 12:73504668-73504691 | 74 | - | GAGTTAGAGCAGAAAAAAAATGG | 43. | 4 | 23 |
| 11:62365266-62365289 | 72 | - | GAATCCAAGCAGAAGAAGAGAAG | 44. | 4 | 23 |
| 14:75723901-75723924 | 72 | - | AGTTCCAAGCAGAGGAAGAAGGG | 45. | 5 | 23 |
| 10:58848711-58848734 | 70 | + | GAGCACGAGCAAGAGAAGAAGGG | 46. | 4 | 23 |
| 7:83262530-83262552 | 66 | - | AAGTCAGAG-AGAAGAAGAAGAG | 47. | 4 | 22 |
| 11:30301802-30301825 | 58 | - | CAGTCTGAGTAGAAGAAAAGGG | 48. | 4 | 23 |
| 5:9227145-9227168 | 58 | + | AAGTCTGAGCACAAGAAGAATGG | 49. | 3 | 23 |
| 5:146833183-146833206 | 58 | - | GAGCCGGAGCAGAAGAAGGAGGG | 50. | 3 | 23 |
| 6:9118792-9118815 | 56 | - | ACGTCTGAGCAGAAGAAGAATGG | 51. | 3 | 23 |
| 7:100895235-100895258 | 56 | - | CGCTCCGAGCAGAAGAAAGTGG | 52. | 5 | 23 |
| 8:26500632-26500655 | 54 | + | CCATCCGAGCAGGAGATTAATGG | 53. | 6 | 23 |
| 7:111475442-111475465 | 54 | - | GAGCCCAAGCACAAAAGAATGG | 54. | 4 | 23 |
| 4:87256685-87256708 | 52 | - | GAGTAAGAGAAGAAGAAGAAGGG | 55. | 3 | 23 |
| 9:34735034-34735057 | 52 | + | AAGTCCTAGCAGAAGGAAGGGG | 56. | 5 | 23 |
| 2:14945887-14945910 | 50 | - | AAGTCCAGGCAGGAGAAAAATGG | 57. | 5 | 23 |

TABLE 2-continued

| Chromosome:Start-End | Read | Strand | Off-target Sequence | SEQ ID NO: | Distance | Length |
|---|---|---|---|---|---|---|
| 19:56089509-56089532 | 48 | - | AAGGCCGAGCAGGAGGAAGAAGG | 58. | 6 | 23 |
| 4:44622959-44622982 | 46 | + | AAGTCTGAGAAGAAGAAGAAAGA | 59. | 4 | 23 |
| 4:60950632-60950655 | 46 | + | TATTCCAAGCAAAGAAAAAGGG | 60. | 5 | 23 |
| 2:163702353-163702376 | 44 | + | AAGCCCAAGCAGAAGAAAATGA | 61. | 5 | 23 |
| 17:78609059-78609082 | 40 | - | GAGCCCGTGCAGAGGAAGAAGGA | 62. | 4 | 23 |
| 3:45605380-45605403 | 36 | - | GAGTCCACACAGAAGAAGAAAGA | 63. | 4 | 23 |
| 3:149083982-149084005 | 36 | + | CTGTCCAAGCACAAGAACAATGG | 64. | 5 | 23 |
| 1:221522607-221522630 | 34 | + | GAGTTTGAGTAGAAGAAGAAGAG | 65. | 4 | 23 |
| 12:114102185-114102208 | 34 | + | AGGTCTGAGCAGAAGAAAGAAGG | 66. | 5 | 23 |
| 5:120294729-120294752 | 34 | - | ATGTCCAAGCACAAGAGGAATGG | 67. | 5 | 23 |
| 8:105164108-105164131 | 34 | + | GAGCCCAAGAAGAAGAAGAAGGA | 68. | 4 | 23 |
| 15:56583426-56583449 | 30 | + | AAGTCTGAGTAGGAGAAAAAGGG | 69. | 5 | 23 |
| 19:51616603-51616626 | 30 | - | AGGTCTGAGCAGAAGAGGAAGAG | 70. | 5 | 23 |
| 4:174898812-174898835 | 30 | - | TGATCCAAGCAGGAGAAAATGG | 71. | 6 | 23 |
| 3:123771739-123771762 | 30 | + | CATTCCTAGCAGAGGAAGAAAGG | 72. | 4 | 23 |
| 10:5401770-5401793 | 28 | + | TAATCCAATCAGAAGAAGAAGGG | 73. | 4 | 23 |
| 6:961042-961065 | 28 | + | AAATCCAACCAGAAGAAGAGGGG | 74. | 5 | 23 |
| 16:5501173-5501196 | 28 | - | CAATCAGAGCAGAGGAAGAAGAG | 75. | 5 | 23 |
| 2:200422147-200422170 | 26 | - | GAAGCCAAGCAGAAGAAAAACAG | 76. | 5 | 23 |
| 2:224569568-224569591 | 26 | + | GAGGCTGAGCAGAAGAGGAAGGA | 77. | 4 | 23 |
| 5:16467414-16467437 | 26 | - | TGTTCCAAGCAGAAGAGTAATGG | 78. | 6 | 23 |
| 8:10048559-10048582 | 26 | - | TAGTCTAAGCAGCAGAAGAATGG | 79. | 4 | 23 |
| 21:24667736-24667759 | 24 | - | CCCTCCAAGCAGAAGAAGATGAG | 80. | 6 | 23 |
| 3:13455177-13455200 | 24 | + | AGGCCCGAGCAGGAGAAAATAGG | 81. | 6 | 23 |
| 1:201617280-201617303 | 22 | - | AGCTCCGAGCAGAGGAAGGAGGG | 82. | 5 | 23 |
| 1:231750724-231750747 | 22 | + | GAGTCAGAGCAAAAGAAGTAGTG | 83. | 4 | 23 |
| 2:203707473-203707496 | 22 | - | GAGTTTAAGCAGAAGAAGAGAGG | 84. | 4 | 23 |
| 8:97023219-97023242 | 22 | + | TCTTCCAAGCAAAAGAAGAAAGA | 85. | 6 | 23 |
| 9:72006952-72006975 | 22 | - | GAGGCCCAGCAGAGGAAGAAGAG | 86. | 4 | 23 |
| 9:127309498-127309521 | 22 | - | AAGCCCAAGCAAATGAAGAATGG | 87. | 5 | 23 |
| 16:73177721-73177744 | 22 | + | TCTTCCGAGCTGAAGAAGAAAAG | 88. | 5 | 23 |
| 2:65782509-65782532 | 20 | + | GACTCCGAGCAGCAGAAGGATGG | 89. | 3 | 23 |
| 16:8265310-8265333 | 20 | + | GAGACCAAACAGAGGAAGAAGGG | 90. | 4 | 23 |
| 7:3812774-3812797 | 20 | - | GAGTCCTAGAAAAGAAGAGAGG | 91. | 4 | 23 |
| 7:70109949-70109972 | 20 | + | GAATCAGAGCAAAGGAGAAAGG | 92. | 4 | 23 |
| 1:209931582-209931605 | 18 | + | TTATCCGAGAAGAAGAAGTAAGG | 93. | 5 | 23 |
| 22:34302975-34302998 | 18 | + | AATTCCAAGCAGAAGAAAAAGGA | 94. | 5 | 23 |
| 8:102244534-102244557 | 18 | + | AGTTCCAAGCAGAAGAAGCATGG | 95. | 5 | 23 |

TABLE 2-continued

| Chromosome:Start-End | Read | Strand | Off-target Sequence | SEQ ID NO: | Distance | Length |
|---|---|---|---|---|---|---|
| 3:57591866-57591889 | 18 | + | AAGTCCAAGCACAAGAAACATGG | 96. | 5 | 23 |
| 17:54421036-54421059 | 16 | - | GAGTCCCAGGAGAAGAAGAGAGG | 97. | 3 | 23 |
| 2:66729755-66729778 | 16 | + | AGTTCAGAGCAGGAGAAGAATGG | 98. | 5 | 23 |
| 4:21141327-21141350 | 16 | - | AAGCCCGAGCAGAAGAAGTTGAG | 99. | 5 | 23 |
| 6:99699155-99699178 | 16 | - | GAGTTAGAGCAGAGGAAGAGAGG | 100. | 4 | 23 |
| 9:135663386-135663409 | 16 | + | CAGTCCAAACAGAAGAGGAATGG | 101. | 4 | 23 |
| X:53467704-53467727 | 16 | - | GAGTCCGGGAAGGAGAAGAAAGG | 102. | 3 | 23 |
| 21:32643345-32643368 | 16 | - | AAGGCAAAGCAAAGAAGAGGGG | 103. | 6 | 23 |
| 1:113741452-113741475 | 14 | + | GAGGTAGAGCAGAAGAAGAAGCG | 104. | 4 | 23 |
| 10:63704768-63704791 | 14 | - | AAGTCCCAGCAACAGAAGAAAGG | 105. | 4 | 23 |
| 12:119985924-119985947 | 14 | - | GACTCCTAGCAAAAGAAGAATGG | 106. | 3 | 23 |
| 19:44223469-44223492 | 14 | + | GAGGCCTTGCAGAAGAAGAAGGC | 107. | 4 | 23 |
| 20:23516684-23516707 | 14 | - | GAATCCCAGCAGGAGAGGAATGG | 108. | 4 | 23 |
| 5:53966504-53966527 | 14 | - | CAATCCGGGCAGAAGAAGGAGAG | 109. | 5 | 23 |
| 8:74634205-74634228 | 14 | - | AAGTCCAAAAGAAGAAAAAGG | 110. | 5 | 23 |
| 18:15077483-15077506 | 14 | + | TAGGCTGAGCAGAAGAAAAGGA | 111. | 5 | 23 |
| 14:38654648-38654671 | 12 | + | AAGTCTGAGAAGAAGAAGACATG | 112. | 5 | 23 |
| 14:50538462-50538485 | 12 | - | TAGTCCTAGCAAAAGCAGAAGGG | 113. | 4 | 23 |
| 4:131662215-131662237 | 12 | - | GAATCCAAG-AAGAAGAATGG | 114. | 3 | 22 |
| 6:40361640-40361663 | 12 | + | GAGTCTAAGCAGAAGAGGACTGG | 115. | 4 | 23 |
| 18:71029915-71029938 | 12 | - | GAGTCCCAGCAGGAGAAGAAAGA | 116. | 3 | 23 |
| 3:63468110-63468133 | 12 | + | AAGTTGGAGCAGGAGAAGAAGGG | 117. | 4 | 23 |
| 1:35385584-35385607 | 10 | + | GAAGTGGAGCAGGAGAAGAAGGG | 118. | 5 | 23 |
| 11:68772640-68772663 | 10 | - | GAGTCCATACAGGAGAAGAAAGA | 119. | 5 | 23 |
| 12:32650839-32650861 | 10 | - | GAGTC-GAGAAGAAGAAAAAGG | 120. | 3 | 22 |
| 12:70327491-70327514 | 10 | - | GAATCCCAGCAGGAGAAGACAGG | 121. | 4 | 23 |
| 13:27769640-27769663 | 10 | + | GAGTAGGAGCAGGAGAAGAAGGA | 122. | 4 | 23 |
| 14:20246485-20246507 | 10 | + | GAGTA-GAGCAGAGGAGGAAGGG | 123. | 4 | 22 |
| 14:94517597-94517620 | 10 | - | CTCTCCAAGCAGAAGAAGAAGAA | 124. | 6 | 23 |
| 17:74877554-74877577 | 10 | + | GAGGCCGGGCAGGAGAAGGAGGG | 125. | 4 | 23 |
| 19:16132593-16132616 | 10 | + | GCATCCAAGCAGGAGGAGAAGGG | 126. | 5 | 23 |
| 19:46265337-46265360 | 10 | - | AAGCCCAAGGAGAAGAAGAAAGG | 127. | 4 | 23 |
| 2:51907191-51907214 | 10 | + | AAGTCAAAGCAGGAGAAGAAAGA | 128. | 5 | 23 |
| 20:22037218-22037241 | 10 | - | GAGAGAGAGCAAAAAAGAAGGG | 129. | 5 | 23 |
| 20:48873417-48873440 | 10 | - | AAGCCCGGGCAGAAGAAGCACAG | 130. | 5 | 23 |
| 4:25060740-25060763 | 10 | - | GTGTCAGAGCAGAAAAAGAGTGG | 131. | 4 | 23 |
| 4:54651562-54651585 | 10 | - | CATTCCAAGCAGCAGAAGAAGAG | 132. | 5 | 23 |
| 5:82309812-82309835 | 10 | + | AAGTCCAAGCATAAGAAAACAGG | 133. | 5 | 23 |
| 8:37644281-37644304 | 10 | + | GAGAGAGAGCAGGAGAGGAAAGG | 134. | 5 | 23 |

TABLE 2 -continued

| Chromosome:Start-End | Read | Strand | Off-target Sequence | SEQ ID NO: | Distance | Length |
|---|---|---|---|---|---|---|
| 8:109199391-109199414 | 10 | - | GAGTCAGAGCAGAAGAAAGAGGA | 135. | 4 | 23 |
| 7:19457141-19457164 | 10 | - | ATCTCCAAGCAGAAGAAAAATGG | 136. | 5 | 23 |

Figure 4A:
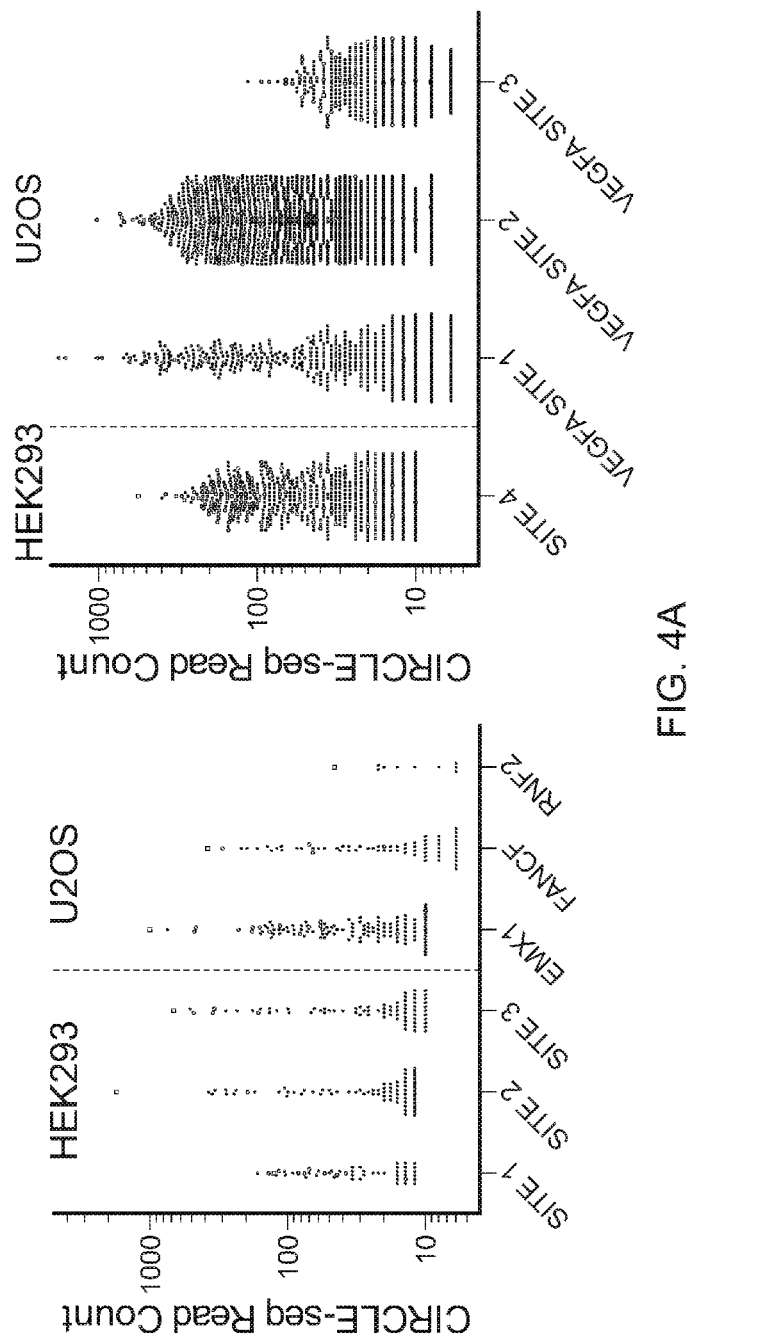

Example 4. Mutation of Off-Target Sites Identified by CIRCLE-Seq in Human Cells An important question raised by our experiments is whether the novel off-target cleavage sites identified in vitro by CIRCLE-seq (and not by GUIDE-seq or HTGTS) are actually mutated in cells by Cas9/gRNA complexes. Given that many of the off-target sites detected by both CIRCLE-seq and GUIDE-seq have high numbers of CIRCLE-seq sequencing read counts (FIG. 4A), this strongly suggests GUIDE-seq is mostly detecting sites that are efficiently cleaved in vitro. By contrast, the off-target sites found only by CIRCLE-seq have lower CIRCLE-seq read counts (FIG. 4A), suggesting that these might be missed by GUIDE-seq because they are cleaved at lower frequencies. If this were correct, we would expect it to be difficult to validate these sites in cells using standard targeted amplicon sequencing because the error rate of next-generation sequencing places a floor for indel mutation detection of approximately 0.1%.

Figure 4B:
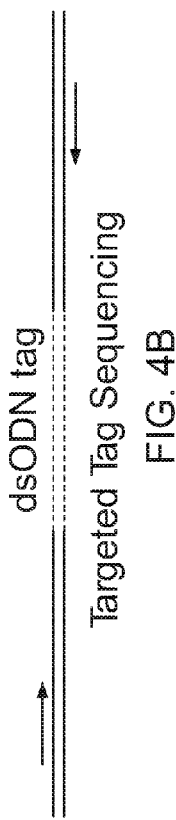
Figure 4C:
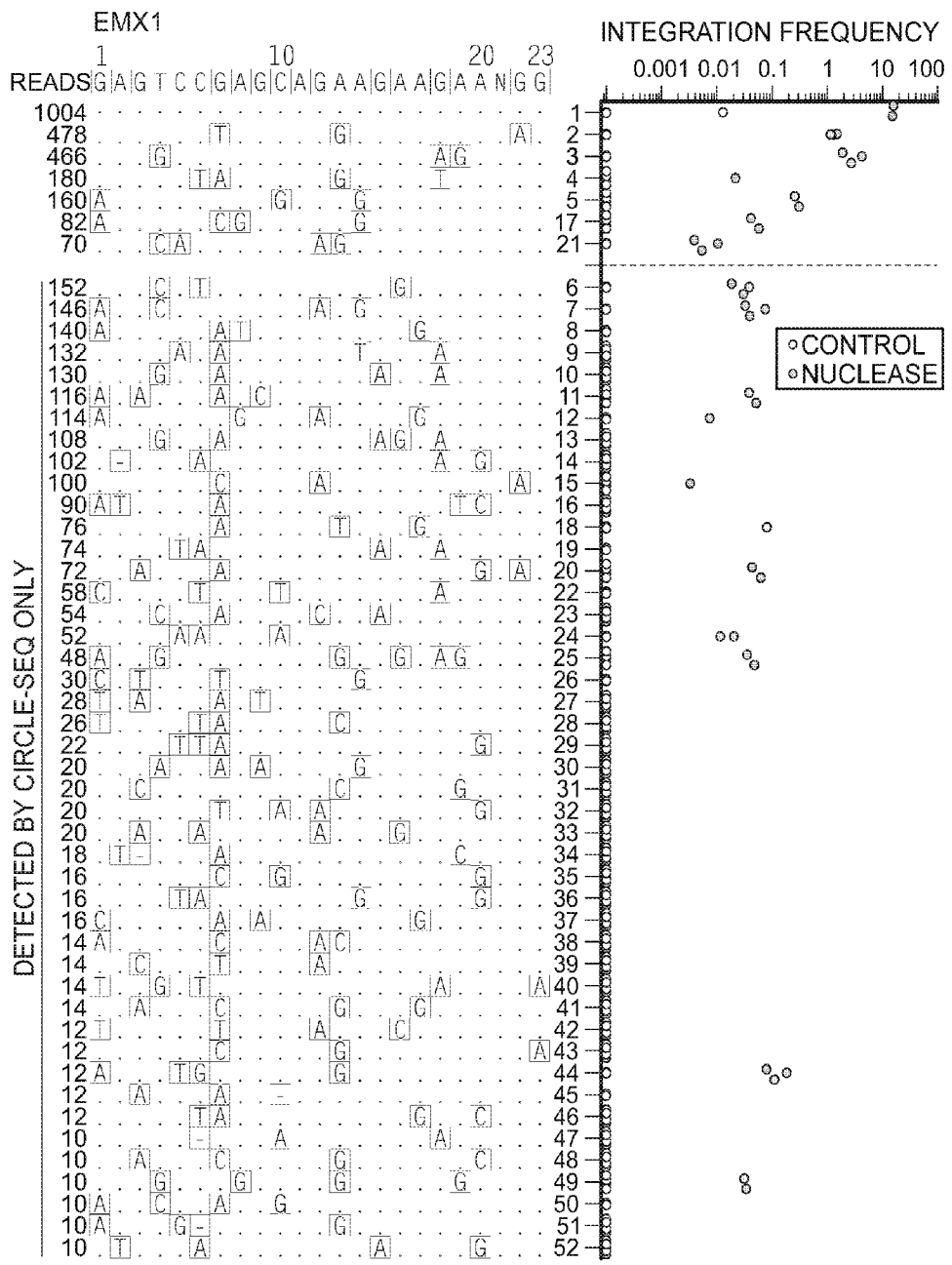
Figure 4D:
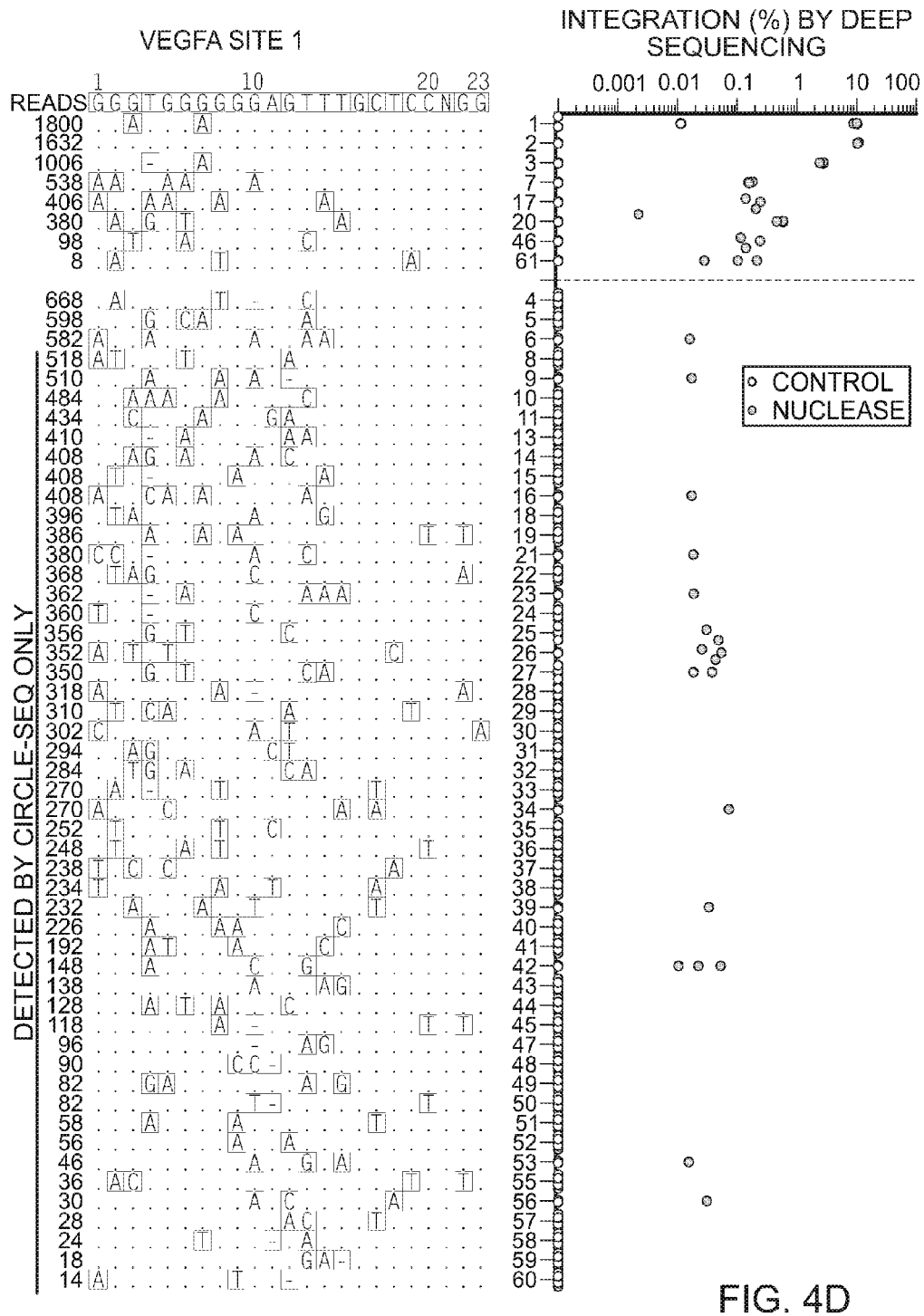

To determine whether the novel off-target sites revealed only by CIRCLE-seq (but not in our original GUIDE-seq experiments) might be cleaved in human cells, we reasoned that we could perform high depth targeted amplicon sequencing using genomic DNA obtained from cell-based GUIDE-seq experiments and look for tag integration as evidence for off-target Cas9 cleavage (FIG. 4B). This strategy sidesteps the problem of the indel error rate associated with deep sequencing because tag integration occurs with a negligible background frequency. Using this targeted tag integration sequencing approach, we examined a total of 98 off-target sites found by CIRCLE-seq (but not by GUIDE-seq) with SpCas9 for the EMX1 and VEGFA site 1 gRNAs. We chose sites that had a range of CIRCLE-seq read counts and/or number of mismatches relative to the on-target site. As positive controls for the tag integration assay, we also selected a smaller set of off-target sites that exhibited variable CIRCLE-seq read counts and that had been found by both CIRCLE-seq and GUIDE-seq. Targeted amplicon sequencing revealed detection of the dsODN tag at all of the control off-target sites, with frequencies that correlated well with GUIDE-seq read counts (FIGS. 4C and 4D). Notably, we also detected dsODN tag integration at 24 of the 98 novel off-target sites identified only by CIRCLE-seq (FIGS. 4C-E), with frequencies in the low range (0.003-0.2%) as anticipated. The locations of all 24 of these tag integrations map to the expected position in the protospacer complementarity region, 3 bps away from the PAM sequence, consistent with these sites representing bona fide off-target cleavage sites (FIG. 4F).

Figure 4G:
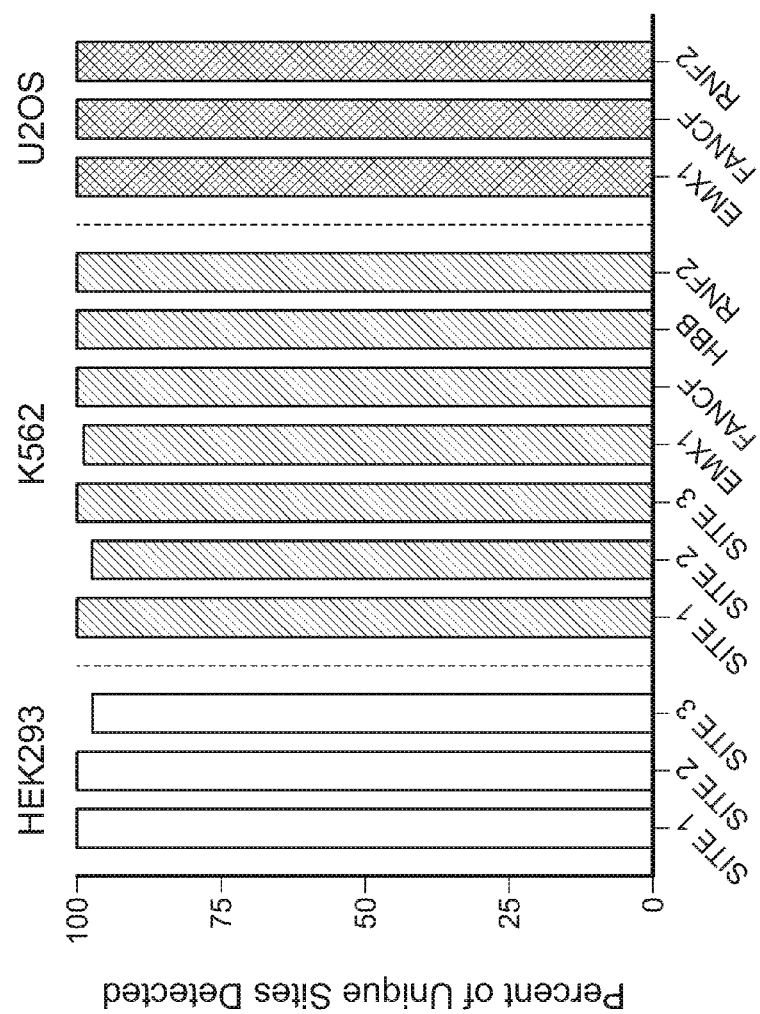

Example 5. Reference Genome-Independent Off-Target Site Discovery by CIRCLE-Seq Because each pair of CIRCLE-seq reads from a single DNA molecule yields sequences from both sides of a CRISPR-Cas9 nuclease cleavage site, we reasoned that the method might be used to identify off-target sites even without a reference genome sequence. To this end, we developed a mapping-independent off-target site discovery algorithm that merges paired-end reads in an end-to-end orientation and directly searches for off-target cleavage sites that resemble the on-target site (see Materials and Methods). Using this algorithm, we identified on average ~99.5% of CIRCLE-seq sites with more than 10 CIRCLE-seq reads detected by our standard reference-based mapping algorithm (FIG. 4G). This result demonstrates that CIRCLE-seq can be used in a reference-independent fashion to identify off-target cleavage sites for organisms whose genome sequences are less well-characterized and/or show high genetic variability (e.g., non-inbred species in the wild).

Example 6. Association of CIRCLE-Seq Off-Target Sites with SNPs

Figure 5A:
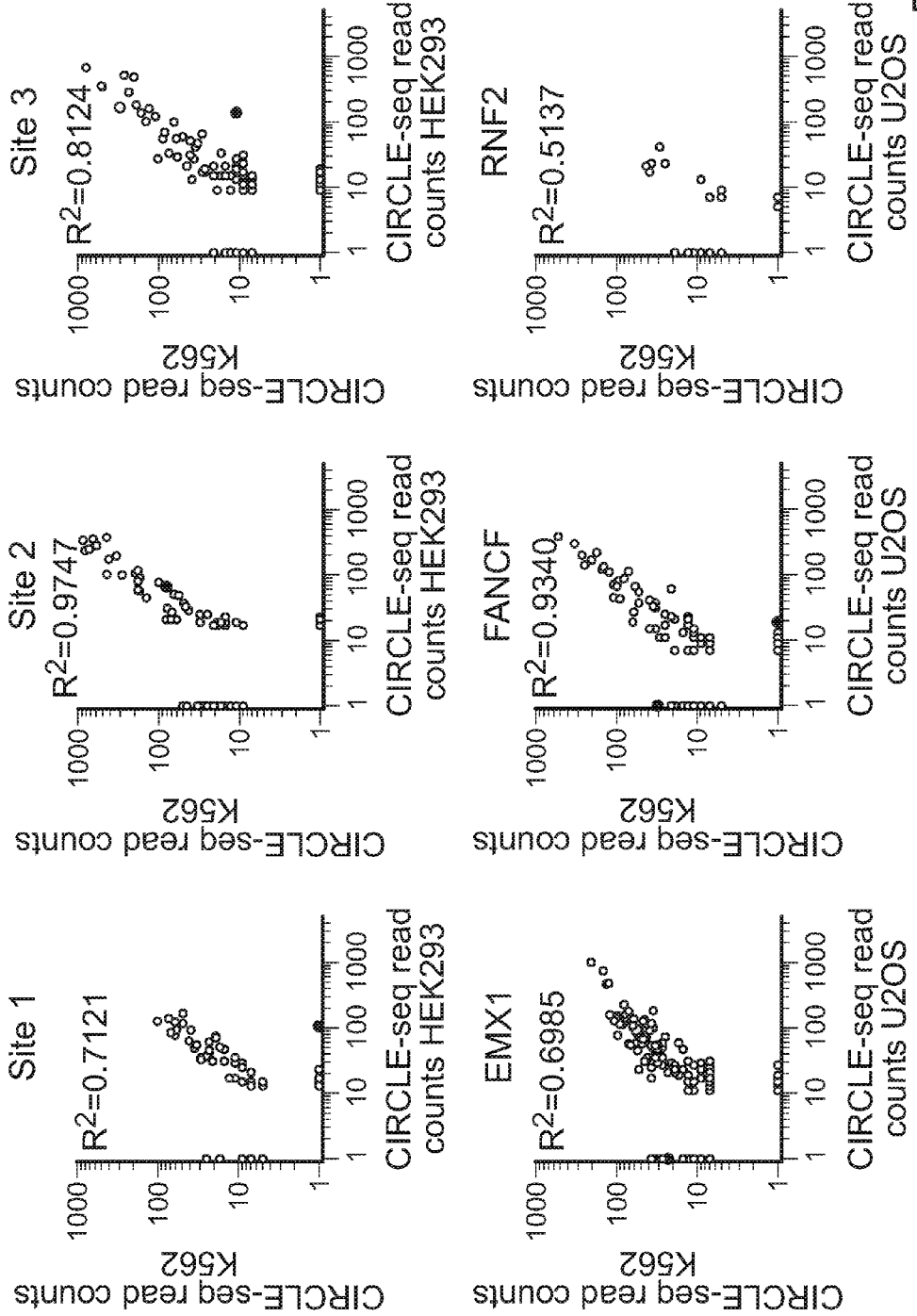
Figure 5B:
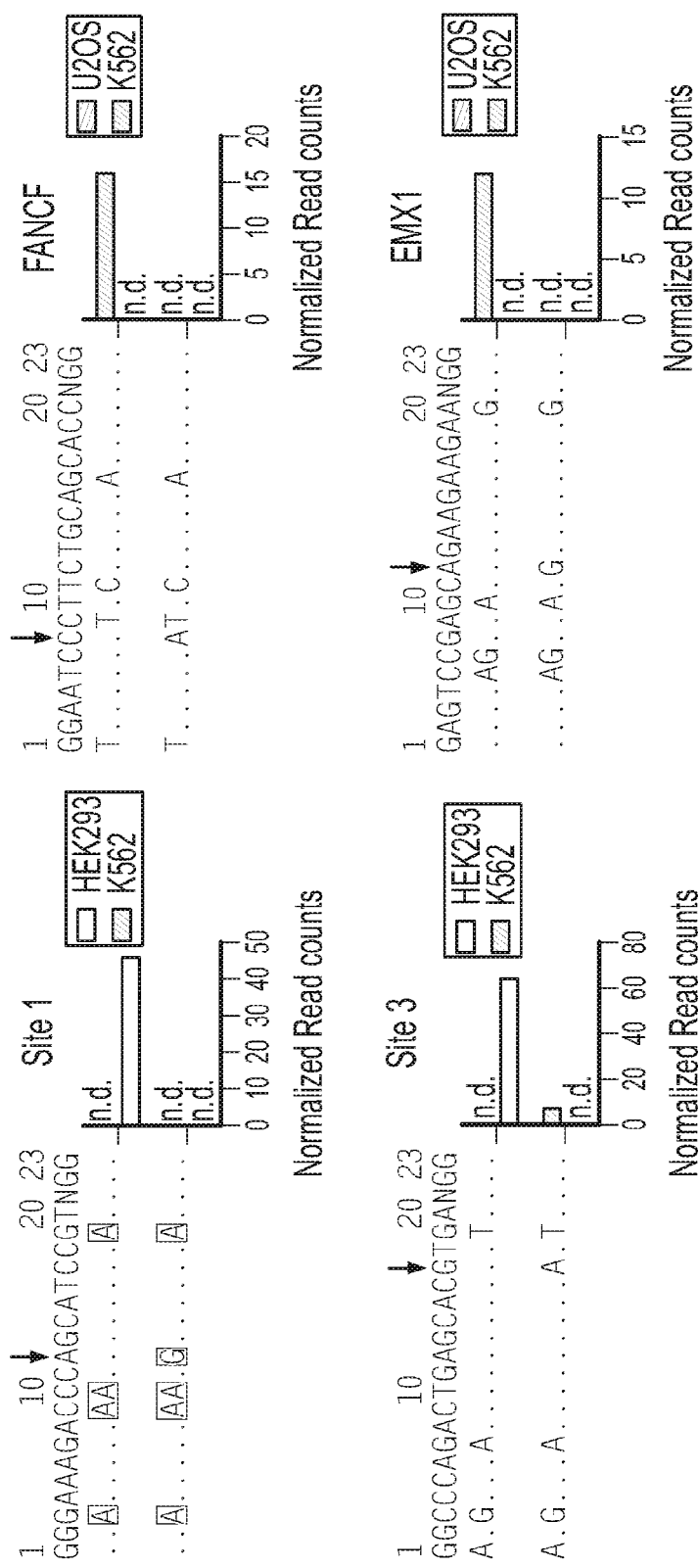

With its higher throughput and ease of reproducibility, an in vitro method such as CIRCLE-seq provides the opportunity to define patient-specific off-target profiles for any given Cas9/gRNA nuclease. A previous study identified a single example of a SNP influencing off-target cleavage[36]. To more broadly test whether genetic differences can influence nuclease-induced off-target cleavage, we performed additional CIRCLE-seq experiments on human K562 genomic DNA with six gRNAs we had already assessed on human HEK293 and U2OS genomic DNAs (three gRNAs on HEK293s and three on U2OS). Although many off-target sites for these gRNAs showed correlated CIRCLE-seq read counts on DNA from both cell types tested, we also observed 55 sites that were preferentially cleaved only in one cell type or the other (FIG. 5A). Examination revealed that eight off-target cleavage sites harbored non-reference single-nucleotide polymorphisms (SNPs) that might account for some of these observed cell-type specific differences in cleavage efficiencies (FIG. 5B). Interestingly, these SNPs were observed in regions of protospacer complementarity as well as within the PAM and were predicted to either increase or decrease cleavage of the site relative to the reference genome sequence (FIG. 5B).

Having identified additional examples where SNPs appear to influence cleavage efficiencies at off-target sites, we next sought to estimate how frequently SNPs might be expected to impact off-target cleavage efficiency. To do this, we examined the genotypes of 2504 individuals from the 1000 Genomes Project[37] at all 1247 off-target sites we detected for the six gRNAs (targeted to standard non-repetitive sequences) we had assessed by CIRCLE-seq. We found, on average, non-reference genetic variation in ~2.5% of these off-target sites (FIG. 5C). At a population level, we found that superpopulations contained genetic variation in an average of ~20% of these off-target sites (FIG. 5C). In addition, 50% of these off-target sites contained non-reference genetic variation for at least one individual sequenced in the 1000 Genomes Project (FIG. 5C). These frequencies are consistent with the expectation that, given existence of ~100 million validated human SNPs in the most recent version of dbSNP[38], one might expect to find a SNP in ~69% of SpCas9 off-target sites in the human genome. As expected, the range of mismatches observed at the off-target sites we examined is increased when considering diverse individual genotypes from the 1000 genomes project (FIG. 5D). Interestingly, for approximately 9% of the off-target site haplotypes, the numbers of mismatches relative to the reference genome is decreased which would predict a potential increase in off-target cleavage risk at these sites (FIG. 5E). Taken together, these results highlight the importance of individual genetic variation for off-target analysis and highlight how CIRCLE-seq might be used to produce personalized genome-wide off-target profiles.

Example 7. Exemplary CIRCLE-Seq Protocols

Described herein are exemplary protocols for an in vitro assay for finding cleavage sites of CRISPR/Cas9 nuclease from complex genomic DNA mixtures.

Materials

The following materials were used in Protocol 1.

| Materials | Vendor | Model Number |
|---|---|---|
| HTP Library Preparation Kit | Kapa Biosystems | KK8235 |
| Hifi HotStart ReadyMix, 100 × 25 μL reactions | Kapa Biosystems | KK2602 |
| Lambda exonuclease (5 U/ul) | NEB | M0262L |
| E. Coli Exonuclease I (20 U/ul) | NEB | M0293S |
| USER enzyme (1000 U/ul) | NEB | M5505L |
| T4 PNK (10000 U/ul) | NEB | M0201S |
| Cas9 enzyme (1000 nM) | NEB | M0386L |
| Ampure XP 60 ml | Agencourt | A63881 |

| Protocol 1 | |
|---|---|
| Component | 1 rxn (ul) |
| 1. End Repair | |
| Water | 8 |
| 10X Kapa End Repair Buffer | 7 |
| Kapa End Repair Enzyme Mix | 5 |
| Total master mix volume | 20 |
| Input DNA (0.1-5 ug) sheared to an average of about 300 bp | 50 |
| Total reaction volume | 70 |
| Incubate 30 minutes at 20 C. | |
| 1.7X SPRI cleanup using 120 ul Ampure XP beads. | |
| 2. A-tailing | |
| 10X Kapa A-Tailing Buffer | 5 |
| Kapa A-Tailing Enzyme | 3 |
| Total master mix volume | 8 |
| TE (0.1 mM EDTA) | 42 |
| End repaired DNA with beads | 0 |
| Total reaction volume | 50 |
| Incubate for 30 min at 30 C. | |
| Cleanup by adding 90 ul of SPRI solution. | |
| 3. 5' Adapter Ligation | |
| 5X Kapa Ligation Buffer | 10 |
| Kapa T4 DNA Ligase | 5 |
| Total master mix volume | 15 |
| A-tailed DNA with beads | 0 |

| Protocol 1 | |
|---|---|
| Component | 1 rxn (ul) |
| TE (0.1 mM EDTA) | 30 |
| Stem-Loop Adapter (SEQ ID NO: 1) (40 uM) | 5 |
| Total reaction volume | 50 |
| Incubate for 1 hour at 20 C. | |
| Cleanup by adding 50 ul of SPRI solution. | |
| Proceed with 1 ug of 5' Adapter-ligated DNA into next step. | |
| 4. Lambda Exonuclease/E. Coli Exonuclease treatment | |
| 10X ExoI buffer | 5 |
| Lambda exonuclease (5U/ul) | 4 |
| E. Coli Exonuclease I (20U/ul) | 1 |
| Total master mix volume | 10 |
| Adapter-ligated DNA with beads | 0 |
| TE (0.1 mM EDTA) | 40 |
| Total reaction volume | 50 |
| Incubate for 1 hour at 37 C., 75 C. for 10 min. | |
| Cleanup by adding 90 ul of 1X Ampure XP beads. | |
| 5. USER/T4 PNK treatment | |
| 10X T4 DNA ligase buffer | 5 |
| USER enzyme | 3 |
| T4 PNK | 2 |
| Total master mix volume | 10 |
| Adapter-ligated DNA with beads | 0 |
| TE (0.1 mM EDTA) | 40 |
| Total reaction volume | 50 |
| Incubate for 1 hour at 37 C. | |
| Cleanup by adding 90 ul of SPRI solution. | |
| 6. Intramolecular Circularization | |
| 10X T4 DNA ligase buffer | 10 |
| T4 DNA ligase (400U/ul) | 2 |
| H2O | 8 |
| Total master mix volume | 20 |
| Adapter-ligated, USER/T4 PNK-treated DNA (500 ng) | 80 |
| Total reaction volume | 100 |
| Incubate overnight (16 hours) at 16 C. | |
| Cleanup by adding 100 ul of Ampure XP beads | |
| 7. PlasmidSafe Exonuclease treatment | |
| 10X PlasmidSafe Buffer | 5 |
| 25 mM ATP | 2 |
| PlasmidSafe enzyme | 5 |
| Total master mix volume | 12 |
| Adapter-ligated DNA with beads | 0 |
| TE (0.1 mM EDTA) | 38 |
| Total reaction volume | 50 |
| Incubate for 1 hour at 37 C., 70 C. for 30 min. | |
| Cleanup by adding 50 ul of 1X Ampure XP beads. | |
| 8. Cleavage by Cas9 | |
| Water | 63 |
| 10X Cas9 buffer | 10 |
| Cas9 (1 uM -> 900 nM final) | 9 |
| sgRNA (300 nM, ~100 ng/ul) | 3 |
| Total reaction volume | 85 |
| Incubate at room temperature for 10 minutes. | |
| DNA (~400 bp, 250 ng) | 15 |
| Incubate for 1 hour at 37 C. | |
| Purify with 1X SPRI bead cleanup (100 ul). | |

Protocol 1 -continued

| Component | 1 rxn (ul) |
|---|---|
| 9. A-tailing | |
| 10X Kapa A-Tailing Buffer | 5 |
| Kapa A-Tailing Enzyme | 3 |
| Total master mix volume | 8 |
| TE (0.1 mM EDTA) | 42 |
| End repaired DNA with beads | 0 |
| Total reaction volume | 50 |

Incubate for 30 min at 30 C.
Cleanup by adding 90 ul of SPRI solution.

10. 3' Adapter Ligation

| | |
|---|---|
| 5X Kapa Ligation Buffer | 10 |
| Kapa T4 DNA Ligase | 5 |
| Total master mix volume | 15 |
| A-tailed DNA with beads | 0 |
| TE (0.1 mM EDTA) | 30 |
| NEBNext Adapter (15 uM) | 5 |
| Total reaction volume | 50 |

Incubate for 30 minutes at 20 C.
Cleanup by adding 50 ul of SPRI solution.

11. USER enzyme treatment

Add 3 ul of USER enzyme and treat for 60 minutes at 37 C.
(Treatment is in TE 10 mM Tris, 0.1 mM EDTA.)
Purify with 1X SPRI solution (50 ul).

9. PCR Amplification

| Reagent | Vendor |
|---|---|
| Gentra Puregene Tissue Kit | Qiagen |
| Qubit dsDNA BR Assay Kit | Thermo Fisher |
| Agencourt AMPure XP magnetic beads | Beckman Coulter |
| High throughput, "with bead", PCR-free Library Preparation Kit | KAPA Biosystems |
| Enzymes and buffers | New England Biolabs |
| Lamda exonuclease | |
| Exonuclease I (E. coli) | |
| USER enzyme | |
| T4 polynucleotide kinase | |
| T4 DNA Ligase | |
| Cas9 nuclease, S. pyogenes | |
| Plasmid-Safe ™ ATP-Dependent DNase | Epicentre |
| MEGAshortscript ™ Kit | Thermo Fisher |
| NEBNext ® Multiplex Oligos for Illumina ® (Dual Index Primers Set 1) | New England Biolabs |
| KAPA HiFi HotStart ReadyMix | KAPA Biosystems |
| ddPCR ™ Library Quantification Kit for Illumina TruSeq | Bio-Rad |
| KAPA Library Quantification Kit for NGS (Universal) | KAPA Biosystems |

CIRCLE-Seq Hairpin Adapter oSQT1288/5Phos/CGGTGGACCGATGATC/ideoxyU/
ATCGGTCCACCG*T Annealing Program: 95° C. for 5 min, −1° C./min for 70 cycles, hold at 4° C.

Input Quantification and Shearing

1. Genomic DNA is sheared to an average length of 300 bp according to the standard operating protocol for the Covaris S2.
2. Sheared DNA is cleaned up with 1.8× Ampure XP SPRI beads according to manufacturer protocol, and eluted in 35 μl of 1× TE buffer.

End-Repair

1. For each end-repair reaction:

| Component | Volume |
|---|---|
| Nuclease-free H$_2$O | 8 μl |
| KAPA End Repair Buffer (10X) | 7 μl |
| KAPA End Repair Enzyme Mix | 5 μl |
| Total Master Mix | 20 μl |
| Sheared genomic DNA (5 μg) (from step 2) | 50 μl |
| Total | 70 μl |

End Repair Program: 20° C. for 30 min, hold at 4° C.

2. 1.7×SPRI cleanup (120 μl of Agencourt Ampure XP beads), elute in 42 μl of 1× TE buffer.

A-Tailing

1. For each A-tailing reaction:

| Component | Volume |
|---|---|
| KAPA A-tailing Buffer (10X) | 5 μl |
| KAPA A-tailing Enzyme | 3 μl |
| Total Master Mix | 8 μl |
| End Repaired DNA with beads (from step 4) | 42 μl |
| Total | 50 μl |

A-tailing Program: 30° C. for 30 min, hold at 4° C.

2. 1.8×SPRI cleanup (90 μl of PEG/NaCl SPRI Solution), elute in 30 μl of 1× TE buffer.

Adapter Ligation

1. For each ligation reaction to annealed adapter oSQT1288:

| Component | Volume |
|---|---|
| KAPA Ligation Buffer (5×) | 10 μl |
| KAPA T4 DNA Ligase | 5 μl |
| Annealed Hairpin Adapter oSQT1288 (40 μM) | 5 μl |
| Total Master Mix | 20 μl |
| A-tailed DNA with beads (from step 6) | 30 μl |
| Total | 50 μl |

Ligation Program: 20° C. for 1 hr, hold at 4° C.

2. 1×SPRI cleanup (50 μl of PEG/NaCl SPRI Solution), elute in 30 μl of 1× TE buffer.

Enzymatic Treatments
Lambda Exonuclease/Exonuclease I (*E. coli*) Treatment
1.

| Component | Volume |
| --- | --- |
| Exonuclease I Reaction Buffer (10X) | 5 µl |
| Lambda Exonuclease (5 U/µl) | 4 µl |
| Exonuclease I (*E. coli*) (20 U/µl) | 1 µl |
| Total Master Mix | 10 µl |
| Adapter ligated DNA (1 µg) (from step 8) | 40 µl |
| Total | 50 µl |

Incubation Program: 37° C. for 1 hr, 75° C. for 10 min, hold at 4° C.
2. 1.8×SPRI cleanup (90 µl of Agencourt Ampure XP beads), elute in 40 µl of 1× TE buffer.

USER/T4 PNK Treatment
1.

| Component | Volume |
| --- | --- |
| T4 DNA Ligase Buffer (10X) | 5 µl |
| USER Enzyme (1 U/µl) | 3 µl |
| T4 Polynucleotide Kinase (10 U/µl) | 2 µl |
| Total Master Mix | 10 µl |
| Lambda Exonuclease/Exonuclease I treated DNA with beads (from step 10) | 40 µl |
| Total | 50 µl |

Incubation Program: 37° C. for 1 hr, hold at 4° C.
2. 1.8×SPRI cleanup (90 µl of PEG/NaCl SPRI Solution), elute in 35 µl of 1× TE buffer.

Intramolecular Circularization
1.

| Component | Volume |
| --- | --- |
| Nuclease-free H₂O | 8 µl |
| T4 DNA Ligase Buffer (10X) | 10 µl |
| T4 DNA Ligase (400 U/µl) | 2 µl |
| Total Master Mix | 20 µl |
| USER/T4 PNK treated DNA (500 ng) (from step 12) | 80 µl |
| Total | 100 µl |

Circularization Program: 16° C. for 16 hrs.
2. 1×SPRI cleanup (100 µl of Agencourt Ampure XP beads), elute in 38 µl of 1× TE buffer.

Plasmid-Safe ATP-Dependent DNase Treatment
1.

| Component | Volume |
| --- | --- |
| Plasmid-Safe Reaction Buffer (10X) | 5 µl |
| ATP (25 mM) | 2 µl |
| Plasmid-Safe ATP-Dependent DNase (10 U/µl) | 5 µl |
| Total Master Mix | 12 µl |
| Circularized DNA (from step 14) | 38 µl |
| Total | 50 µl |

Incubation Program: 37° C. for 1 hr, 70° C. for 30 min, hold at 4° C.
2. 1×SPRI cleanup (50 µl of Agencourt Ampure XP beads), elute in 15 µl of 1× TE buffer.

In Vitro Digestion with Cas9 and gRNA
1.

| Component | Volume |
| --- | --- |
| Cas9 Nuclease Reaction Buffer (10X) | 10 µl |
| Cas9 Nuclease, *S. pyogenes* (1 µM) | 9 µl |
| In Vitro Transcribed guide RNA (3000 nM) | 3 µl |
| Total Master Mix | 22 µl |
| Incubate at room temperature for 10 min. | |
| Plasmid-Safe DNase Treated DNA (250 ng) (from step 16) | 78 µl |
| Total | 100 µl |

Digestion Program: 37° C. for 1 hr, hold at 4° C.
2. 1)(SPRI cleanup (100 µl of Agencourt Ampure XP beads), elute in 42 µl of 1× TE buffer.

A-Tailing
1.

| Component | Volume |
| --- | --- |
| KAPA A-tailing Buffer (10X) | 5 µl |
| KAPA A-tailing Enzyme | 3 µl |
| Total Master Mix | 8 µl |
| Cas9/gRNA digested DNA with beads (from step 18) | 42 µl |
| Total | 50 µl |

A-tailing Program: 30° C. for 30 min, hold at 4° C.
2. 1.8×SPRI cleanup (90 µl of PEG/NaCl SPRI Solution), elute in 30 µl of 1× TE buffer.

Adapter Ligation
1.

| Component | Volume |
| --- | --- |
| KAPA Ligation Buffer (5X) | 10 µl |
| KAPA T4 DNA Ligase | 5 µl |
| NEBNext Adaptor for Illumina (15 µM)* | 10 µl |
| Total Master Mix | 25 µl |
| A-tailed DNA with beads (from step 20) | 25 µl |
| Total | 50 µl |

*NEBNext Adaptor for Illumina (#E7601A):
5'-/5Phos/GATCGGAAGAGC ACACGTCTGAACTCCAGTC/ideoxyU/ACACTCT TTCCTACACGACGCTCTTCCGAT C*T-3

Ligation Program: 20° C. for 1 hr, hold at 4° C.
2. 1×SPRI cleanup (50 µl of PEG/NaCl SPRI Solution), elute in 47 µl of 1× TE buffer.

USER Enzyme Treatment
1. Add 3 µl of USER Enzyme (1 U/µ1) to the adapter ligated DNA with beads (from step 22).
2. 0.7×SPRI cleanup (35 µl of PEG/NaCl SPRI Solution), elute in 20 µl of 1× TE buffer.

PCR
1.

| Component | Volume |
|---|---|
| Nuclease-free H$_2$O | 5 μl |
| KAPA HiFi HotStart ReadyMix | 25 μl |
| Total Master Mix | 30 μl |
| NEBNext i5 Primer (10 μM) | 5 μl |
| NEBNext i7 Primer (10 μM) | 5 μl |
| USER enzyme treated DNA (20 ng) (from step 24) | 10 μl |
| Total | 50 μl |

PCR Program: 98° C. for 45 s, 22 cycles of (98° C. for 15 s, 65° C. for 30 s, 72° C. for 30 s), 72° C. for 1 min, hold at 4° C.

2. 0.7×SPRI cleanup (35 μl of Agencourt Ampure XP beads), elute in 30 μl of 1× TE buffer.

Library Quantification
1. Quantify the library using ddPCR Library Quantification Kit for Illumina TruSeq (Bio-Rad) on QX200 Droplet Digital PCR instrument, according to the manufacturer instructions. An alternative quantification method is using KAPA Library Quantification Kit for Next-Generation Sequencing (KAPA Biosystems), according to the manufacturer instructions.

REFERENCES

1. Cong, L. et al. Multiplex genome engineering using CRISPR/Cas systems. Science 339, 819-823 (2013).
2. Hwang, W. Y. et al. Efficient genome editing in zebrafish using a CRISPR-Cas system. Nat Biotechnol 31, 227-229 (2013).
3. Jinek, M. et al. RNA-programmed genome editing in human cells|eLife. Elife 2, e00471 (2013).
4. Mali, P. et al. RNA-guided human genome engineering via Cas9. Science 339, 823-826 (2013).
5. Jinek, M. et al. A Programmable Dual-RNA-Guided DNA Endonuclease in Adaptive Bacterial Immunity. Science 337, 816-821 (2012).
6. Doudna, J. A. & Charpentier, E. Genome editing. The new frontier of genome engineering with CRISPR-Cas9. Science 346, 1258096 (2014).
7. Bolukbasi, M. F., Gupta, A. & Wolfe, S. A. Creating and evaluating accurate CRISPR-Cas9 scalpels for genomic surgery. Nat Meth 13, 41-50 (2016).
8. Mali, P., Esvelt, K. M. & Church, G. M. Cas9 as a versatile tool for engineering biology. Nat Meth 10, 957-963 (2013).
9. Sander, J. D. & Joung, J. K. CRISPR-Cas systems for editing, regulating and targeting genomes. Nat Biotechnol 32, 347-355 (2014).
10. Maeder, M. L. & Gersbach, C. A. Genome-editing Technologies for Gene and Cell Therapy. Mol Ther 24, 430-446 (2016).
11. Lin, J. & Musunuru, K. Genome Engineering Tools for Building Cellular Models of Disease. FEBS J (2016). doi:10.1111/febs.13763
12. Hsu, P. D., Lander, E. S. & Zhang, F. Development and applications of CRISPR-Cas9 for genome engineering. Cell 157, 1262-1278 (2014).
13. Brandsma, I. & Gent, D. C. Pathway choice in DNA double strand break repair: observations of a balancing act. Genome Integr 3, 9 (2012).
14. Symington, L. S. & Gautier, J. Double-strand break end resection and repair pathway choice. Annu. Rev. Genet. 45, 247-271 (2011).
15. Kass, E. M. & Jasin, M. Collaboration and competition between DNA double-strand break repair pathways. FEBS Letters 584, 3703-3708 (2010).
16. Wyman, C. & Kanaar, R. DNA double-strand break repair: all's well that ends well. Annu. Rev. Genet. 40, 363-383 (2006).
17. Rouet, P., Smih, F. & Jasin, M. Introduction of double-strand breaks into the genome of mouse cells by expression of a rare-cutting endonuclease. Mol Cell Biol 14, 8096-8106 (1994).
18. Sternberg, S. H., LaFrance, B., Kaplan, M. & Doudna, J. A. Conformational control of DNA target cleavage by CRISPR-Cas9. Nature 527, 110-113 (2015).
19. Kiani, S. et al. Cas9 gRNA engineering for genome editing, activation and repression. Nat Meth 1-6 (2015). doi:10.1038/nmeth.3580
20. Dahlman, J. E. et al. Orthogonal gene knockout and activation with a catalytically active Cas9 nuclease. Nat Biotechnol 1-4 (2015). doi:10.1038/nbt.3390
21. Fu, Y, Sander, J. D., Reyon, D., Cascio, V. M. & Joung, J. K. Improving CRISPR-Cas nuclease specificity using truncated guide RNAs. Nat Biotechnol (2014). doi:10.1038/nbt.2808
22. Anders, C., Niewoehner, O., Duerst, A. & Jinek, M. Structural basis of PAM-dependent target DNA recognition by the Cas9 endonuclease. Nature (2014). doi:10.1038/nature13579
23. Shah, S. A., Erdmann, S., Mojica, F. J. M. & Garrett, R. A. Protospacer recognition motifs: mixed identities and functional diversity. RNA Biol 10, 891-899 (2013).
24. Tsai, S. Q. & Joung, J. K. Defining and improving the genome-wide specificities of CRISPR-Cas9 nucleases. Nature 17, 300-312 (2016).
25. Bolukbasi, M. F., Gupta, A. & Wolfe, S. A. Creating and evaluating accurate CRISPR-Cas9 scalpels for genomic surgery. Nat Meth 13, 41-50 (2015).
26. Gori, J. L. et al. Delivery and Specificity of CRISPR-Cas9 Genome Editing Technologies for Human Gene Therapy. Hum Gene Ther 26, 443-451 (2015).
27. Cox, D. B. T., Platt, R. J. & Zhang, F. Therapeutic genome editing: prospects and challenges. Nat Med 21, 121-131 (2015).
28. Gabriel, R. et al. An unbiased genome-wide analysis of zinc-finger nuclease specificity. Nat Biotechnol 29, 816-823 (2011).
29. Ran, F. A. et al. In vivo genome editing using *Staphylococcus aureus* Cas9. Nature 520, 186-191 (2015).
30. Tsai, S. Q. et al. GUIDE-seq enables genome-wide profiling of off-target cleavage by CRISPR-Cas nucleases. Nat Biotechnol 33, 187-197 (2015).
31. Frock, R. L. et al. Genome-wide detection of DNA double-stranded breaks induced by engineered nucleases. Nat Biotechnol 33, 179-186 (2015).
32. Crosetto, N. et al. Nucleotide-resolution DNA double-strand break mapping by next-generation sequencing. Nat Meth 10, 361-365 (2013).
33. Pattanayak, V. et al. High-throughput profiling of off-target DNA cleavage reveals RNA-programmed Cas9 nuclease specificity. Nat Biotechnol 31, 839-843 (2013).
34. Kim, D. et al. Digenome-seq: genome-wide profiling of CRISPR-Cas9 off-target effects in human cells. Nat Meth (2015). doi:10.1038/nmeth.3284
35. Kim, D., Kim, S., Kim, S., Park, J. & Kim, J.-S. Genome-wide target specificities of CRISPR-Cas9 nucleases revealed by multiplex Digenome-seq. Genome Res gr.199588.115 (2016). doi:10.1101/gr.199588.115

36. Yang, L. et al. Targeted and genome-wide sequencing reveal single nucleotide variations impacting specificity of Cas9 in human stem cells. Nature Communications 5, 5507 (2014).

37. 1000 Genomes Project Consortium et al. A global reference for human genetic variation. Nature 526, 68-74 (2015).

38. Sherry, S. T. et al. dbSNP: the NCBI database of genetic variation. Nucleic Acids Res 29, 308-311 (2001).

39. ENCODE Project Consortium. An integrated encyclopedia of DNA elements in the human genome. Nature 489, 57-74 (2012).

40. Li, H. & Durbin, R. Fast and accurate long-read alignment with Burrows-Wheeler transform. Bioinformatics 26, 589-595 (2010).

41. Li, H. A statistical framework for SNP calling, mutation discovery, association mapping and population genetical parameter estimation from sequencing data. Bioinformatics 27, 2987-2993 (2011).

42. Li, H. et al. The Sequence Alignment/Map format and SAMtools. Bioinformatics 25, 2078-2079 (2009).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a library of covalently closed circular double-stranded DNA (dsDNA) fragments, the method comprising:

providing a sample comprising dsDNA;

randomly shearing the dsDNA to a defined average length to provide a population of dsDNA fragments;

preparing the fragments for end-ligation;

ligating to the ends of the fragments a stem-loop adapter comprising a single deoxyuridine adjacent to or within a single-stranded loop sequence comprising a palindromic sequence for intramolecular ligation, to prepare a population of ligated linear dsDNA fragments;

contacting the population of ligated linear dsDNA fragments with an exonuclease to degrade any remaining linear fragments with unligated ends, to produce a purified population of ligated linear dsDNA fragments, contacting the purified population of ligated linear dsDNA fragments with enzymes that nick the ligated dsDNA fragments at the deoxyuridine and remove a 3' terminal phosphate;

incubating the nicked linear dsDNA fragments under conditions sufficient to promote intramolecular ligation and formation of circular dsDNA molecules;

purifying the ligated circular dsDNA fragments by using an exonuclease to degrade any unligated non-circular fragments, thereby preparing a library of covalently closed fully circular dsDNA fragments.

2. The method of claim 1, further comprising contacting the library of covalently closed fully circular dsDNA fragments with an engineered nuclease to induce site-specific cleavage;

preparing the cleaved fragments for end-ligation;

ligating a sequencing adapter comprising at least a single deoxyuridine and a primer site compatible for use in PCR priming or sequencing, at the cleavage site;

contacting the library with enzymes that nick at the deoxyuridine; and sequencing resulting fragments using primers that bind to the sequencing adapter.

3. The method of claim 2, wherein the engineered nuclease cleaves at on- and/or off-target sites.

4. The method of claim 2, wherein the engineered nuclease induces blunt or staggered/overhanging ends.

5. The method of claim 2, wherein the engineered nuclease is selected from the group consisting of meganucleases, MegaTALs, zinc-finger nucleases, transcription activator effector-like nucleases (TALEN), Clustered Regularly Interspaced Short Palindromic Repeats (CRISPR)/Cas RNA-guided nucleases (CRISPR/Cas RGNs), and FokI-dCas9 fusion proteins.

6. The method of claim 5, wherein the CRISPR/Cas RGN is Cas9 or Cpf1.

7. The method of claim 2, wherein treating the sample with an engineered nuclease to induce site-specific cleavage, comprises contacting the sample with a Cas9 nuclease complexed with a specific guide RNA (gRNA).

8. The method of claim 7, wherein the engineered nuclease is a Cas9 nuclease, and the method also includes utilizing a guide RNA that directs the Cas9 nuclease to a target sequence in the genome.

9. The method of claim 2, wherein the primer site comprises a next generation sequencing primer binding sequence, a randomized DNA barcode or unique molecular identifier (UMI).

10. The method of claim 2, wherein the sequencing adapter comprises:
a first region;
a second region that forms one or more hairpin loops and comprises a primer site compatible for use in PCR priming and/or sequencing;
a third region that is complementary to the first region with one additional nucleotide; and
wherein the single deoxyuridine is between the second and third regions.

11. The method of claim 10, further comprising:
contacting the library with enzymes to nick at the deoxyuridine in the sequencing adapter;
using PCR amplification to enrich for adapter-ligated fragments and to add a full sequencing adapter, and
sequencing those fragments bearing a sequencing adapter.

12. The method of claim 11, wherein the enzymes to nick at the deoxyuridine comprise uracil DNA glycosylase (UDG) and/or endonuclease VIII.

13. The method of claim 1, wherein the stem-loop adapter comprises:
a first region;
a second region that forms one or more loops and comprises a single deoxyuridine nucleotide adjacent to a palindromic sequence for intramolecular ligation; and
a third region that is complementary to the first region with one additional nucleotide.

14. The method of claim 13, wherein preparing the fragments for end-ligation comprises and then A-tailing the resulting ends.

15. The method of claim 1, wherein randomly shearing the dsDNA comprises randomly shearing the dsDNA to an average length of 200-500 bps.

16. The method of claim 1, wherein the exonuclease used to degrade any remaining linear fragments with unligated ends is a cocktail of nucleases comprising one or more of bacteriophage Lambda exonuclease, *E. coli* Exonuclease I, and an ATP-dependent exonuclease.

17. The method of claim 1, wherein preparing the fragments for end-ligation comprises one or both of end-repairing and A-tailing the sheared DNA.

18. The method of claim 1, wherein the enzyme that nicks at the deoxyuridine comprises one or both of uracil DNA glycosylase (UDG) and endonuclease VIII, and the enzyme that removes the terminal 3' phosphate comprises T4 Polynucleotide Kinase.

19. The method of claim 1, wherein the DNA is genomic DNA (gDNA) or synthetic DNA.

* * * * *

UNITED STATES PATENT AND TRADEMARK OFFICE
CERTIFICATE OF CORRECTION

PATENT NO. : 9,850,484 B2
APPLICATION NO. : 15/282800
DATED : December 26, 2017
INVENTOR(S) : J. Keith Joung and Shengdar Tsai It is certified that error appears in the above-identified patent and that said Letters Patent is hereby corrected as shown below:

In the Specification

In Column 3, Line 46, delete "activator effector-like" and insert --activator-like effector--

In Column 3, Line 66, delete "activator effector-like" and insert --activator-like effector--

In Column 12, Line 47, delete "activator effector-like" and insert --activator-like effector--

In the Claims

In Column 82, Lines 61-62, in Claim 5, delete "activator effector-like" and insert --activator-like effector--

In Column 84, Line 10, in Claim 14, after "comprises" insert --end-repairing--

Signed and Sealed this
Twenty-sixth Day of June, 2018

Andrei Iancu
*Director of the United States Patent and Trademark Office*

UNITED STATES PATENT AND TRADEMARK OFFICE
CERTIFICATE OF CORRECTION

PATENT NO. : 9,850,484 B2  
APPLICATION NO. : 15/282800  
DATED : December 26, 2017  
INVENTOR(S) : J. Keith Joung and Shengdar Tsai Page 1 of 1

It is certified that error appears in the above-identified patent and that said Letters Patent is hereby corrected as shown below:

In the Specification

In Column 1, Line 16, replace "No." with -- Nos. --

In Column 1, Line 16, after "GM105378" insert -- and R35 GM118158 --

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*